United States Patent
Sharpless et al.

(10) Patent No.: US 9,616,062 B2
(45) Date of Patent: *Apr. 11, 2017

(54) CYCLIN DEPENDENT KINASE INHIBITORS AND METHODS OF USE

(71) Applicant: The University of North Carolina at Chapel Hill, Chapel Hill, NC (US)

(72) Inventors: Norman E. Sharpless, Chapel Hill, NC (US); Patrick J. Roberts, Durham, NC (US); Kwok-Kin Wong, Chapel Hill, NC (US); Soren Johnson, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/103,359

(22) Filed: Dec. 11, 2013

(65) Prior Publication Data

US 2014/0227222 A1    Aug. 14, 2014

Related U.S. Application Data

(63) Continuation of application No. 13/319,828, filed as application No. PCT/US2010/034816 on May 13, 2010, now abandoned.

(60) Provisional application No. 61/177,724, filed on May 13, 2009.

(51) Int. Cl.
| | | |
|---|---|---|
| *A61K 35/00* | (2006.01) | |
| *A61K 31/519* | (2006.01) | |
| *A61K 38/18* | (2006.01) | |
| *A61K 45/06* | (2006.01) | |

(52) U.S. Cl.
CPC ........ *A61K 31/519* (2013.01); *A61K 38/1816* (2013.01); *A61K 45/06* (2013.01)

(58) Field of Classification Search
CPC .............. A61K 38/1816; A61K 31/519; A61K 2300/00
See application file for complete search history.

(56) References Cited

U.S. PATENT DOCUMENTS

| | | | |
|---|---|---|---|
| 5,591,855 A | 1/1997 | Hudkins et al. | |
| 5,628,984 A | 5/1997 | Boucher | |
| 5,739,110 A * | 4/1998 | Bogden et al. ............. | 424/85.2 |
| 6,291,504 B1 | 9/2001 | Nugiel et al. | |
| 6,369,086 B1 | 4/2002 | Davis | |
| 6,521,759 B2 | 2/2003 | Kim et al. | |
| 6,610,684 B2 | 8/2003 | Zaharevitz et al. | |
| 6,667,346 B2 | 12/2003 | Reddy et al. | |
| 6,936,612 B2 | 8/2005 | Barvian et al. | |
| 6,982,277 B2 | 1/2006 | Gudkov et al. | |
| 7,208,489 B2 | 4/2007 | Barvian et al. | |
| 7,345,171 B2 | 3/2008 | Beylin et al. | |
| 8,598,186 B2 | 12/2013 | Tavares et al. | |
| 8,598,197 B2 | 12/2013 | Tavares et al. | |
| 2002/0137778 A1 | 9/2002 | Kim et al. | |
| 2003/0069430 A1 | 4/2003 | Davis et al. | |
| 2003/0073668 A1 | 4/2003 | Booth et al. | |
| 2003/0229026 A1 | 12/2003 | Al-Awar et al. | |
| 2004/0006074 A1 | 1/2004 | Kelley et al. | |
| 2004/0048915 A1 | 3/2004 | Engler et al. | |
| 2005/0222163 A1 | 10/2005 | Eck et al. | |
| 2007/0027147 A1 | 2/2007 | Hayama et al. | |
| 2007/0179118 A1 | 8/2007 | Barvian et al. | |
| 2007/0270362 A1 * | 11/2007 | Harlan et al. ................... | 514/44 |
| 2008/0085890 A1 | 4/2008 | Tsou et al. | |
| 2008/0161355 A1 | 7/2008 | Curry et al. | |
| 2008/0182853 A1 | 7/2008 | Kruman et al. | |
| 2011/0224221 A1 | 9/2011 | Sharpless et al. | |
| 2011/0224227 A1 | 9/2011 | Sharpless et al. | |
| 2012/0100100 A1 | 4/2012 | Sharpless et al. | |
| 2013/0303543 A1 | 11/2013 | DiRocco et al. | |
| 2015/0111896 A1 | 4/2015 | Sharpless et al. | |

FOREIGN PATENT DOCUMENTS

| | | |
|---|---|---|
| CN | 1278794 | 1/2001 |
| CN | 1379668 | 11/2002 |
| CN | 2656290 | 1/2008 |
| EP | 2429566 | 3/2012 |
| JP | 2001-517652 | 10/2001 |
| JP | 2005-519909 | 7/2005 |
| JP | 2005-526920 | 9/2005 |
| JP | 2007-530425 | 11/2007 |
| JP | 2007-530654 | 11/2007 |
| WO | WO98/33798 | 8/1998 |
| WO | WO99/15500 | 4/1999 |
| WO | WO01/12188 | 2/2001 |

(Continued)

OTHER PUBLICATIONS

Chen et al., J. Natl. Cancer Inst 2000, 92: 1999-2008.*
Fry et al., Mol. Cancer Ther. 2004, 3: 1427-1437.*
Walkley et al., Nature Cell Biology,7:172-178, 2005.*
Baughn et al., "A Novel Orally Active Small Molecule Potently Induces $G_1$ Arrest in Primary Myeloma Cells and Prevents Tumor Growth by Specific Inhibition of Cyclin-Dependent Kinase 4/6," Cancer Research. vol. 66, No. 15 pp. 7661-7667 (2006).
Bernhard et al., "Reducing the radiation-induced $G_2$ delay causes HeLa cells to undergo apoptosis instead of mitotic death," Int. J. Radiat. Biol. vol. 69, No. 5 pp. 575-584 (1996).
Blagosklonny et al., "Exploiting Cancer Cell Cycling for Selective Protection of Normal Cells," Cancer Research. vol. 61 pp. 4301-4305 (2001).

(Continued)

*Primary Examiner* — Gyan Chandra
(74) *Attorney, Agent, or Firm* — Jenkins, Wilson, Taylor & Hunt

(57) ABSTRACT

The presently disclosed subject matter relates to methods and compositions for protecting healthy cells from damage due to DNA damaging agents. In particular, the presently disclosed subject matter relates to the protective action of selective cyclin dependent kinase 4/6 (CDK4/6) inhibitors administered to subjects that have been exposed to or that are at risk of exposure to DNA damage.

17 Claims, 24 Drawing Sheets

(56) References Cited

FOREIGN PATENT DOCUMENTS

| | | |
|---|---|---|
| WO | WO02/44174 | 6/2002 |
| WO | WO03062236 | 7/2003 |
| WO | WO03100147 | 12/2003 |
| WO | WO 2004/065378 A1 | 8/2004 |
| WO | WO2005/005426 | 1/2005 |
| WO | WO2005/094830 | 10/2005 |
| WO | WO2006/002119 A2 | 1/2006 |
| WO | WO2006/074985 | 7/2006 |
| WO | WO2007/140222 | 12/2007 |
| WO | WO2008/005538 | 1/2008 |
| WO | WO 2008/076946 | 6/2008 |
| WO | WO2008/079933 | 7/2008 |
| WO | WO2009/061345 | 5/2009 |
| WO | WO2009/085185 A1 | 7/2009 |
| WO | WO 2010/020675 | 2/2010 |
| WO | WO2010/039997 | 4/2010 |
| WO | WO2010/051127 | 5/2010 |
| WO | WO2010/132725 | 11/2010 |
| WO | WO2012/061156 | 5/2012 |
| WO | WO2012/068381 | 5/2012 |

OTHER PUBLICATIONS

Bucher, N., and Britten, C.D., "G2 checkpoint abrogation and checkpoint kinase-I targeting in the treatment of cancer," British Journal of Cancer. vol. 98 pp. 523-528 (2008).
Burdelya et al., "An Agonist of Toll-Like Receptor 5 Has Radioprotective Activity in Mouse and Primate Models," Science. vol. 320 pp. 226-230 (2008).
Chen et al., "Protection of Normal Proliferating Cells Against Chemotherapy by Staurosporine-Mediated, Selective, and Reversible $G_1$ Arrest," Journal of the National Cancer Institute. vol. 92, No. 24 pp. 1999-2008 (2000).
Chu et al., "Discovery of [4-Amino-2-(1-methanesulfonylpiperidin-4-ylamino)pyrimidin-5-yl](2,3-difluoro-6-methoxyphenypmethanone (R547), A Potent and Selective Cyclin-Dependent Kinase Inhibitor with Significant in Vivo Antitumor Activity," J. Med. Chem. vol. 49 pp. 6549-6560 (2006).
Davis et al., "Prevention of Chemotherapy-Induced Alopecia in Rats by CDK Inhibitors," Science. vol. 291 pp. 134-137 (2001).
Davis et al., "Retraction", Science. vol. 298 p. 2327 (2002).
Davis et al. "Genistein Induces Radioprotection by Hematopoietic Stem Cell Quiescence," International Journal of Radiation Biology. vol. 84, No. 9 pp. 713-726 (2008).
Dickson, M.A., and Schwartz, G.K., "Development of cell-cycle inhibitors for cancer therapy," Current Oncology. vol. 16, No. 2 pp. 36-43 (2009).
Dickson et al. "Phase II Trial of the CDK4 Inhibitor PD0332991 in Patients with Advanced CDK4-Amplified Well-Differentiated or Dedifferentiated Liposarcoma," Journal of Clinical Oncology. vol. 31, No. 16 pp. 2024-2028 (2013).
El-Deiry, "Meeting Report: The International Conference on Tumor Progression and Therapeutic Resistance," Cancer Research. vol. 65, No. 11 pp. 4475-4484 (2005).
Engler et al., "Novel, Potent and Selective Cyclin D1/CDK4 Inhibitors: Indolo[6,7-a]pyrrolo[3,4-c]carbazoles," Bioorganic & Medicinal Chemistry Letters. vol. 13 pp. 2261- 2267 (2003).
Extended European Search Report corresponding to European Patent Application No. 09 818 530.9-1216 dated Sep. 24, 2012.
Extended European Search Report corresponding to European Patent Application No. 09 823 989.0-2123 dated May 11, 2012.
Extended European Search Report corresponding to European Patent Application No. 10 775 575.3-1456 dated Aug. 5, 2013.
Finn et al., "PD 0332991, a selective cyclin D kinase 4/6 inhibitor, preferentially inhibits proliferation of luminal estrogen receptor-positive human breast cancer cell lines in vitro," Breast Cancer Research. vol. 11, No. 5 p. R77 (2009).

Fry et al., "Specific inhibition of cyclin-dependent kinase 4/6 by PD 0332991 and associated antitumor activity in human tumor xenografts," Molecular Cancer Therapeutics. vol. 3, No. 11 pp. 1427-1437 (2004).
Guo et al., "Staurosporine modulates radiosensitivity and radiation-induced apoptosis in U937 cells," Int. J. Radiat. Biol. vol. 82, No. 2 pp. 97-109 (2006).
Hallahan et al., "Inhibition of Protein Kinases Sensitizes Human Tumor Cells to Ionizing Radiation," Radiation Research. vol. 129 pp. 345-350 (1992).
Hérodin et al., "Short-term injection of antiapoptotic cytokine combinations soon after lethal γ-irradiation promotes survival," Blood. vol. 101 pp. 2609-2616 (2003).
Hershman et al., "Acute Myeloid Leukemia or Myelodysplastic Syndrome Following Use of Granulocyte Colony-Stimulating Factors During Breast Cancer Adjuvant Chemotherapy," J. Natl. Cancer Inst. vol. 99, No. 3 pp. 196-205 (2007).
Hirose et al., "Abrogation of the Chk1-mediated $G_2$ Checkpoint Pathway Potentiates Temozolomide-induced Toxicity in a p53-independent Manner in Human Glioblastoma Cells," Cancer Research. vol. 61 pp. 5843-5849 (2001).
Honma et al., "A Novel Approach for the Development of Selective Cdk4 Inhibitors: Library Design Based on Locations of Cdk4 Specific Amino Acid Residues," J. Med. Chem. vol. 44 pp. 4628-4640 (2001).
Honma et al., "Structure-Based Generation of a New Class of Potent Cdk4 Inhibitors: New de Novo Design Strategy and Library Design," J. Med. Chem. vol. 44 pp. 4615-4627 (2001).
Ikuta et al., "Crystallographic Approach to Identification of Cyclin-dependent Kinase 4 (CDK4)-specific Inhibitors by Using CDK4 Mimic CDK2 Protein," The Journal of Biological Chemistry. vol. 276, No. 29 pp. 27548-27554 (2001).
Johnson, N., and Shapiro, G.I., "Cyclin-dependent kinase 4/6 inhibition in cancer therapy," Cell Cycle. vol. 11, No. 21 pp. 3913-3918 (2012).
Johnson et al., "Mitigation of Hematologic Radiation Toxicity in Mice Through Pharmacological Quiescence Induced by CDK4/6 Inhibition," J. Clin. Investigation. vol. 120 pp. 2528-2536 (2010).
Karaman et al., "A quantitative analysis of kinase inhibitor selectivity," Nature Biotechnology. vol. 26, No. 1 pp. 127-132 (2008).
Keyomarsi, K., and Pardee, A.B., "Selective protection of normal proliferating cells against the toxic effects of chemotherapeutic agents," Progress in Cell Cycle Research. vol. 5 pp. 527-532 (2003).
Kim et al., "Enhancement of Radiation Effects of Flavopiridol in Uterine Cervix Cancer Cells," Cancer Research Treatment. vol. 37, No. 3 pp. 191-195 (2005).
Knockaert et al., "Pharmacological inhibitors of cyclin-dependent kinases," Trends in Pharmacological Sciences. vol. 23, No. 9 pp. 417-425 (2002).
Kubo et al., "The p16 Status of Tumor Cell Lines Identifies Small Molecule Inhibitors Specific for Cyclin-dependent Kinase 4," Clinical Cancer Research. vol. 5 pp. 4279-4286 (1999).
Laredo et al., "Effect of the Protein Kinase C Inhibitor Staurosporine on Chemosensitivity to Daunorubicin of Normal and Leukemic Fresh Myeloid Cells," Blood. vol. 84, No. 1 pp. 229-237 (1994).
Luo et al., "Blocking CHK1 Expression Induces Apoptosis and Abrogates the G2 Checkpoint Mechanism," Neoplasia. vol. 3, No. 5 pp. 411-419 (2001).
McInnes et al., "Progress in the Evaluation of CDK Inhibitors as Anti-Tumor Agents," Drug Discovery Today. vol. 13 pp. 875-881 (2008).
Menu et al., "A Novel Therapeutic Combination Using PD 0332991 and Bortezomib: Study in the 5T33MM Myeloma Model," Cancer Research. vol. 68, No. 14 pp. 5519-5523 (2008).
Michaud et al., "Pharmacologic Inhibition of Cyclin-Dependent Kinases 4 and 6 Arrests the Growth of Glioblastoma Multiforme Intracranial Xenografts," Cancer Research. vol. 70, No. 8 pp. 3228-3238 (2010).
Notification Concerning Transmittal of International Preliminary Report on Patentability (Chapter I of the Patent Cooperation Treaty) corresponding to International Patent Application No. PCT/US2011/061202 dated May 30, 2013.

(56) References Cited

OTHER PUBLICATIONS

Notification of Transmittal of the International Preliminary Examination Report (PCT Rule 71.1) corresponding to PCT/US2010/034816 dated May 25, 2012.
Notification of Transmittal of the International Preliminary Examination Report on Patentabilty (Chapter II of the Patent Cooperation Treaty) corresponding to International Patent Application No. PCT/US2009/059254 dated Dec. 6, 2011.
Notification of Transmittal of the International Preliminary Examination Report on Patentability (Chapter II of the Patent Cooperation Treaty) corresponding to International Patent Application No. PCT/US2009/059281 dated Nov. 23, 2011.
Notification of Transmittal of the International Search Report and the Written Opinion of the International Searching Authority, or the Declaration corresponding to International Patent Application No. PCT/US2009/059254 dated May 6, 2010.
Notification of Transmittal of the International Search Report and the Written Opinion of the International Searching Authority, or the Declaration corresponding to International Patent Application No. PCT/US2009/059281 dated Dec. 24, 2010.
Notification of Transmittal of the International Search Report and the Written Opinion of the International Searching Authority, or the Declaration corresponding to International Patent Application No. PCT/US2010/034816 dated Jan. 28, 2011.
Notification of Transmittal of the International Search Report and the Written Opinion of the International Searching Authority, or the Declaration corresponding to International Patent Application No. PCT/US2011/061202 dated May 16, 2012.
O'Dwyer et al., "A phase I dose escalation trial of a daily oral CDK 4/6 inhibitor PD-0332991," J. Clin. Oncol. vol. 25, No. 18 (ASCO, Chicago, Illinois, 2007) [Abstract].
Official Action corresponding to Chinese Patent Application No. 200980148408.0 dated Oct. 31, 2012.
Official Action corresponding to Chinese Patent Application No. 200980148408.0 dated Sep. 16, 2013.
Official Action corresponding to Chinese Patent Application No. 200980148409.5 dated Oct. 31, 2012.
Official Action corresponding to Chinese Patent Application No. 200980148409.5 dated Sep. 16, 2013.
Official Action corresponding to Chinese Patent Application No. 201080031866.9 dated Mar. 5, 2013.
Official Action corresponding to Chinese Patent Application No. 201080031866.9 dated Nov. 21, 2013.
Official Action correponding to European Patent Application No. 10 775 575.3-1456 dated Mar. 31, 2014.
Official Action corresponding to European Patent Application No. 09 823 989.0-1464 dated May 8, 2014.
Official Action corresponding to Israeli Patent Application No. 212103 dated Nov. 13, 2012.
Official Action corresponding to Israeli Patent Application No. 212104 dated Nov. 13, 2012.
Official Action corresponding to Israeli Patent Application No. 216315 dated Jan. 16, 2013.
Offical Action corresponding to Japanese Patent Application No. 2011-530243 dated Feb. 22, 2013.
Official Action corresponding to Japanese Patent Application No. 2011-530251 dated Dec. 26, 2013.
Official Action corresponding to Japanese Patent Application No. 2011-530243 dated Jan. 20, 2014.
Official Action corresponding to U.S. Appl. No. 13/122,017 dated Nov. 20, 2012.
Official Action corresponding to U.S. Appl. No. 13/122,017 dated Jan. 17, 2013.
Official Action corresponding to U.S. Appl. No. 13/122,017 dated Oct. 10, 2013.
Official Action corresponding to U.S. Appl. No. 13/122,061 dated Oct. 25, 2012.
Official Action corresponding to U.S. Appl. No. 13/122,061 dated Feb. 12, 2013.
Official Action corresponding to U.S. Appl. No. 13/122,061 dated Aug. 23, 2013.
Official Action corresponding to U.S. Appl. No. 13/319,828 dated Dec. 12, 2012.
Official Action corresponding to U.S. Appl. No. 13/319,828 dated Jun. 11, 2013.
Official Action corresponding to U.S. Appl. No. 13/122,017 dated May 12, 2014.
Ojeda et al., "Role of protein kinase-C in thymocyte apoptosis induced by irradiation," Int. J. Radiat. Biol. vol. 61, No. 5 pp. 663-667 (1992).
Pawlik et al., "Role of Cell Cycle in Mediating Sensitivity to Radiotherapy," Int. J. Radiation Oncology Biol. Phys. vol. 59 pp. 928-942 (2004).
Ramsey et al., "Expression of $p16^{Ink4a}$ Compensates for $p18^{Ink4c}$ Loss in Cyclin-Dependent Kinase 4/6-Dependent 4/6-Dependent Tumors and Tissues," Cancer Research. vol. 67, No. 10 pp. 4732-4741 (2007).
Sanchez-Martinez et al., "Aryl[a]pyrrolo[3,4-c]carbazoles as Selective Cyclin D1-CDK4 Inhibitors," Bioorganic & Medicinal Chemistry Letters. vol. 13 pp. 3835-3839 (2003).
Sanchez-Martinez et al., "Studies on Cyclin-Dependent Kinase Inhibitors: Indolo-[2,3-a]pyrrolo[3,4-c]carbazoles versus Bisindolylmaleimides," Bioorganic & Medicinal Chemistry Letters. vol. 13 pp. 3841-3846 (2003).
Schmidt et al., "Protection against chemotherapy-induced cytotoxicity by cyclin-dependent kinase inhibitors (CKI) in CKI-responsive cells compared with CKI-unresponsive cells," Oncogene. vol. 20 pp. 6164-6171 (2001).
Search Report corresponding to Chinese Patent Application No. 200980148409.5 dated Sep. 16, 2013.
Search Report corresponding to Chinese Patent Application No. 200980148408.0 dated Sep. 16, 2013.
Seed, T. M., "Radiation Protectants: Current Status and Future Prospects," Health Physics. vol. 89 pp. 531-545 (2005).
Sharpless et al., "Both products of the mouse Ink4a/Arf locus suppress melanoma formation in vivo," Oncogene. vol. 22 pp. 5055-5059 (2003).
Shimamura et al., "Identification of potent 5-pyrimidinyl-2-aminothiazole CDK4, 6 inhibitors with significant selectivity over CDK1, 2, 5, 7, and 9," Bioorganic & Medicinal Chemistry Letters. vol. 16 pp. 3751-3754 (2006).
Sicinski, P., "Cyclins and Cyclin-Dependent Kinases as Targets for Protection Against Radiation," Abstract downloaded from http://projectreporter.nih.gov/project_info_description.cfm on Sep. 28, 2009.
Sinclair, W.K., and Morton, R.A., "X-Ray Sensitivity during the Cell Generation Cycle of Cultured Chinese Hamster Cells," Radiation Research. vol. 29 pp. 450-474 (1966).
Soni et al., "Selective In Vivo and In Vitro Effects of a Small Molecule Inhibitor of Cyclin-Dependent Kinase 4," Journal of the National Cancer Institute. vol. 93, No. 6 pp. 436-446.
STN Registry No. 571190-30-2. "PD 0332991". Retreived from STN Feb. 7, 2013. 1 page.
Stone et al., "Reversible, p16-mediated Cell Cycle Arrest as Protection from Chemotherapy," Cancer Research. vol. 56 pp. 3199-3202 (1996).
Teyssier et al., "Cell cycle regulation after exposure to ionizing radiation," Bulletin du Cancer. vol. 86, No. 4 pp. 345-357 (1999) [Abstract].
Toogood et al., "Discovery of a Potent and Selective Inhibitor of Cyclin-Dependent Kinase 4/6," Journal of Medicinal Chemistry. vol. 48, No. 7 pp. 2388-2406 (2005).
Tsou et al., "4-(Phenylaminonnethylene)isoquinoline-1,3(2H,4H)-diones as Potent and Selective Inhibitors of the Cyclin-Dependent Kinase 4 (CDK4)," Journal of Medicinal Chemistry. vol. 51, No. 12 pp. 3507-3525 (2008).
Tsou et al., "Discovery of 4-(Benzylaminonnethylene)isoquinoline-1,3-(2H,4H)-diones and 4-[(Pyridylmethyl)aminomethylene]isoquinoline-1,3(2H,4H)-diones as Potent and Selective Inhibitors of the Cyclin-Dependent Kinase 4," Journal of Medicinal Chemistry. vol. 52, No. 8 pp. 2289-2310 (2009).

(56) References Cited

OTHER PUBLICATIONS

Tu et al., "New potential inhibitors of cyclin-dependent kinase 4: Design and synthesis of pyrido[2,3-d]pyrimidine derivatives under microwave irradiation," Bioorganic & Medicinal Chemistry Letters. vol. 16 pp. 3578-3581 (2006).
Uckun et al., "In Vivo Radioprotective Effects of Recombinant Human Granulocyte Colony-Stimulating Factor in Lethally Irradiated Mice," Blood. vol. 75, No. 3 pp. 638-645 (1990).
VanderWel et al., "Pyrido[2,3-d]pyrimidin-7-ones as Specific Inhibitors of Cyclin-Dependent Kinase 4," Journal of Medicinal Chemistry. vol. 48, No. 7 pp. 2371-2387 (2005).
Wang et al., "Protein kinase inhibitor staurosporine enhances cytotoxicity of antitumor drugs to cancer cells," Yao Xue Xue Bao. vol. 31, No. 6 pp. 411-415 (1996) [Abstract].
Weiss, J.F., and Landauer, M.R., "History and development of radiation-protective agents," Int. J. Radiat. Biol. vol. 85, No. 7 pp. 539-573 (2009).
Zhang et al., "Sensitization of C6 glioma cells to radiation by staurosporine, a potent protein kinase C inhibitor," Journal of Neuro-Oncology, vol. 15 pp. 1-7 (1993).
Zhu et al., "Synthesis of Quinolinyl/Isoquinolinyl[a]pyrrolo [3,4-c] Carbazoles as Cyclin D1/CDK4 Inhibitors," Bioorganic & Medicinal Chemistry Letters. vol. 13 pp. 1231-1235 (2003).
Zhu et al., "Synthesis, Structure-Activity Relationship, and Biological Studies of Indolocarbazoles as Potent Cyclin D1-CDK4 Inhibitors," Journal of Medicinal Chemistry. vol. 46, No. 11 pp. 2027-2030 (2003).
Communication pursuant to Article 94(3) EPC corresponding to European Patent Application No. 10 775 575.3-1456 dated Oct. 13, 2014.
Engler et al., "The Development of Potent and Selective Bisarylmaleimide GSK3 inhibitors," Biorg. Med. Chem. Lett. vol. 15, No. 4, pp. 899-903 (2005).
Hara et al., "Regulation of p16CDKN2 Expression and Its Implications for Cell Immortalization and Senescence," Molecular and Cellular Biology. vol. 16, No. 3 pp. 859-867 (1996).
Invitation pursuant to Rule 63(1) EPC corresponding to European Patent Application No. 11 842 009.0-1453 dated Sep. 19, 2014.
Official Action corresponding to Chinese Patent Application No. 201180065126.1 dated Jul. 3, 2014.
Daemen et al., "Apoptosis and Inflammation in Renal Reperfusion Injury," Transplantation, vol. 73, No. 11, pp. 1693-1700 (2002).
Dickson, "Molecular Pathways: CDK4 Inhibitors for Cancer Therapy," American Association for Cancer Research. vol. 20, pp. 3379-3383 (2014).
Dirocco et al., "CDK4/6 Inhibition Induces Epithelial Cell Cycle Arrest and Ameliorates Acute Kidney Injury," American Journal of Physiology: Renal Physiology, vol. 306, No. 4, pp. F379-F388 (2014).
Extended European Search Report corresponding to European Patent Application No. 11842009.0-1453 dated Jan. 27, 2015.
Official Action corresponding to European Patent Application No. 09 823 989.0-1464 dated Feb. 12, 2015.
Official Action corresponding to U.S. Appl. No. 13/122,017 dated Mar. 16, 2015.
Official Action corresponding to U.S. Appl. No. 14/495,381 dated Feb. 4, 2015.
Price, "Dependence of Cisplatin-Induced Cell Death In Vitro and In Vivo on Cyclin-Dependent Kinase 2," Journal of the American Society of Nephrology, vol. 17, No. 9, pp. 2434-2442 (2006).
Advisory Action corresponding to U.S. Appl. No. 13/122,017 dated Jul. 23, 2015.
Advisory Action corresponding to U.S. Appl. No. 13/122,017 dated Jun. 24, 2015.
Communication under Rule 71(3) EPC corresponding to European Patent Application No. 10 775 575.3-1456 dated Jun. 26, 2015.
Official Action corresponding to European Patent Application No. 09 818 530.9-1453 dated Jul. 7, 2015.
Official Action corresponding to U.S. Appl. No. 14/495,381 dated May 19, 2015.
Decision to grant a European patent pursuant to Article 97(1) EPC corresponding to Application No. 10775575.3-1456 dated Dec. 10, 2015.
Mahboobi et al. "Synthesis of Pyrrolidin-2-Ones and of Staurosporine Aglycon (K-252c) by Intermolecular Michael Reaction". J. Org. Chem. vol. 64 pp. 4697-4704 (1999).
Official Action corresponding to U.S. Appl. No. 13/988,158 dated Feb. 16, 2016.
Official Action corresponding to U.S. Appl. No. 14/495,381 dated Nov. 18, 2015.
Retzer-Lidl et al. "Inhibition of CDK4 Impairs Proliferation of Pancreatic Cancer Cells and Sensitizes Towards TRAIL-Induced Induced Apoptosis via Downregulation of Survivin". Int. J. Cancer. vol. 121 pp. 66-75 (2007).
Notice of Publication corresponding to European Application No. 15196712.2-1466 dated May 4, 2016.
Official Action corresponding to U.S. Appl. No. 13/988,158 dated Aug. 24, 2016.
Pabla et al., "Mitigation of acute kidney injury by cell-cycle inhibitors that suppres both CDK4/6 and OCT2 functions," PNAS. vol. 112, No. 16, pp. 5231-5236 (2015).
Extended European Search Report corresponding to European Patent Application No. 15196712.2-1456 dated Feb. 29, 2016.
Official Action corresponding to U.S. Appl. No. 13/122,017 dated Apr. 8, 2016.
Restriction Requirement corresponding to U.S. Appl. No. 13/988,158 dated Feb. 16, 2016.
Communication pursuant to Article 94(3) EPC corresponding to European Application No. 15 196 712.2 dated Jan. 17, 2017.
Offical Action corresponding to U.S. Appl. No. 13/122,017 dated Jan. 20, 2017.

\* cited by examiner

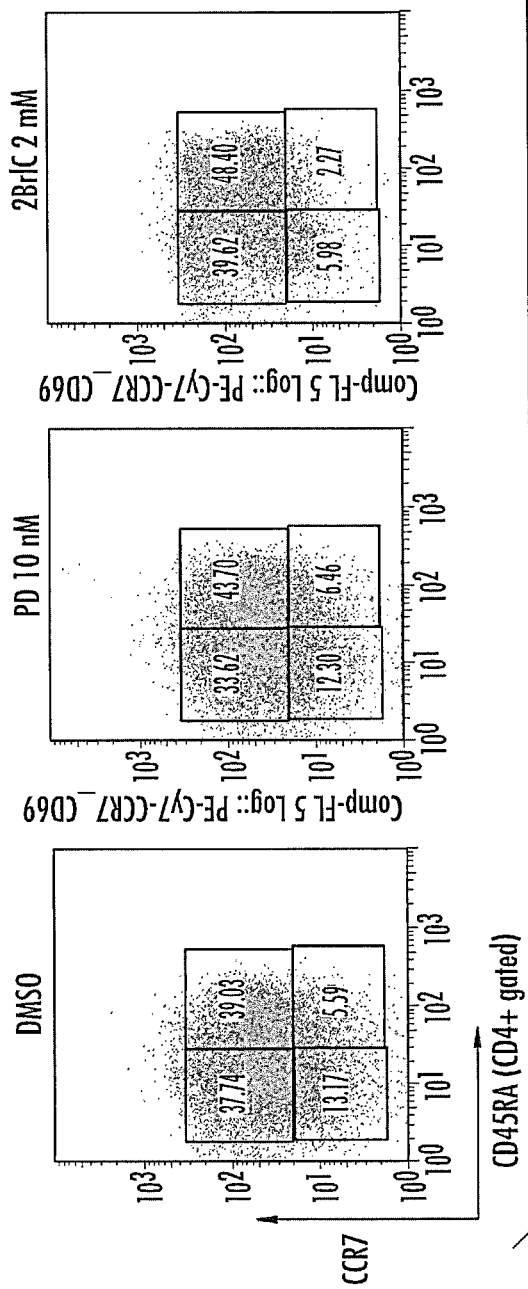
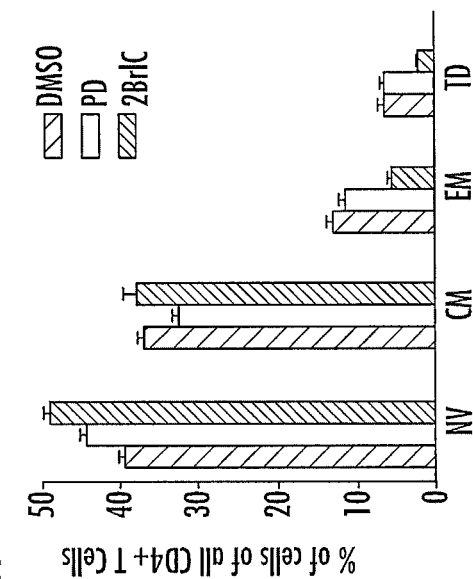
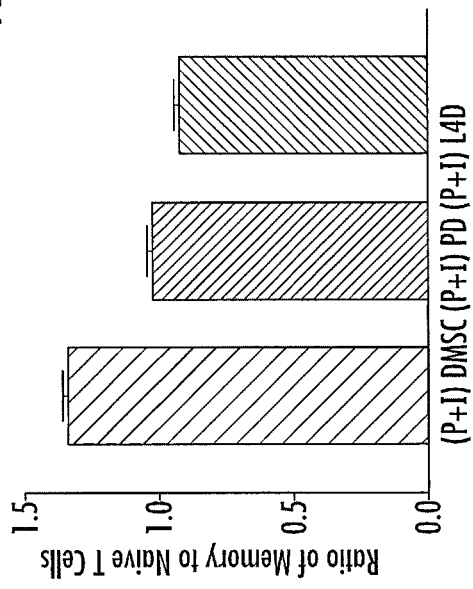
FIG. 17A
FIG. 17B
FIG. 17C

CYCLIN DEPENDENT KINASE INHIBITORS AND METHODS OF USE

RELATED APPLICATIONS

This application is a continuation of U.S. patent application Ser. No. 13/319,828, filed on Dec. 29, 2011, which is a national stage application of International Application No. PCT/US2010/034816, filed on May 13, 2010, which claims priority to U.S. Provisional Application Ser. No. 61/177,724, filed May 13, 2009; the disclosures of each of which are incorporated herein by reference in their entireties.

GOVERNMENT INTEREST

This invention was made with government support under Grant Nos. AG024379 & CA090679 awarded by the National Institutes of Health. The government has certain rights in the invention.

TECHNICAL FIELD

The presently disclosed subject matter relates to methods and compositions for protecting healthy cells from DNA damage and augmenting the efficacy of toxicity reducing agents, such as growth factors. In addition, the presently disclosed subject matter relates to methods and compositions for treating autoimmune diseases by blocking the proliferation of certain immune cells. In particular, the presently disclosed subject matter relates to uses of selective cyclin dependent kinase 4/6 (CDK4/6) inhibitors to induce pharmacologic quiescence in certain stem and progenitor cell populations within a mammalian subject and thereby enhancing clinical outcomes for that subject.

ABBREVIATIONS

%=percentage
μg=microgram
μL=microliters
μM=micromolar
2BrIC=2-bromo-12,13-dihydro-5H-indolo[2,3-a]pyrrolo[3,4]-carbazole-5,6-dione
BM=bone marrow
BM-MNC=bone marrow mononuclear cells
BrdU=5-bromo-2-deoxyuridine
BUN=blood area nitrogen
CAFC=cobblestone area-forming cell
CBC=complete blood count
CDK=cyclin-dependent kinase
CDK4/6=cyclin dependent kinase 4 and/or cyclin-dependent kinase 6
CLP=common lymphoid progenitors
CMP=common myeloid progenitors
CNS=central nervous system
DMEM=Dulbecco's Modified Eagle Medium
DMSO=dimethyl sulfoxide
DNA=deoxyribonucleic acid
DOX=doxorubicin
EPO=erythropoietin
Etop=etoposide
FACS=fluorescence-activated cell sorting
FBS=fetal bovine serum
g=gram
GC=germinal center
G-CSF=granulocyte colony-stimulating factor
GEMM=genetically engineered murine model
GM-CSF=granulocyte-macrophage colony stimulating factor
GMP=granulocyte-monocyte progenitors
Gy=gray
h=hours
HPLC=high performance liquid chromatography
HSC=hematopoietic stem cells
HSPC=hematopoietic stem and progenitor cells
$IC_{50}$=50% inhibitory concentration
IHC=immunohistochemistry
IL=interleukin
IP=intraperitoneal
IR=ionizing radiation
ITP=idiopathic thrombocytopenic purpura
kg=kilogram
LT-HSC=long term hematopoietic stem cell
MEP=megakaryocyte-erythroid progenitors
mg=milligrams
MPP=multipotent progenitor
nM=nanomolar
NP-CGG=nitrophenylacetyl-chicken gamma globulin
PD=6-acetyl-8-cyclopentyl-5-methyl-2-(5-piperazin-1-yl-pyridin-2-ylamino)-8H-pyrido-[2,3-d]-pyrimidin-7-one (also referred to as PD 0332991)
RA=rheumatoid arthritis
RB=retinoblastoma tumor suppressor protein
RLU=relative light units
SEM=standard error of the mean
SLE=systemic lupus erythematosus
ST-HSC=short term hematopoietic stem cell
Sv=sievert
tHDF=telomerized human diploid fibroblast
TTP=thrombotic thrombocytopenic purpura

BACKGROUND

The treatment of cancer often includes the use of DNA damaging drugs and/or other DNA damaging agents, such as ionizing radiation. These treatments can be non-specific and, particularly at high doses, toxic to normal, rapidly dividing cells. This often leads to various side effects in patients undergoing cancer treatment.

For example, bone marrow suppression, a severe reduction of blood cell production in bone marrow, is one such side effect. It is characterized by both myelosuppression (anemia, neutropenia, agranulocytosis and thrombocytopenia) and lymphopenia. Neutropenia is characterized by a selective decrease in the number of circulating neutrophils and an enhanced susceptibility to bacterial infections. Anemia, a reduction in the number of red blood cells or erythrocytes, the quantity of hemoglobin, or the volume of packed red blood cells (characterized by a determination of the hematocrit) affects approximately 67% of cancer patients undergoing chemotherapy in the United States. See *BioWorld Today*, page 4, Jul. 23, 2002. Thrombocytopenia is a reduction in platelet number with increased susceptibility to bleeding. Lymphopenia is a common side-effect of chemotherapy characterized by reductions in the numbers of circulating lymphocytes (also called T- and B-cells). Lymphopenic patients are predisposed to a number of types of infections.

Thus, the medical practitioner typically has to balance the efficacy of chemotherapeutic and radiotherapeutic techniques in destroying abnormal proliferative cells with associated cytotoxic effects on normal cells. Because of this, the therapeutic index of chemotherapy and radiotherapy techniques is narrowed, often resulting in incomplete tumor reduction, tumor recurrence, increasing tumor burden, and induction of chemotherapy and/or radiation resistant tumors.

Numerous methods have been designed in an effort to reduce normal tissue damage while still delivering effective therapeutic doses of DNA damaging agents. With regard to IR, these techniques include brachytherapy, fractionated and hyperfractionated dosing, complicated dose scheduling and delivery systems, and high voltage therapy with a linear accelerator. However, such techniques only attempt to strike a balance between the therapeutic and undesirable effects of the radiation, and full efficacy has not been achieved.

Small molecules have been used to reduce some of the side effects of certain chemotherapeutic compounds. For example, leukovorin has been used to mitigate the effects of methotrexate on bone marrow cells and on gastrointestinal mucosa cells. Amifostine has been used to reduce the incidence of neutropenia-related fever and mucositis in patients receiving alkylating or platinum-containing chemotherapeutics. Also, dexrazoxane has been used to provide cardioprotection from anthracycline anti-cancer compounds. Unfortunately, there is concern that many chemoprotectants, such as dexrazoxane and amifostine, can decrease the efficacy of chemotherapy given concomitantly.

Additional chemoprotectant therapies include the use of growth factors. Hematopoietic growth factors are available on the market as recombinant proteins. These proteins include granulocyte colony stimulating factor (G-CSF) and granulocyte-macrophage colony stimulating factor (GM-CSF) and their derivatives for the treatment of neutropenia, and erythropoietin (EPO) and its derivatives for the treatment of anemia. However, while growth factors can hasten recovery of some blood cell lineages, they do not treat suppression of platelets, macrophages, T-cells or B-cells.

The non-selective kinase inhibitor staurosporine has been shown to afford protection from DNA damaging agents in some cultured cell types. See Chen et al., *J. Natl. Cancer Inst.*, 92, 1999-2008 (2000); and Ojeda et al., *Int. J. Radiat. Biol.*, 61, 663-667 (1992). Staurosporine is a naturally occurring product and non-selective kinase inhibitor that binds most mammalian kinases with high affinity. See Karaman et al., *Nat. Biotechnol.*, 26, 127-132 (2008). Staurosporine treatment can elicit an array of cellular responses including apoptosis, cell cycle arrest and cell cycle checkpoint compromise depending on cell type, drug concentration, and length of exposure. For example, staurosporine has been shown to sensitize cells to DNA damaging agents such as ionizing radiation and chemotherapy (see Bernhard et al., *Int. J. Radiat. Biol.*, 69, 575-584 (1996); Teyssier et al., *Bull. Cancer*, 86, 345-357 (1999); Hallahan et al., *Radiat. Res.*, 129, 345-350 (1992); Zhang et al., *J. Neurooncol.*, 15, 1-7 (1993); Guo et al., *Int. J. Radiat. Biol.*, 82, 97-109 (2006); Bucher and Britten, *Br. J. Cancer*, 98, 523-528 (2008); Laredo et al., *Blood*, 84, 229-237 (1994); Luo et al., *Neoplasia*, 3, 411-419 (2001); Wang et al., *Yao Xue Xue Bao*, 31, 411-415 (1996); Chen et al., *J. Natl. Cancer Inst.*, 92, 1999-2008 (2000); and Hirose et al., *Cancer Res.*, 61, 5843-5849 (2001)) through several claimed mechanisms including abrogation of a G2 checkpoint response. The mechanism whereby staurosporine treatment affords protection from DNA damaging agents in some cultured cell types is unclear, with a few possible mechanisms suggested including inhibition of protein kinase C or decreasing CDK4 protein levels. See Chen et al., *J. Natl. Cancer Inst.*, 92, 1999-2008 (2000); and Ojeda et al., *Int. J. Radiat. Biol.*, 61, 663-667 (1992). No effect of staurosporine has been shown on hematopoietic progenitors, nor has staurosporine use well after exposure to DNA damaging agents been shown to afford protection. Further, staurosporine's non-selective kinase inhibition has led to significant toxicities independent of its effects on the cell cycle (e.g. hyperglycemia) after in vivo administration to mammals and these toxicities have precluded its clinical use.

Accordingly, there is an ongoing need for practical methods to protect subjects who are scheduled to incur, are at risk for incurring, or who have already incurred, exposure to DNA damaging agents and/or events and methods of augmenting the efficacy of toxicity reducing agents. In addition, an ongoing need exists for methods and compositions for treating autoimmune diseases by blocking the proliferation of immune cells.

SUMMARY

In some embodiments, the presently disclosed subject matter provides a method of increasing the efficacy of a toxicity reducing agent in a subject in need of treatment thereof, the method comprising: providing a subject that has been exposed to, is being exposed to, or is at risk of being exposed to a DNA damaging agent or event; administering to said subject a toxicity reducing agent; and administering to said subject a pharmaceutically effective amount of a compound that selectively inhibits cyclin dependent kinase 4 (CDK4) and/or cyclin dependent kinase 6 (CDK6).

In some embodiments, the toxicity reducing agent is a chemotherapy toxicity reducing agent. In some embodiments, the toxicity reducing agent is a radiation toxicity reducing agent.

In some embodiments, the toxicity reducing agent comprises one or more agents selected from the group comprising, but not limited to, a growth factor, a granulocyte colony-stimulating factor (G-CSF), a pegylated G-CSF, granulocyte-macrophage colony stimulating factor (GM-CSF), thrombopoietin, erythropoietin, pegylated erythropoietin, interleukin (IL)-12, steel factor, a keratinocyte growth factor, or a derivative thereof.

In some embodiments, the compound that selectively inhibits CDK4 and/or CDK6 induces pharmacologic quiescence in one or more cells within the subject. In some embodiments, the one or more cells are each selected from the group comprising a hematologic cell, a hematologic stem cell, and a hematologic precursor cell.

In some embodiments, the compound that selectively inhibits CDK4 and/or CDK6 is administered to the subject prior to the subject being exposed to the DNA damaging agent or event, at the same time the subject is being exposed to the DNA damaging agent or event, or after exposure of the subject to the DNA damaging agent or event. In some embodiments, the compound that selectively inhibits CDK4 and/or CDK6 is administered to the subject between about 24 and about 48 hours after exposure of the subject to the DNA damaging agent or event.

In some embodiments, the presently disclosed subject matter provides a method of mitigating DNA damage in a non-hematologic cell or tissue in a subject in need of treatment thereof prior to or following exposure of the cell or tissue to a DNA damaging agent or event, the method comprising administering to the subject a pharmaceutically effective amount of a compound that selectively inhibits CDK4 and/or CDK6. In some embodiments, the non-hematologic cell or tissue is comprises a cell or tissue from one of the group comprising kidney, gut, heart, liver, brain, thyroid, skin, intestinal mucosa, auditory system, lung, bladder, ovaries, uterus, testicles, adrenals, gallbladder, pancreas, pancreatic islets, stomach, blood vessels, bone, and combinations thereof.

In some embodiments, the presently disclosed subject matter provides a method of reducing or inhibiting memory T cell proliferation in a subject in need of treatment thereof, the method comprising administering to the subject a pharmaceutically effective amount of a compound that selectively inhibits CDK4 and/or CDK6 to the subject.

In some embodiments, the subject has or is at risk of developing an autoimmune or allergic disease. In some embodiments, the autoimmune or allergic disease is selected from the group comprising systemic lupus erythematosus (SLE), rheumatoid arthritis (RA), autoimmune arthritis, scleroderma, hemolytic anemia, autoimmune aplastic anemia, autoimmune granulocytopenia, type I diabetes, thrombotic thrombocytopenic purpura (TTP), psoriasis, inflammatory bowel disease, Crohn's disease, ulcerative colitis, contact dermatitis, polymyalgia rheumatica, uveitis, immune pneumonitis, autoimmune hepatitis, immune nephritis, immune glomerulonephritis, multiple sclerosis, autoimmune neuropathy, vitiligo, discoid lupus, Wegener's Granulomatosis, Henoch-Schoelein Purpura, sclerosing cholangitis, autoimmune thyroiditis, autoimmune myocarditis, autoimmune vasculitis, dermatomyositis, extrinsic and intrinsic reactive airways disease (asthma), myasthenia gravis, autoimmune ovarian failure, pernicious anemia, Addison's disease, autoimmune hypoparathyroidism and other syndromes of inappropriate cellular immune response.

In some embodiments, the presently disclosed subject matter provides a method of reducing or inhibiting B cell progenitor proliferation in a subject in need of treatment thereof, the method comprising administering to the subject a pharmaceutically effective amount of a compound that selectively inhibits CDK4 and/or CDK6 to the subject.

In some embodiments, the subject has or is at risk of developing an autoimmune or allergic disease. In some embodiments, the autoimmune or allergic disease is selected from the group consisting of systemic lupus erythematosus (SLE), rheumatoid arthritis (RA), scleroderma, hemolytic anemia, idiopathic thrombocytopenic purpura (ITP), acquired inhibitors in hemophilia, thrombotic thrombocytopenic purpura (TTP), Goodpasture's syndrome, cold and warm agglutin diseases, cryoglobulinemia, and syndromes of inappropriate antibody production.

In some embodiments, the presently disclosed subject matter provides a method for mitigating an autoimmune or allergic disease in a subject in need of treatment thereof, the method comprising administering to the subject a pharmaceutically effective amount of a compound that selectively inhibits CDK4 and/or CDK6, wherein said compound reduces or inhibits memory T cell proliferation, B cell progenitor proliferation, or both memory T cell proliferation and B cell progenitor proliferation.

In some embodiments, the autoimmune or allergic disease is selected from the group comprising systemic lupus erythematosus (SLE), rheumatoid arthritis (RA), autoimmune arthritis, scleroderma, hemolytic anemia, autoimmune aplastic anemia, autoimmune granulocytopenia, type I diabetes, thrombotic thrombocytopenic purpura (TTP), psoriasis, inflammatory bowel disease, Crohn's disease, ulcerative colitis, contact dermatitis, polymyalgia rheumatica, uveitis, immune pneumonitis, autoimmune hepatitis, immune nephritis, immune glomerulonephritis, multiple sclerosis, autoimmune neuropathy, vitiligo, discoid lupus, Wegener's Granulomatosis, Henoch-Schoelein Purpura, sclerosing cholangitis, autoimmune thyroiditis, autoimmune myocarditis, autoimmune vasculitis, dermatomyositis, extrinsic and intrinsic reactive airways disease (asthma), myasthenia gravis, autoimmune ovarian failure, pernicious anemia, Addison's disease, autoimmune hypoparathyroidism other syndromes of an inappropriate cellular immune response, Goodpasture's syndrome, cold and warm agglutin diseases, cryoglobulinemia, and syndromes of inappropriate antibody production.

In some embodiments, the presently disclosed subject matter provides a method of treating cancer in a subject in need of treatment thereof, wherein the cancer is characterized by an increased level of cyclin dependent kinase 2 (CDK2) activity or by reduced expression of retinoblastoma tumor suppressor protein or a retinoblastoma family member protein, the method comprising administering to the subject a pharmaceutically effective amount of a compound that selectively inhibits CDK4 and/or CDK6.

In some embodiments, the compound that selectively inhibits CDK4 and/or CDK6 does not induce pharmacologic quiescence in cancer cells. In some embodiments, the compound that selectively inhibits CDK4 and/or CDK6 increases the sensitivity of cancer cells to DNA damaging agents. In some embodiments, the increase in sensitivity increases cancer cell death.

In some embodiments, the increased level of CDK2 activity is associated with MYC protooncogene amplification or overexpression. In some embodiments, the increased level of CDK2 activity is associated with overexpression of Cyclin E1, Cyclin E2, or Cyclin A.

In some embodiments, administration of the compound that selectively inhibits CDK4 and/or CDK6 mitigates hematologic toxicities associated with exposure to a DNA damaging agent or event. In some embodiments, administration of the compound that selectively inhibits CDK4 and/or CDK6 mitigates long-term toxicities such as secondary malignancy and myelodysplasia associated with exposure to a DNA damaging agent or event.

In some embodiments, the compound that selectively inhibits CDK4 and/or CDK6 is administered to the subject prior to the subject being exposed to the DNA damaging agent or event, at the same time the subject is being exposed to the DNA damaging agent or event, or after exposure of the subject to the DNA damaging agent or event. In some embodiments, the compound that selectively inhibits CDK4 and/or CDK6 is administered to the subject between about 24 and about 48 hours after exposure of the subject to the DNA damaging agent or event.

In some embodiments, the presently disclosed subject matter provides a method of mitigating chemotherapy-induced or radiotherapy-induced secondary malignancies of hematological or non-hematological origin in a subject, the method comprising administering to the subject a pharmacologically effective amount of a compound that selectively inhibits CDK4 and/or CDK6. In some embodiments, the compound that selectively inhibits CDK4 and/or CDK6 is administered to the subject prior to or during the same time period that the subject is undergoing chemotherapy or radiation-based therapy to treat a primary malignancy.

It is an object of the presently disclosed subject matter to provide methods of protecting healthy cells in subjects from the effects of DNA damaging agents and of treating certain conditions by administering to the subject an effective amount of a selective CDK4/6 inhibitor compound.

An object of the presently disclosed subject matter having been stated hereinabove, and which is achieved in whole or in part by the presently disclosed subject matter, other objects will become evident as the description proceeds

BRIEF DESCRIPTION OF THE DRAWINGS

FIG. 17A: Preferential inhibition of memory T cell and TD cell proliferation in CD4+ T cells. Central memory (CCR7−CD45RA−), effector memory (CCR7+CD45RA+), Naïve (CCR7+CD45RA+) and terminal differentiated T cells (CCR7−CD45RA+) are shown. Representative flow dot plots with indicated treatment: vehicle (DMSO), PD0332991 or 2BrIC.

FIG. 17B: Preferential inhibition of memory T cell and TD cell proliferation in CD4+ T cells. Graph showing the ratio of memory T cells/Naïve T cells for data shown in FIG. 17A. The memory and terminal differentiated T cell fractions are reduced after CDK4/6 inhibition. L4D=2BrIC. Error bars show +/−SEM.

FIG. 17C: Preferential inhibition of memory T cell and TD cell proliferation in CD4+ T cells. Graph quantifies the % of T cells for data shown in FIG. 17A. The memory and terminal differentiated T cell fractions are reduced after CDK4/6 inhibition. Error bars show +/−SEM.

DETAILED DESCRIPTION

Figure 1:
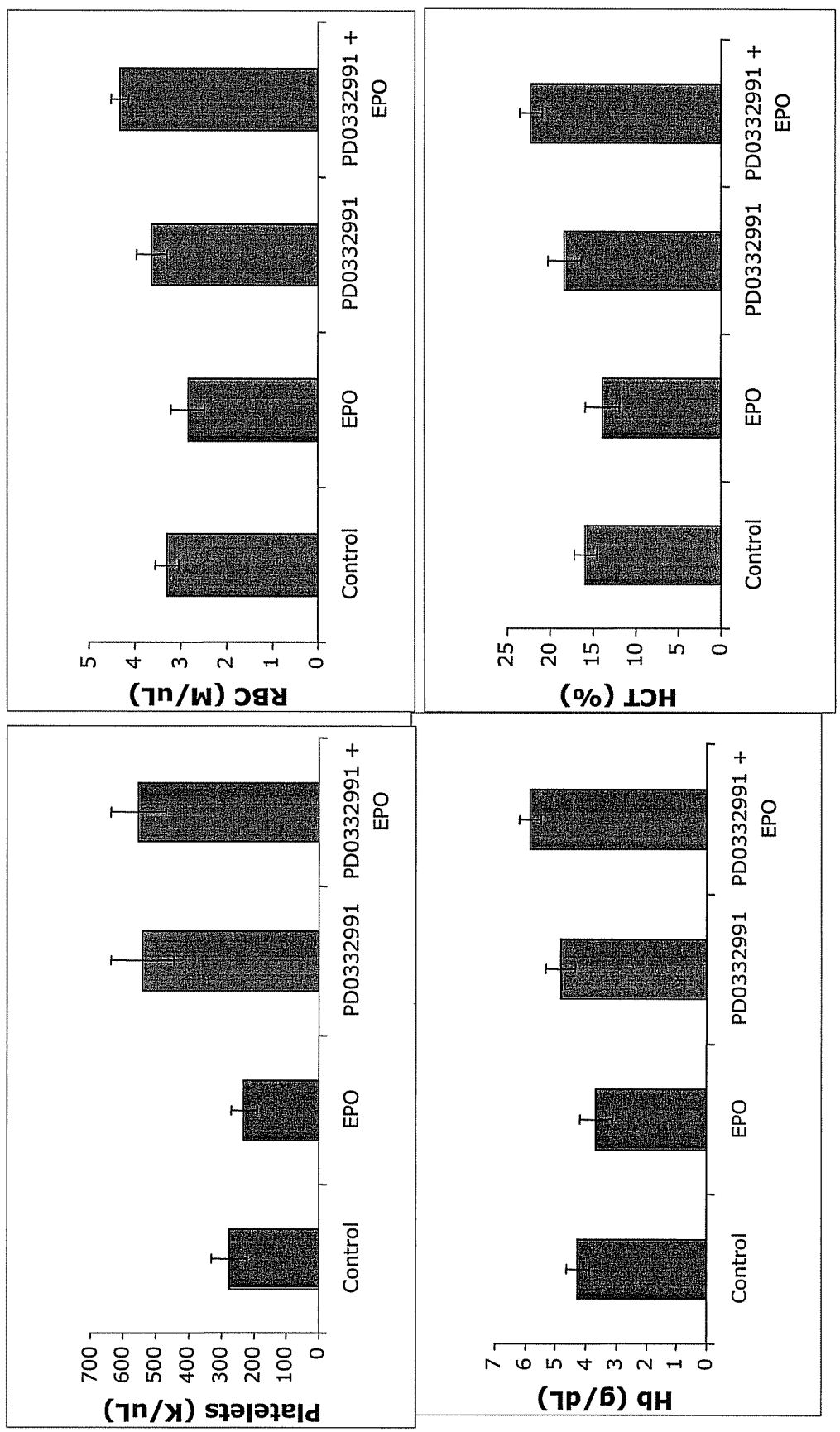
FIG. 1: CDK4/6 inhibition potentiates the efficacy of erythropoietin-mediated recovery of the erythroid cell lineage following DNA damage. Cohorts (8 mice per cohort) of irradiated (6.5 Gy) wild type mice (FVB/n) are given placebo, erythropoietin (EPO), a CDK4/6 inhibitor (PD0332991), or a combination of CDK4/6 inhibitor and EPO (PD0332991+EPO). Serial blood draws are performed at day 17 after treatment and complete blood counts assessed to determine the number of red blood cells, various leukocytes subpopulations, and platelets. The effect of treatment on platelets is shown in the panel on the upper left, red blood cells (RBC) in the panel on the upper right, hemoglobin (Hb) in the panel on the lower left, and hematocrit (HCT) in the panel on the lower right. Error bars represent +/−SEM.

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

Throughout the specification and claims, a given chemical formula or name shall encompass all active optical and stereoisomers, as well as racemic mixtures where such isomers and mixtures exist.

I. Definitions

While the following terms are believed to be well understood by one of ordinary skill in the art, the following definitions are set forth to facilitate explanation of the presently disclosed subject matter.

Following long-standing patent law convention, the terms "a", "an", and "the" refer to "one or more" when used in this application, including the claims. Thus, for example, reference to "a compound" or "a cell" includes a plurality of such compounds or cells, and so forth.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

The term "and/or" when used in describing two items or conditions, e.g., CDK4 and/or CDK6, refers to situations where both items or conditions are present or applicable and to situations wherein only one of the items or conditions is present or applicable. Thus, a CDK4 and/or CDK6 inhibitor can be a compound that inhibits both CDK4 and CDK6, a compound that inhibits only CDK4, or a compound that only inhibits CDK6.

By "healthy cell" or "normal cell" is meant any cell in a subject that does not display characteristics, symptoms and/or markers of a disease (such as, but not limited to, cancer or another proliferative disease). In some embodiments, the healthy cell is a stem cell. In some embodiments, the healthy cell is a hematopoietic stem or progenitor cell (HSPC). Progenitor cells include, but are not limited to, long term hematopoietic stem cells (LT-HSCs), short term hematopoietic stem cells (ST-HSCs), multipotent progenitors (MPPs), common myeloid progenitors (CMPs), common lymphoid progenitors (CLPs), granulocyte-monocyte progenitors (GMPs), and megakaryocyte-erythroid progenitors (MEPs). Progenitor cells can also include mature effector cells derived from hematopoietic stem cells, including, but not limited to, erythrocytes, platelets, granulocytes, macrophages, T-cells, and B-cells.

In some embodiments, the healthy cell is a cell in a non-hematopoietic tissue, such as, but not limited to, the liver, kidney, pancreas, brain, lung, adrenals, intestine, gut, stomach, skin, auditory system, bone, bladder, ovaries, uterus, testicles, gallbladder, thyroid, heart, pancreatic islets, blood vessels, and the like.

By "DNA damaging agent or event" is meant herein both DNA damaging chemical compounds, and other effectors of DNA damage (e.g., ionizing radiation). Thus, a DNA damaging agent or event can include chemotherapeutic and radiation treatment provided for a particular purpose, such as but not limited to a medical purpose (e.g., to treat cancer or other diseases related to overproliferation of cells). DNA damaging agents and events can also relate to accidental exposure to DNA damaging chemical compounds and/or other agents that can take place, for example, due to unexpected environmental exposure (e.g., in the workplace or in another environment due to, for example, a chemical spill, improper disposal or other improper handling of chemical or radiological waste, failure of safety measures and/or personal protective gear during the use of DNA damaging chemicals or radiation, terrorist attack, warfare, or industrial and/or nuclear power plant accident).

As used herein the term "ionizing radiation" refers to radiation of sufficient energy that, when absorbed by cells and tissues, typically induces formation of reactive oxygen species and DNA damage. Ionizing radiation can include X-rays, gamma rays, and particle bombardment (e.g., neutron beam, electron beam, protons, mesons, and others), and is used for purposes including, but not limited to, medical testing and treatment, scientific purposes, industrial testing, manufacturing, and sterilization, and weapons and weapons development. Radiation is generally measured in units of absorbed dose, such as the rad or gray (Gy), or in units of dose equivalence, such as rem or sievert (Sv).

By "at risk of being exposed to a DNA damaging agent or event" is meant a subject scheduled for (such as by scheduled radiotherapy or chemotherapy sessions) exposure to a DNA damaging agent or event in the future or a subject having a chance of being exposed to a DNA damaging agent or event inadvertently in the future. Inadvertent exposure includes accidental or unplanned environmental or occupational exposure (e.g., terrorist attack with a radiological or chemical weapon, a chemical spill or radiation leak, or exposure to a radiological or chemical weapon on the battlefield).

The term "cancer" as used herein refers to diseases caused by uncontrolled cell division and the ability of cells to metastasize, or to establish new growth in additional sites. The terms "malignancy", "neoplasm", "tumor" and variations thereof refer to cancerous cells or groups of cancerous cells.

Specific types of cancer include, but are not limited to, skin cancers, connective tissue cancers, adipose cancers, breast cancers, lung cancers, stomach cancers, pancreatic cancers, ovarian cancers, cervical cancers, uterine cancers, anogenital cancers, kidney cancers, bladder cancers, colon cancers, prostate cancers, head and neck cancers, brain cancers, central nervous system (CNS) cancers, retinal cancer, blood, and lymphoid cancers.

In some embodiments, the term cancer refers to a cancer that can be characterized by (e.g., that has cells that exhibit) an increased level of CDK2 activity or by reduced expression of retinoblastoma tumor suppressor protein or retinoblastoma family member protein(s), such as, but not limited to p107 and p130. The increased level of CDK2 activity or reduced expression of retinoblastoma tumor suppressor protein or retinoblastoma family member protein(s) can be increased or reduced, for example, compared to normal cells. In some embodiments, the increased level of CDK2 activity can be associated with (e.g., can result from or be observed along with) MYC protooncogene amplification or overexpression. In some embodiments, the increased level of CDK2 activity can be associated with overexpression of Cyclin E1, Cyclin E2, or Cyclin A.

As used herein the term "chemotherapy" refers to treatment with a cytotoxic compound (such as but not limited to a DNA damaging compound) to reduce or eliminate the growth or proliferation of undesirable cells, such as, but not limited to, cancer cells. Thus, as used herein, "chemotherapeutic compound" refers to a cytotoxic compound used to treat cancer. The cytotoxic effect of the compound can be, but is not required to be, the result of one or more of nucleic acid intercalation or binding, DNA or RNA alkylation, inhibition of RNA or DNA synthesis, the inhibition of another nucleic acid-related activity (e.g., protein synthesis), or any other cytotoxic effect.

Thus, a "cytotoxic compound" can be any one or any combination of compounds also described as "antineoplastic" agents or "chemotherapeutic agents." Such compounds include, but are not limited to, DNA damaging compounds and other chemicals that can kill cells. "DNA damaging compounds" include, but are not limited to, alkylating agents, DNA intercalators, protein synthesis inhibitors, inhibitors of DNA or RNA synthesis, DNA base analogs, topoisomerase inhibitors, and telomerase inhibitors or telomeric DNA binding compounds. For example, alkylating agents include alkyl sulfonates, such as busulfan, improsulfan, and piposulfan; aziridines, such as a benzodizepa, carboquone, meturedepa, and uredepa; ethylenimines and methylmelamines, such as altretamine, triethylenemelamine, triethylenephosphoramide, triethylenethiophosphoramide, and trimethylolmelamine; nitrogen mustards such as chlorambucil, chlornaphazine, cyclophosphamide, estramustine, iphosphamide, mechlorethamine, mechlorethamine oxide hydrochloride, melphalan, novembichine, phenesterine, prednimustine, trofosfamide, and uracil mustard; and nitroso ureas, such as carmustine, chlorozotocin, fotemustine, lomustine, nimustine, and ranimustine.

Antibiotics used in the treatment of cancer include dactinomycin, daunorubicin, doxorubicin, idarubicin, bleomycin sulfate, mytomycin, plicamycin, and streptozocin. Chemotherapeutic antimetabolites include mercaptopurine, thioguanine, cladribine, fludarabine phosphate, fluorouracil (5-FU), floxuridine, cytarabine, pentostatin, methotrexate, and azathioprine, acyclovir, adenine β-1-D-arabinoside, amethopterin, aminopterin, 2-aminopurine, aphidicolin, 8-azaguanine, azaserine, 6-azauracil, 2'-azido-2'-deoxynucleosides, 5-bromodeoxycytidine, cytosine β-1-D-arabinoside, diazooxynorleucine, dideoxynucleosides, 5-fluorodeoxycytidine, 5-fluorodeoxyuridine, and hydroxyurea.

Chemotherapeutic protein synthesis inhibitors include abrin, aurintricarboxylic acid, chloramphenicol, colicin E3, cycloheximide, diphtheria toxin, edeine A, emetine, erythromycin, ethionine, fluoride, 5-fluorotryptophan, fusidic acid, guanylyl methylene diphosphonate and guanylyl imidodiphosphate, kanamycin, kasugamycin, kirromycin, and O-methyl threonine. Additional protein synthesis inhibitors include modeccin, neomycin, norvaline, pactamycin, paromomycine, puromycin, ricin, shiga toxin, showdomycin, sparsomycin, spectinomycin, streptomycin, tetracycline, thiostrepton, and trimethoprim. Inhibitors of DNA synthesis, include alkylating agents such as dimethyl sulfate, mitomycin C, nitrogen and sulfur mustards; intercalating agents, such as acridine dyes, actinomycins, adriamycin, anthracenes, benzopyrene, ethidium bromide, propidium diiodide-intertwining; and other agents, such as distamycin and netropsin. Topoisomerase inhibitors, such as coumermycin, nalidixic acid, novobiocin, and oxolinic acid; inhibitors of cell division, including colcemide, colchicine, vinblastine, and vincristine; and RNA synthesis inhibitors including actinomycin D, α-amanitine and other fungal amatoxins, cordycepin (3'-deoxyadenosine), dichlororibofuranosyl benzimidazole, rifampicine, streptovaricin, and streptolydigin also can be used as the DNA damaging compound Thus, current chemotherapeutic compounds whose toxic effects can be mitigated by the presently disclosed selective CDK4/6 inhibitors include, but are not limited to, adrimycin, 5-fluorouracil (5FU), etoposide, camptothecin, actinomycin-D, mitomycin, cisplatin, hydrogen peroxide, carboplatin, procarbazine, mechlorethamine, cyclophosphamide, ifosfamide, melphalan, chlorambucil, bisulfan, nitrosurea, dactinomycin, daunorubicin, doxorubicin, bleomycin, plicomycin, tamoxifen, taxol, transplatinum, vinblastin, and methotrexate, and the like.

By "toxicity reducing agent" is meant a compound or other agent that is used to reduce the cytotoxic effects of an agent or event, such as but not limited to a DNA damaging agent or event. In some embodiments, the toxicity reducing agent is a compound that is other than a compound that selectively inhibits one or more cyclin dependent kinase(s). The toxicity reducing agent is an agent that can prevent or reduce DNA damage in a cell, tissue or subject treated with or otherwise exposed to a DNA damaging agent or event. The prevention or reducing of DNA damage effected by the toxicity reducing agent can affect certain cells (e.g., certain healthy) in a subject while not providing any effect in other cells (e.g., in diseased and/or tumor cells) in a subject. Thus, the use of the toxicity reducing agent can protect certain cells in a subject in order to allow more frequent or higher dose use of DNA damaging agents during a disease treatment regime. In some embodiments, the toxicity reducing agent reduces undesired cytotoxicity due to the use of a chemotherapeutic agent. In some embodiments, the toxicity reducing agent can reduce undesired cytotoxicity resulting from radiation.

In some embodiments, the toxicity reducing agent is a growth factor or other naturally occurring compound, or a derivative thereof. In some embodiments, the toxicity reducing agent is selected from the group comprising, but not limited to a growth factor, a granulocyte colony-stimulating factor (G-CSF), a pegylated G-CSF, granulocyte-macrophage colony stimulating factor (GM-CSF), thrombopoietin, erythropoietin, pegylated erythropoietin, interleukin (IL)-12, steel factor, a keratinocyte growth factor, or to derivatives thereof (e.g., chemically modified compounds having structures based upon one of the foregoing named toxicity reducing agents, such as alkylated or esterified derivatives).

"Increasing the efficacy of a toxicity reducing agent" refers to the ability of a selective CDK4 and/or CDK6 inhibitor to increase the efficacy of a toxicity reducing agent. Thus, the term can refer to beneficial use of a combination of a toxicity reducing agent and a selective CDK4 and/or CDK6 inhibitor. For example, use of the combination can result in higher tolerance of the subject to a given amount or to a given frequency of administration of a DNA damaging agent or event that the tolerance the subject would have had when given the toxicity reducing agent (or selective CDK4 and/or CDK6 inhibitor) alone. The use of the combination can provide a higher level of protection from a side effect caused by a DNA damaging event (such as but not limited to a greater reduction in myelosuppression or a lower probability of occurrence of a secondary malignancy). The use of the combination can also provide protection from a wider range of side effects due to exposure to the DNA damaging agent or event and/or protection in a wider variety of types of cells and/or tissues in the subject. For instance, in some embodiments, a selective CDK4 and/or CDK6 inhibitor can provide synergistic effects when used in combination with a growth factor to rescue and support the various hematopoietic populations from a DNA damaging agent or event.

By "pharmaceutically effect amount of a compound" is meant an amount effective to provide a beneficial result in the subject. For example, it can be the amount effective to reduce or eliminate the toxicity associated with the DNA damaging agent or event (e.g., the chemotherapy or other exposure to a cytotoxic compound in healthy HSPCs in the subject, or the IR). In some embodiments, the effective amount is the amount required to temporarily (e.g., for a few hours or days) inhibit the proliferation of hematopoietic stem cells (i.e., to induce a quiescent state in hematopoietic stem cells) in the subject.

In some embodiments, the compound that selectively inhibits CDK4 and/or CDK6 is free of off-target effects. "Free of" can refer to a selective CDK4/6 inhibitor compound not having an undesired or off-target effect, particularly when used in vivo or assessed via a cell-based assay. Thus, "free of" can refer to a selective CDK4/6 inhibitor not having off-target effects such as, but not limited to, long term toxicity, anti-oxidant effects, estrogenic effects, tyrosine kinase inhibitory effects, inhibitory effects on CDKs other than CDK4/6; and/or cell cycle arrest in CDK4/6-independent cells.

A selective CDK4/6 inhibitor that is "substantially free" of off-target effects is a CDK4/6 inhibitor that can have some minor off-target effects that do not interfere with the inhibitor's ability to provide protection from cytotoxic compounds in CDK4/6-dependent cells. For example, a CDK4/6 inhibitor that is "substantially free" of off-target effects can have some minor inhibitory effects on other CDKs (e.g., $IC_{50}$s for CDK1 or CDK2 that are >0.5 µM; >1.0 µM, or >5.0 µM), so long as the inhibitor provides selective G1 arrest in CDK4/6-dependent cells.

By "reduced" or "prevented" or grammatical variations thereof means, respectively, lessening the effects or keeping the effects from occurring completely. "Mitigating" can refer to reducing and/or preventing.

By "pharmacologic quiescence" is meant a temporary arrest of cell cycling.

By "at risk of developing an autoimmune disease" refers to a subject that is suspected of having a likelihood of developing an autoimmune disease for reasons including, but not limited to, for example, due to having one or more genetic marker associated with an autoimmune disease, having a family history of autoimmune disease, and/or having had exposure to an environmental agent that is suspected of triggering the onset of an autoimmune disease. The term can also apply to subjects that have been diagnosed with an autoimmune disease previously but who are in remission and/or are currently symptom-free.

In some embodiments, the subject treated in the presently disclosed subject matter is desirably a human subject, although it is to be understood the methods described herein are effective with respect to all vertebrate species (e.g., mammals, birds, etc.), which are intended to be included in the term "subject."

More particularly, provided herein is the treatment of mammals, such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Thus, embodiments of the methods described herein include the treatment of livestock, including, but not limited to, domesticated swine (pigs and hogs), ruminants, horses, and the like.

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl)hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic moiety that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, carbonyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

The term "heteroaryl" refers to aryl groups wherein at least one atom of the backbone of the aromatic ring or rings is an atom other than carbon. Thus, heteroaryl groups have one or more non-carbon atoms selected from the group including, but not limited to, nitrogen, oxygen, and sulfur.

As used herein, the term "acyl" refers to an organic carboxylic acid group wherein the —OH of the carboxyl group has been replaced with another substituent (i.e., as represented by RCO—, wherein R is an alkyl or an aryl group as defined herein). As such, the term "acyl" specifically includes arylacyl groups, such as an acetylfuran and a phenacyl group. Specific examples of acyl groups include acetyl and benzoyl.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

The terms "heterocycle" or "heterocyclic" refer to cycloalkyl groups (i.e., non-aromatic, cyclic groups as described hereinabove) wherein one or more of the backbone carbon atoms of a cyclic ring is replaced by a heteroatom (e.g., nitrogen, sulfur, or oxygen). Examples of heterocycles include, but are not limited to, tetrahydrofuran, tetrahydropyran, morpholine, dioxane, piperidine, piperazine, and pyrrolidine.

"Alkoxyl" or "alkoxy" refers to an alkyl-O— group wherein alkyl is as previously described. The term "alkoxyl" as used herein can refer to, for example, methoxyl, ethoxyl, propoxyl, isopropoxyl, butoxyl, t-butoxyl, and pentoxyl. The term "oxyalkyl" can be used interchangeably with "alkoxyl".

"Aryloxyl" or "aryloxy" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" or "aralkyloxy" refers to an aralkyl-O— group wherein the aralkyl group is as previously described. An exemplary aralkyloxyl group is benzyloxyl.

The term "amino" refers to the —NR'R" group, wherein R' and R" are each independently selected from the group including H and substituted and unsubstituted alkyl, cycloalkyl, heterocycle, aralkyl, aryl, and heteroaryl. In some embodiments, the amino group is —NH$_2$. "Aminoalkyl" and "aminoaryl" refer to the —NR'R" group, wherein R' is as defined hereinabove for amino and R" is substituted or unsubstituted alkyl or aryl, respectively.

"Acylamino" refers to an acyl-NH— group wherein acyl is as previously described.

The term "carbonyl" refers to the —(C=O)— or a double bonded oxygen substituent attached to a carbon atom of a previously named parent group.

The term "carboxyl" refers to the —COOH group.

The terms "halo", "halide", or "halogen" as used herein refer to fluoro, chloro, bromo, and iodo groups.

The terms "hydroxyl" and "hydroxy" refer to the —OH group.

The term "oxo" refers to a compound described previously herein wherein a carbon atom is replaced by an oxygen atom.

The term "cyano" refers to the —CN group.

The term "nitro" refers to the —NO$_2$ group.

The term "thio" refers to a compound described previously herein wherein a carbon or oxygen atom is replaced by a sulfur atom.

II. Compounds and Methods of Protection from DNA Damaging Agents or Events

Tissue-specific stem cells and subsets of other resident proliferating cells are capable of self-renewal, meaning that they are capable of replacing themselves throughout the adult mammalian lifespan through regulated replication. Additionally, stem cells divide asymmetrically to produce "progeny" or "progenitor" cells that in turn produce various components of a given organ. For example, in the hematopoietic system, the hematopoietic stem cells give rise to progenitor cells which in turn give rise to all the differentiated components of blood (e.g., white blood cells, red blood cells, lymphocytes and platelets).

The presently disclosed subject matter relates, in part, to particular biochemical requirements of early hematopoietic stem/progenitor cells (HSPC) and other proliferating cells in the adult mammal. In particular, it has been found that certain specific proliferating cells, such as HSPC, require the enzymatic activity of the proliferative kinases cyclin-dependent kinase 4 (CDK4) and/or cyclin-dependent kinase 6 (CDK6) for cellular replication. In contrast, the vast majority of proliferating cells in adult mammals do not require the activity of CDK4 and/or CDK6 (i.e., CDK4/6). These differentiated cells can proliferate in the absence of CDK4/6 activity by using other proliferative kinases, such as cyclin-dependent kinase 2 (CDK2) or cyclin-dependent kinase 1 (CDK1). Therefore, it is believed that treatment of mammals with a selective CDK4/6 inhibitor can lead to inhibition of proliferation (i.e., pharmacologic quiescence) in very restricted cellular compartments, such as HSPC. For instance, transient treatment (such as, but not limited to, over a less than 48, 24, 20, 16, 12, 10, 8, 6, 4, 2, or 1 hour period) with PD 0332991, a selective CDK4/6 inhibitor, renders hematopoietic stem cells and their associated hematopoietic progenitor cells quiescent. Cells that are quiescent are believed to be more resistant to the cytotoxic effects of DNA damaging agents or events than are proliferating cells.

Accordingly, the presently disclosed subject matter provides, in some embodiments, a methods of protecting mammals from the acute and chronic toxic effects of chemotherapeutic compounds by forcing hematopoietic stem and progenitor cells (HSPCs) into a quiescent state by transient (such as, but not limited to, over a less than 48, 24, 20, 16, 12, 10, 8, 6, 4, 2, or 1 hour period) treatment with an non-toxic, selective CDK4/6 inhibitor (such as but not limited to, an orally available, non-toxic CDK4/6 inhibitor). During the period of quiescence, the subject's HSPC are more resistant to certain effects of the chemotherapeutic compound. The HSPCs recover from this period of transient quiescence, and then function normally after treatment with the inhibitor is stopped. Thus, treatment with selective CDK4/6 inhibitors can provide marked bone marrow protection and can lead to a more rapid recovery of peripheral blood cell counts (hematocrit, platelets, lymphocytes, and myeloid cells) after chemotherapy and/or radiotherapy.

U.S. Pat. No. 6,369,086 to Davis et al. (hereinafter "the '086 patent") appears to describe that selective CDK inhibitors can be useful in limiting the toxicity of cytotoxic agents and can be used to protect from chemotherapy-induced alopecia. In particular, the '086 patent describes oxindole compounds as specific CDK2 inhibitors. A related journal reference (see Davis et al., *Science*, 291, 134-137 (2001))

appears to describe that the inhibition of CDK2 produces cell cycle arrest, reducing the sensitivity of the epithelium to cell cycle-active antitumor agents and can prevent chemotherapy-induced alopecia. However, this journal reference was later retracted due to the irreproducibility of the results. In contrast to these purported protective effects of selective CDK2 inhibitors, for which a question is raised by the retraction of the journal article, the presently disclosed subject matter relates in some embodiments to protection of HSPCs and protection from hematological toxicity.

The ability to protect stem/progenitor cells is desirable both in the treatment of cancer and in mitigating the effects of accidental exposure to or overdose with cytotoxic chemicals, radiation, or other DNA damaging agents. The protective effects of the selective CDK4/6 inhibitors can be provided to the subject via pretreatment with the inhibitor (i.e., prior CDK4/6 inhibitor treatment of a subject scheduled to be treated with or at risk of exposure to a DNA damaging agent), concomitant treatment with the CDK4/6 inhibitor and the DNA damaging agent, or post-treatment with the CDK4/6 inhibitor (i.e., treatment with the CDK4/6 inhibitor following exposure to the DNA damaging agent). Thus, in some embodiments, the presently disclosed methods relates to the use of selective CDK4/6 inhibitory compounds to provide protection to subjects undergoing or about to undergo treatment with chemotherapeutic compounds or radiation, and to protect subjects from other exposure to cytotoxic compounds and/or radiation.

As used herein the term "selective CDK4/6 inhibitor compound" refers to a compound that selectively inhibits at least one of CDK4 and CDK6 or whose predominant mode of action is through inhibition of CDK4 and/or CDK 6. Thus, selective CDK4/6 inhibitors are compounds that generally have a lower 50% inhibitory concentration ($IC_{50}$) for CDK4 and/or CDK6 than for other kinases. In some embodiments, the selective CDK4/6 inhibitor can have an $IC_{50}$ for CDK4 or CDK6 that is at least 2, 3, 4, 5, 6, 7, 8, 9, or 10 times lower than the compound's $IC_{50}$s for other CDKs (e.g., CDK1 and CDK2). In some embodiments, the selective CDK4/6 inhibitor can have an $IC_{50}$ for CDK4 or CDK6 that is at least 20, 30, 40, 50, 60, 70, 80, 90, or 100 times lower than the compound's $IC_{50}$s for other CDKs. In some embodiments, the selective CDK4/6 inhibitor can have an $IC_{50}$ that is more than 100 times or more than 1000 times less than the compound's $IC_{50}$s for other CDKs. In some embodiments, the selective CDK4/6 inhibitor compound is a compound that selectively inhibits both CDK4 and CDK6. In some embodiments, the CDK4/6 inhibitor is not a naturally occurring compound (e.g., an isoflavone). In some embodiments, the CDK4/6 inhibitor is a poor inhibitor (e.g., >1 µM in vitro $IC_{50}$) of one or more tyrosine kinases. In some embodiments, the CDK4/6 inhibitor is a high potency inhibitor of serine and/or theonine kinases. In some embodiments, the CDK4/6 inhibitor is a poor CDK1 inhibitor (e.g., (e.g., >1 µM in vitro $IC_{50}$). In some embodiments, the CDK4/6 inhibitor is characterized by having a 10-fold or 50-fold or 100-fold or greater relative potency for inhibiting CDK4 or CDK6 as compared to CDK1.

In some embodiments, the selective CDK4/6 inhibitor compound is a compound that selectively induces G1 cell cycle arrest in CDK4/6 dependent cells. Thus, when treated with the selective CDK4/6 inhibitor compound according to the presently disclosed methods, the percentage of CDK4/6-dependent cells in the G1 phase increase, while the percentage of CDK4/6-dependent cells in the G2/M phase and S phase decrease. In some embodiments, the selective CDK4/6 inhibitor is a compound that induces substantially pure (i.e., "clean") G1 cell cycle arrest in the CDK4/6-dependent cells (e.g., wherein treatment with the selective CDK4/6 inhibitor induces cell cycle arrest such that the majority of cells are arrested in G1 as defined by standard methods (e.g., propidium iodide staining or others) and with the population of cells in the G2/M and S phases combined being 20%, 15%, 12%, 10%, 8%, 6%, 5%, 4%, 3%, 2%, 1% or less of the total cell population).

While staurosporine, a non-specific kinase inhibitor, has been reported to indirectly induce G1 arrest in some cell types (see Chen et al., *J. Nat. Cancer Inst.*, 92, 1999-2008 (2000)), selective CDK4/6 inhibitors can directly and selectively induce G1 cell cycle arrest in cells, such as specific fractions of HSPCs, to provide chemoprotection and radioprotection with reduced long term toxicity and without the need for prolonged (e.g., 48 hour or longer) treatment with the inhibitor prior to exposure with the DNA damaging agent. In particular, while some nonselective kinase inhibitors can cause G1 arrest in some cell types by decreasing CDK4 protein levels, benefits of the presently disclosed methods are, without being bound to any one theory, believed to be due at least in part to the ability of selective CDK4/6 inhibitors to directly inhibit the kinase activity of CDK4/6 in HSPCs without decreasing their cellular concentration.

In some embodiments, the selective CDK4/6 inhibitor compound is a compound that is substantially free of off target effects, particularly related to inhibition of kinases other than CDK4 and or CDK6. In some embodiments, the selective CDK4/6 inhibitor compound is a poor inhibitor (e.g., >1 µM $IC_{50}$) of CDKs other than CDK4/6 (e.g., CDK 1 and CDK2). In some embodiments, the selective CDK4/6 inhibitor compound does not induce cell cycle arrest in CDK4/6-independent cells. In some embodiments, the selective CDK4/6 inhibitor compound is a poor inhibitor (e.g., >1 µM $IC_{50}$) of tyrosine kinases. Additional, undesirable off-target effects include, but are not limited to, long term toxicity, anti-oxidant effects, and estrogenic effects.

Anti-oxidant effects can be determined by standard assays known in the art. For example, a compound with no significant anti-oxidant effects is a compound that does not significantly scavenge free-radicals, such as oxygen radicals. The anti-oxidant effects of a compound can be compared to a compound with known anti-oxidant activity, such as genistein. Thus, a compound with no significant anti-oxidant activity can be one that has less than about 2, 3, 5, 10, 30, or 100 fold anti-oxidant activity relative to genistein. Estrogenic activities can also be determined via known assays. For instance, a non estrogenic compound is one that does not significantly bind and activate the estrogen receptor. A compound that is substantially free of estrogenic effects can be one that has less than about 2, 3, 5, 10, 20, or 100 fold estrogenic activity relative to a compound with estrogenic activity, e.g., genistein.

Selective CDK4/6 inhibitors that can be used according to the presently disclosed methods include any known small molecule (e.g., <1000 Daltons, <750 Daltons, or less than <500 Daltons), selective CDK4/6 inhibitor, or pharmaceutically acceptable salt thereof. In some embodiments, the inhibitor is a non-naturally occurring compound (i.e., a compound not found in nature). Several classes of chemical compounds have been reported as having CDK4/6 inhibitory ability (e.g., in cell free assays). Selective CDK4/6 inhibitors useful in the presently disclosed methods can include, but are not limited to, pyrido[2,3-d]pyrimidines (e.g., pyrido[2,3-d]pyrimidin-7-ones and 2-amino-6-cyano-pyrido[2,3-d]pyrimidin-4-ones), triaminopyrimidines, aryl[a]pyrrolo[3,4- d]carbazoles, nitrogen-containing heteroaryl-substituted ureas, 5-pyrimidinyl-2-aminothiazoles, benzothiadiazines, acridinethiones, and isoquinolones.

In some embodiments, the pyrido[2,3-d]pyrimidine is a pyrido[2,3-d]pyrimidinone. In some embodiments the pyrido[2,3-d]pyrimidinone is pyrido[2,3-d]pyrimidin-7-one. In some embodiments, the pyrido[2,3-d]pyrimidin-7-one is substituted by an aminoaryl or aminoheteroaryl group. In some embodiments, the pyrido[2,3-d]pyrimidin-7-one is substituted by an aminopyridine group. In some embodiments, the pyrido[2,3-d]pyrimidin-7-one is a 2-(2-pyridinyl) amino pyrido[2,3-d]pyrimidin-7-one. For example, the pyrido[2,3-d]pyrimidin-7-one compound can have a structure of Formula (II) as described in U.S. Patent Publication No. 2007/0179118 to Barvian et al., herein incorporated by reference in its entirety. In some embodiments, the pyrido [2,3-d]pyrimidine compound is 6-acetyl-8-cyclopentyl-5-methyl-2-(5-piperazin-1-yl-pyridin-2-ylamino)-8H-pyrido-[2,3-d]pyrimidin-7-one (i.e., PD 0332991) or a pharmaceutically acceptable salt thereof. See Toogood et al., *J. Med. Chem.*, 2005, 48, 2388-2406.

In some embodiments, the pyrido[2,3-d]pyrimidinone is a 2-amino-6-cyano-pyrido[2,3-d]pyrimidin-4-ones. Selective CDK4/6 inhibitors comprising a 2-amino-6-cyano-pyrido[2, 3-d]pyrimidin-4-one are described, for example, by Tu et al. See Tu et al., *Bioorg. Med. Chem. Lett.*, 2006, 16, 3578-3581.

As used herein, "triaminopyrimidines" are pyrimidine compounds wherein at least three carbons in the pyrimidine ring are substituted by groups having the formula —$NR_1R_2$, wherein $R_1$ and $R_2$ are independently selected from the group consisting of H, alkyl, aralkyl, cycloalkyl, heterocycle, aryl, and heteroaryl. Each $R_1$ and $R_2$ alkyl, aralkyl, cycloalkyl, heterocycle, aryl, and heteroaryl groups can further be substituted by one or more hydroxyl, halo, amino, alkyl, aralkyl, cycloalkyl, heterocyclic, aryl, or heteroaryl groups. In some embodiments, at least one of the amino groups is an alkylamino group having the structure —NHR, wherein R is $C_1$-$C_6$ alkyl. In some embodiments, at least one amino group is a cycloalkylamino group or a hydroxyl-substituted cycloalkylamino group having the formula —NHR wherein R is $C_3$-$C_7$ cycloalkyl, substituted or unsubstituted by a hydroxyl group. In some embodiments, at least one amino group is a heteroaryl-substituted aminoalkyl group, wherein the heteroaryl group can be further substituted with an aryl group substituent.

Aryl[a]pyrrolo[3,4-d]carbazoles include, but are not limited to napthyl[a]pyrrolo[3,4-c]carbazoles, indolo[a]pyrrolo [3,4-c]carbazoles, quinolinyl[a]pyrrolo[3,4-c]carbazoles, and isoquinolinyl[a]pyrrolo[3,4-c]carbazoles. See e.g., Engler et al., *Bioorg. Med. Chem. Lett.*, 2003, 13, 2261-2267; Sanchez-Martinez et al., *Bioorg. Med. Chem. Lett.*, 2003, 13, 3835-3839; Sanchez-Martinez et al., *Bioorg. Med. Chem. Lett.*, 2003, 13, 3841-3846; Zhu et al., *Bioorg. Med. Chem. Lett.*, 2003, 13, 1231-1235; and Zhu et al., *J. Med. Chem.*, 2003, 46, 2027-2030. Suitable aryl[a]pyrrolo[3,4-d] carbazoles are also disclosed in U.S. Patent Publication Nos. 2003/0229026 and 2004/0048915.

Nitrogen-containing heteroaryl-substituted ureas are compounds comprising a urea moiety wherein one of the urea nitrogen atoms is substituted by a nitrogen-containing heteroaryl group. Nitrogen-containing heteroaryl groups include, but are not limited to, five to ten membered aryl groups including at least one nitrogen atom. Thus, nitrogen-containing heteroaryl groups include, for example, pyridine, pyrrole, indole, carbazole, imidazole, thiazole, isoxazole, pyrazole, isothiazole, pyrazine, triazole, tetrazole, pyrimi-dine, pyridazine, purine, quinoline, isoquinoline, quinoxaline, cinnoline, quinazoline, benzimidazole, phthalimide and the like. In some embodiments, the nitrogen-containing heteroaryl group can be substituted by one or more alkyl, cycloalkyl, heterocyclic, aralkyl, aryl, heteroaryl, hydroxyl, halo, carbonyl, carboxyl, nitro, cyano, alkoxyl, or amino group. In some embodiments, the nitrogen-containing heteroaryl substituted urea is a pyrazole-3-yl urea. The pyrazole can be further substituted by a cycloalkyl or heterocyclic group. In some embodiments, the pyrazol-3-yl urea is:

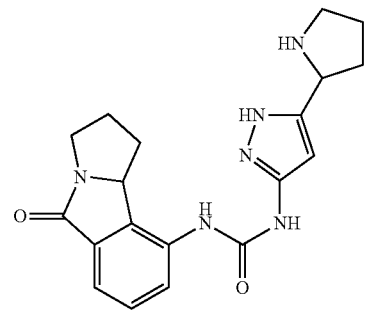

See Ikuta, et al., *J. Biol. Chem.*, 2001, 276, 27548-27554. Additional ureas that can be used according to the presently disclosed subject matter include the biaryl urea compounds of Formula (I) described in U.S. Patent Publication No. 2007/0027147. See also, Honma et al., *J. Med. Chem.*, 2001, 44, 4615-4627; and Honma et al., *J. Med. Chem.*, 2001, 44, 4628-4640.

Suitable 5-pyrimidinyl-2-aminothiazole CDK4/6 inhibitors are described by Shimamura et al. See Shimamura et al., *Bioorg. Med. Chem. Lett.*, 2006, 16, 3751-3754. In some embodiments, the 5-pyrimidinyl-2-aminothiazole has the structure:

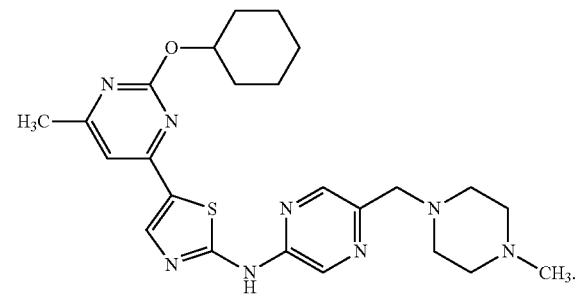 [SMILES: Cc1cc(-c2cnc(Nc3cnc(CN4CCN(C)CC4)cn3)s2)nc(OC2CCCCC2)n1]

Useful benzothiadiazine and acridinethiones compounds include those, for example, disclosed by Kubo et al. See Kubo et al., *Clin. Cancer Res.* 1999, 5, 4279-4286 and in U.S. Patent Publication No. 2004/0006074, herein incorporated by reference in their entirety. In some embodiments, the benzothiadiazine is substituted by one or more halo, haloaryl, or alkyl group. In some embodiments, the benzothiadiazine is selected from the group consisting of 4-(4-fluorobenzylamino)-1,2,3-benzothiadiazine-1,1-dioxide, 3-chloro-4-methyl-4H-benzo[e][1,2,4]thiadiazine-1,1-dioxide, and 3-chloro-4-ethyl-4H-benzo[e][1,2,4]thiadiazine-1, 1-dioxide. In some embodiments, the acridinethione is substituted by one or more amino or alkoxy group. In some embodiments, the acridinethione is selected from the group consisting of 3-amino-10H-acridone-9-thione (3ATA), 9(10H)-acridinethione, 1,4-dimethoxy-10H-acridine-9-thione, and 2,2'-diphenyldiamine-bis-[N,N'-[3-amido-N-methylamino)-10H-acridine-9-thione]].

In some embodiments, the subject of the presently disclosed methods will be a subject who has been exposed to, is being exposed to, or is scheduled to be exposed to, a DNA damaging agent while undergoing therapeutic treatment for a proliferative disorder. Such disorders include cancerous and non-cancer proliferative diseases. For example, the presently disclosed compounds are believed effective in protecting healthy HSPCs during chemotherapeutic treatment of a broad range of tumor types, including but not limited to the following: breast, prostate, ovarian, skin, lung, colorectal, brain (i.e., glioma) and renal.

Ideally, it is preferable that the selective CDK4/6 inhibitor not compromise the efficacy of the DNA damaging agent by itself arresting the growth of the cancer cells. Most cancers appear not to depend on the activities of CDK4/6 for proliferation as they can use the proliferative kinases promiscuously (e.g., can use CDK 1/2/4/or 6) or lack the function of the retinoblastoma tumor suppressor protein (RB), which is inactivated by the CDKs. Therefore, isolated inhibition of CDK4/6 should not adversely affect the DNA damaging agent response in the majority of cancers. As would be understood by one of skill in the art upon a review of the instant disclosure, the potential sensitivity of certain tumors to CDK4/6 inhibition can be deduced based on tumor type and molecular genetics. Cancers that are not expected to be affected by the inhibition of CDK4/6 are those that can be characterized by one or more of the group including, but not limited to, increased activity of CDK1 or CDK2, loss or absence of retinoblastoma tumor suppressor protein (RB), high levels of MYC expression, increased cyclin E (e.g., E1 or E2) and increased cyclin A, or expression of a RB-inactivating protein (such as HPV-encoded E7). Such cancers can include, but are not limited to, small cell lung cancer, retinoblastoma, HPV positive malignancies like cervical cancer and certain head and neck cancers, MYC amplified tumors such as Burkitts Lymphoma, and triple negative breast cancer; certain classes of sarcoma, certain classes of non-small cell lung carcinoma, certain classes of melanoma, certain classes of pancreatic cancer, certain classes of leukemia, certain classes of lymphoma, certain classes of brain cancer, certain classes of colon cancer, certain classes of prostate cancer, certain classes of ovarian cancer, certain classes of uterine cancer, certain classes of thyroid and other endocrine tissue cancers, certain classes of salivary cancers, certain classes of thymic carcinomas, certain classes of kidney cancers, certain classes of bladder cancer and certain classes of testicular cancers.

For example, in some embodiments, the cancer is selected from a small cell lung cancer, retinoblastoma and triple negative (ER/PR/Her2 negative) or "basal-like" breast cancer. Small cell lung cancer and retinoblastoma almost always inactivate the retinoblastoma tumor suppressor protein (RB), and therefore does not require CDK4/6 activity to proliferate. Thus, CDK4/6 inhibitor treatment will effect pharmacologic quiescence in the bone marrow and other normal host cells, but not in the tumor. Triple negative (basal-like) breast cancer is also almost always genetically or functionally RB-null. Also, certain virally induced cancers (e.g. cervical cancer and subsets of Head and Neck cancer) express a viral protein (E7) which inactivates RB making these tumors functionally RB-null. Some lung cancers are also believed to be caused by HPV. As would be understood by one of skill in the art, cancers that are not expected to be affected by CDK4/6 inhibitors (e.g., those that are RB-null, that express viral protein E7, or that overexpress MYC) can be determined through methods including, but not limited to, DNA analysis, immunostaining, Western blot analysis, and gene expression profiling.

Selective CDK4/6 inhibitors can also be used in protecting healthy HSPCs during DNA damaging agent treatments of abnormal tissues in non-cancer proliferative diseases, including but not limited to the following: hemangiomatosis in infants, secondary progressive multiple sclerosis, chronic progressive myelodegenerative disease, neurofibromatosis, ganglioneuromatosis, keloid formation, Paget's Disease of the bone, fibrocystic disease of the breast, Peronies and Duputren's fibrosis, restenosis and cirrhosis. Further, selective CDK4/6 inhibitors can be used to ameliorate the effects of DNA damaging agents in the event of accidental exposure or overdose (e.g., methotrexate overdose). Thus, the presently disclosed methods can be used to protect chemical and nuclear plant workers, scientific researchers, and emergency responders from occupational exposure, for example, in the event of a chemical spill or radiation leak.

According to the presently disclosed subject matter, the DNA damaging agent can be administered to a subject on any schedule and in any dose consistent with the prescribed course of treatment, as long as the selective CDK4/6 inhibitor compound is administered prior to, during, or following the administration of the DNA damaging agent. Generally, selective CDK4/6 inhibitor compound can be administered to the subject during the time period ranging from 24 hours prior to exposure with the DNA damaging agent until 24 hours following exposure. However, this time period can be extended to time earlier that 24 hour prior to exposure to the DNA damaging agent (e.g., based upon the time it takes the any DNA damaging chemical compound used to achieve suitable plasma concentrations and/or the DNA damaging compound's plasma half-life). Further, the time period can be extended longer than 24 hours following exposure to the DNA damaging agent so long as later administration of the CDK4/6 inhibitor leads to at least some protective effect. Such post-exposure treatment can be especially useful in cases of accidental exposure or overdose.

In some embodiments, the selective CDK4/6 inhibitor can be administered to the subject at a time period prior to the administration of the DNA damaging agent, so that plasma levels of the selective CDK4/6 inhibitor are peaking at the time of administration of the DNA damaging agent. If convenient, the selective CDK4/6 inhibitor can be administered at the same time as the DNA damaging agent, in order to simplify the treatment regimen. In some embodiments, the chemoprotectant and DNA damaging agent(s) can be provided in a single formulation.

If desired, multiple doses of the selective CDK4/6 inhibitor compound can be administered to the subject. Alternatively, the subject can be given a single dose of the selective CDK4/6 inhibitor.

In some embodiments, selective CDK4/6 inhibitors can be used together with other compounds or treatments to reduce undesirable effects of DNA damaging agents or events. For example, in some embodiments, the presently disclosed subject matter relates to methods of increasing the efficacy of a toxicity reducing agent in a subject in need of treatment thereof, the method comprising: providing a subject that has been exposed to, is being exposed to, or is at risk of being exposed to a DNA damaging agent or event; administering to said subject a toxicity reducing agent; and administering to said subject a pharmaceutically effective amount of a compound that selectively inhibits CDK4 and/or CDK6.

The toxicity reducing agent can be any known toxicity reducing agent. Ideally, the toxicity reducing agent is free of selective CDK4/6 inhibitory activity.

In some embodiments, the toxicity reducing agent is an agent that is being used to or is known to have the ability to reduce undesirable cytotoxicity/side effects related to the use of (or exposure to) a chemotherapeutic. In some embodiments, the toxicity reducing agent is an agent that is being used to, or is known to have the ability to, reduce undesirable toxicity/side effects related to the use of (or exposure to) radiation. Thus, in some embodiments, the toxicity reducing agent is a chemoprotectant or a radioprotectant.

In some embodiments, the toxicity reducing agent is an agent being used so that a higher dose of a chemotherapuetic or of radiation can be tolerated by a subject being treated for cancer or another proliferative disease. In some embodiments, the toxicity reducing agent is being used so that a subject being treated for cancer of another proliferative disease can be treated with a chemotherapeutic or radiation more frequently. In some embodiments, the toxicity reducing agent is used to reduce or prevent side effects associated with the use of the DNA damaging agent, such as, but not limited to, nausea, vomiting, hair loss, anemia, fatigue, peripheral neuropathy, bleeding problems, diarrhea, constipation, and the like.

In some embodiments, the toxicity reducing agent is a growth factor or other naturally occurring compound, or a derivative thereof. In some embodiments, the toxicity reducing agent is selected from the group comprising, but not limited to, growth factors, a granulocyte colony-stimulating factor (G-CSF), a pegylated G-CSF, granulocyte-macrophage colony stimulating factor (GM-CSF), thrombopoietin, erythropoietin (EPO), pegylated erythropoietin, interleukin (IL)-12, steel factor, a keratinocyte growth factor, or to derivatives (e.g., chemically modified compounds having structures based upon one of the foregoing named toxicity reducing agents, such as alkylated or esterified derivatives) or combinations thereof.

In some embodiments, the use of the toxicity reducing agent and the selective CDK4/6 inhibitor can result in synergistic protective effects from the DNA damaging agent or event. In some embodiments, the compound that selectively inhibits CDK4 and/or CDK6 induces pharmacologic quiescence in one or more cells within the subject. For example, transient treatment (e.g., over a period of about 48 hours or less) with the compound that selectively inhibits CDK4 and/or CDK6 can temporarily induce pharmacologic quiescence in one or more cells within the subject. In some embodiments, the one or more cells that are induced in to pharmacologic quiescence are, for example, hematologic cells, hematologic stem cells, and/or hematologic precursor cells. Thus, in some embodiments, a growth factor and a selective CDK4/6 inhibitor compound can be used in a method to provide synergistic effects in the rescue and support of various hematopoietic populations from a DNA damaging agent or event.

In some embodiments, the selective CDK4/6 inhibitor and the toxicity reducing agent can be used in combination to rescue and support various non-hematologic tissues from a DNA damaging agent or event, such as ionizing radiation or a chemotherapeutic. The non-hematologic tissues can include, but are not limited to, cells or tissue from the kidney, gut, heart, liver, brain, thyroid, skin, intestinal mucosa, auditory system, lung, bladder, ovaries, uterus, testicles, adrenals, gallbladder, pancreas, pancreatic islets, stomach, blood vessels, bone, and combinations thereof.

The toxicity reducing agent and the compound that selectively inhibits CDK4 and/or CDK6 can be administered together (e.g., in the same formulation or at the same time in separate formulations) or at different times. Either or both of the toxicity reducing agent and the CDK4/6 inhibitor can be given as a single dose or in multiple doses. In some embodiments, either the CDK4/6 inhibitor or the toxicity reducing agent can be administered prior to the exposure to the DNA damaging agent or event, while the other of the CDK4/6 inhibitor and the toxicity reducing agent can be administer during or after exposure to the DNA damaging agent or event. In some embodiments, both the CDK4/6 inhibitor and the toxicity reducing agent can be administered during exposure to the DNA damaging agent (e.g., during administration of chemo or radiotherapy). Alternatively both can be administered prior to or after exposure to the DNA damaging agent. In some embodiments, the compound that selectively inhibits CDK4 and/or CDK6 is administered to the subject between about 24 and about 48 hours (e.g., about 24, 25, 26, 27, 28, 29, 30, 31, 32, 33, 34, 35, 36, 37, 38, 39, 40, 41, 42, 43, 44, 45, 46 or 48 hours) after exposure of the subject to the DNA damaging agent or event.

In some embodiments, the presently disclosed subject matter is related to the ability of selective CDK4/6 inhibitors to protect non-hematologic cells or tissues from DNA damaging agents or events. Thus, in some embodiments, the presently disclosed subject matter provides a method of mitigating DNA damage in a non-hematologic cell or tissue in a subject in need of treatment thereof prior to or following exposure of the cell or tissue to a DNA damaging agent or event, wherein the method comprises administering to the subject a pharmaceutically effective amount of a compound that selectively inhibits CDK4/6.

In some embodiments, the non-hematologic cell or tissue is comprises a cell or tissue from the group including, but not limited to cells or tissue from the kidney, gut, heart, liver, brain, thyroid, skin, intestinal mucosa, auditory system, lung, bladder, ovaries, uterus, testicles, adrenals, gallbladder, pancreas, pancreatic islets, stomach, blood vessels, bone, and combinations thereof. In some embodiments, the DNA damaging agent is a chemotherapeutic agent, such as, but not limited to, kanamycin, ifosfamide, camptothecin, cyclophosphamide, L-asparaginase, doxorubicin, daunorubicin, methotrexante, irinotecan, cisplatin, streptozotocin, 6-mercaptipurine, bleomycin, busulphan, vincristine, and combinations thereof. Thus, for example, the presently disclosed methods can relate to the use of CDK4/6 inhibitors to protect the kidney cells from chemotherapy-induced epithelial cell damage.

Selective CDK4/6 inhibition appears to have different effects on primary and memory immune responses. In some embodiments, the presently disclosed subject matter is related to the finding that selective CDK4/6 inhibitors preferentially reduce memory T cell proliferation as compared to naive T cell proliferation. Thus, in some embodiments, the presently disclosed subject matter provides a method of reducing or inhibiting memory T cell proliferation in a subject in need of treatment thereof, wherein the method comprises administering to the subject a pharmaceutically effective amount of a compound that selectively inhibits CDK4/6.

In some embodiments, the subject has or is at risk of developing an autoimmune or allergic disease, such as, but not limited to, systemic lupus erythematosus (SLE), rheumatoid arthritis (RA), autoimmune arthritis, scleroderma, hemolytic anemia, autoimmune aplastic anemia, autoimmune granulocytopenia, type I diabetes, thrombotic thrombocytopenic purpura (TTP), psoriasis, inflammatory bowel disease, Crohn's disease, ulcerative colitis, contact dermatitis, polymyalgia rheumatica, uveitis, immune pneumonitis, autoimmune hepatitis, immune nephritis, immune glomerulonephritis, multiple sclerosis, autoimmune neuropathy, vitiligo, discoid lupus, Wegener's Granulomatosis, Henoch-Schoelein Purpura, sclerosing chloangitis, autoimmune thyroiditis, autoimmune myocarditis, autoimmune vasculitis, dermatomyositis, extrinsic and intrinsic reactive airways disease (asthma), myasthenia gravis, autoimmune ovarian failure, pernicious anemia, Addison's disease, autoimmune hypoparathyroidism or other syndromes of an inappropriate cellular immune response. The subject can also have or be at risk of developing another condition related to undesirable memory T cell proliferation.

Selective CDK4/6 inhibitors can also suppress germinal center formation, a process involved in the generation of memory B cells. Thus, in some embodiments, the presently disclosed subject matter provides a method of reducing or inhibiting B cell progenitor proliferation in a subject in need of treatment thereof, the method comprising administering to the subject a pharmaceutically effective amount of a compound that selectively inhibits CDK4/6. In some embodiments, the subject can have or be at risk of developing an autoimmune or allergic disease or another condition related to undesirable B cell proliferation. In some embodiments, the autoimmune or allergic disease, can be for example, such as, but not limited to, SLE, RA, scleroderma, hemolytic anemia, ITP, acquired inhibitors in hemophilia, TTP, Goodpasture's syndrome, cold and warm agglutin diseases, cryoglobulinemia, or a syndrome of inappropriate antibody production.

In some embodiments, the presently disclosed subject matter provides a method of mitigating an autoimmune or allergic disease in a subject in need of treatment thereof, the method comprising administering to the subject a pharmaceutically effective amount of a compound that selectively inhibits CDK4/6, wherein said compound reduces or inhibits memory T cell proliferation, B cell progenitor proliferation, or both memory T cell proliferation and B cell progenitor proliferation. In some embodiments, the autoimmune disease is selected from the group including, but not limited to, SLE, RA, autoimmune arthritis, scleroderma, hemolytic anemia, autoimmune aplastic anemia, autoimmune granulocytopenia, type I diabetes, TTP, psoriasis, inflammatory bowel disease, Crohn's disease, ulcerative colitis, contact dermatitis, polymyalgia rheumatica, uveitis, immune pneumonitis, autoimmune hepatitis, immune nephritis, immune glomerulonephritis, multiple sclerosis, autoimmune neuropathy, vitiligo, discoid lupus, Wegener's Granulomatosis, Henoch-Schoelein Purpura, sclerosing cholangitis, autoimmune thyroiditis, autoimmune myocarditis, autoimmune vasculitis, dermatomyositis, extrinsic and intrinsic reactive airways disease (asthma), myasthenia gravis, autoimmune ovarian failure, pernicious anemia, Addison's disease, autoimmune hypoparathyroidism, other syndromes of an inappropriate cellular immune response, Goodpasture's syndrome, cold and warm agglutin diseases, cryoglobulinemia, or a syndrome of inappropriate antibody production.

In some embodiments, the selective CDK4/6 inhibitor can be used in a method of treating cancer characterized by an increased level of CDK2 activity or by reduced expression of retinoblastoma tumor suppressor protein or a retinoblastoma family member protein or proteins (such as, but not limited to p107 and p130), the method comprising administering to the subject a pharmaceutically effective amount of a compound that selectively inhibits CDK4 and/or CDK6.

In some embodiments, the increased level of CDK2 activity is associated with MYC protooncogene amplification or overexpression and/or the overexpression of Cylcin E1, E2, or Cylin A. The selective CDK4/6 inhibitor is not believed to induce pharmacologic quiescence in cancer cells in these types of cancers. However, the presently disclosed subject matter is related to the belief that selective CDK4/6 inhibitors can increase the sensitivity of cancer cells of certain types of cancers to DNA damaging agents, such as chemotherapeutic compounds and ionizing radiation. Thus, in some embodiments, the use of selective CDK4/6 inhibitors can increase the sensitivity of certain types of cancer cells to damage by DNA damaging agents, such as chemotherapeutic compounds or IR, thereby increasing cancer cell death in comparison to when the DNA damaging agent is used in the absence of administration of the selective CDK4/6 inhibitor. Thus, in some embodiments, a combination of treatment with a DNA damaging agent and a CKD4/6 inhibitor compound can provide a greater reduction in tumor burden than treatment with the DNA damaging agent alone. In some embodiments, administration of the compound that selectively inhibits CDK4 and/or CDK6 can mitigate hematologic toxicity associated with exposure to a DNA damaging agent or event, such as a chemotherapeutic compound or IR. In some embodiments, the hematologic toxicity is a long-term toxicity, such as, but not limited to myelodysplasia. The administration of the selective CDK4/6 inhibitor compound can also protect against other long-term toxicities associated with exposure to the DNA damaging agent or event, including both hematologic and non-hematologic toxicities, such as hematologic and non-hematologic secondary malignancies.

The compound that selectively inhibits CDK4/6 can be administered at any suitable time prior to, during, or after exposure of the subject to the DNA damaging agent or event. In some embodiments, the selective CDK4/6 inhibitor is administered to the subject between about 24 and about 48 hours (e.g., about 24, 25, 26, 27, 28, 29, 30, 31, 32, 33, 34, 35, 36, 37, 38, 39, 40, 41, 42, 43, 44, 45, 46, 47, or 48 hours) after exposure of the subject to the DNA damaging agent or event.

Subjects who have been treated for cancer using radiation or chemotherapy have been found to have a higher risk of developing further cancers (i.e., secondary malignancies, such as cancers that have spread from the original location or new cancers), even when the original cancer treatment successfully eliminates or otherwise treats (e.g., by the reduction of tumor burden) the original (i.e., primary) cancer. The secondary malignancy can be, for example, leukemia, or another hematologic or non-hematologic cancer. These secondary malignancies can sometimes occur several years (e.g. 1, 2, 3, 4, 5, 6, 7, 8, 9, 10, 15, 20, 25, 30 or more years) after the original cancer has been treated and can be related to long-term toxicities of the original cancer treatment.

In some embodiments, the presently disclosed subject matter provides a method of mitigating chemotherapy-induced or radiation-induced secondary malignancies of hematological or non-hematological origin in a subject. In some embodiments, the method can comprise administering to the subject a pharmacologically effective amount of a compound that selectively inhibits CDK4/6. In some embodiments, the compound that selectively inhibits CDK4 and/or CDK6 is administered to the subject prior to or during the same time period that the subject is undergoing chemotherapy or radiation-based therapy to treat a primary malignancy.

III. Active Compounds, Salts and Formulations

As used herein, the term "active compound" refers to a selective CDK 4/6 inhibitor compound, or a prodrug (such as but not limited to various esters and other derivatives that can form the selective CDK4/6 inhibitor in vitro or in vivo), solvate (such as but not limited to a hydrate) and/or pharmaceutically acceptable salt thereof. The active compound can be administered to the subject through any suitable approach. The amount and timing of active compound administered can, of course, be dependent on the subject being treated, on the dosage of DNA damaging agent to which the subject has been, is being, or is anticipated of being exposed to, on the manner of administration, on the pharmacokinetic properties of the active compound, and on the judgment of the prescribing physician. Thus, because of subject to subject variability, the dosages given below are a guideline and the physician can titrate doses of the compound to achieve the treatment that the physician considers appropriate for the subject. In considering the degree of treatment desired, the physician can balance a variety of factors such as age and weight of the subject, presence of preexisting disease, as well as presence of other diseases. Pharmaceutical formulations can be prepared for any desired route of administration, including but not limited to oral, intravenous, or aerosol administration, as discussed in greater detail below.

The therapeutically effective dosage of any specific active compound, the use of which is within the scope of embodiments described herein, can vary somewhat from compound to compound, and subject to subject, and can depend upon the condition of the subject and the route of delivery. As a general proposition, a dosage from about 0.1 to about 200 mg/kg can have therapeutic efficacy, with all weights being calculated based upon the weight of the active compound, including the cases where a salt is employed. In some embodiments, the dosage can be the amount of compound needed to provide a serum concentration of the active compound of up to between about 1-5 µM or higher. Toxicity concerns at the higher level can restrict intravenous dosages to a lower level, such as up to about 10 mg/kg, with all weights being calculated based on the weight of the active base, including the cases where a salt is employed. A dosage from about 10 mg/kg to about 50 mg/kg can be employed for oral administration. Typically, a dosage from about 0.5 mg/kg to 5 mg/kg can be employed for intramuscular injection. In some embodiments, dosages can be from about 1 µmol/kg to about 50 µmol/kg, or, optionally, between about 22 µmol/kg and about 33 µmol/kg of the compound for intravenous or oral administration.

In accordance with the presently disclosed methods, pharmaceutically active compounds as described herein can be administered orally as a solid or as a liquid, or can be administered intramuscularly, intravenously or by inhalation as a solution, suspension, or emulsion. In some embodiments, the compounds or salts also can be administered by inhalation, intravenously, or intramuscularly as a liposomal suspension. When administered through inhalation the active compound or salt can be in the form of a plurality of solid particles or droplets having a particle size from about 0.5 to about 5 microns, and optionally from about 1 to about 2 microns.

The pharmaceutical formulations can comprise an active compound described herein or a pharmaceutically acceptable salt thereof, in any pharmaceutically acceptable carrier. If a solution is desired, water is the carrier of choice with respect to water-soluble compounds or salts. With respect to the water-soluble compounds or salts, an organic vehicle, such as glycerol, propylene glycol, polyethylene glycol, or mixtures thereof, can be suitable. In the latter instance, the organic vehicle can contain a substantial amount of water. The solution in either instance can then be sterilized in a suitable manner known to those in the art, and typically by filtration through a 0.22-micron filter. Subsequent to sterilization, the solution can be dispensed into appropriate receptacles, such as depyrogenated glass vials. The dispensing is optionally done by an aseptic method. Sterilized closures can then be placed on the vials and, if desired, the vial contents can be lyophilized.

In addition to the active compounds or their salts, the pharmaceutical formulations can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the formulations can contain antimicrobial preservatives. Useful antimicrobial preservatives include methylparaben, propylparaben, and benzyl alcohol. An antimicrobial preservative is typically employed when the formulation is placed in a vial designed for multi-dose use. The pharmaceutical formulations described herein can be lyophilized using techniques well known in the art.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch (e.g., potato or tapioca starch) and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules. Materials in this connection also include lactose or milk sugar as well as high molecular weight polyethylene glycols. When aqueous suspensions and/or elixirs are desired for oral administration, the compounds of the presently disclosed subject matter can be combined with various sweetening agents, flavoring agents, coloring agents, emulsifying agents and/or suspending agents, as well as such diluents as water, ethanol, propylene glycol, glycerin and various like combinations thereof.

In yet another embodiment of the subject matter described herein, there is provided an injectable, stable, sterile formulation comprising an active compound as described herein, or a salt thereof, in a unit dosage form in a sealed container. The compound or salt is provided in the form of a lyophilizate, which is capable of being reconstituted with a suitable pharmaceutically acceptable carrier to form a liquid formulation suitable for injection thereof into a subject. When the compound or salt is substantially water-insoluble, a sufficient amount of emulsifying agent, which is physiologically acceptable, can be employed in sufficient quantity to emulsify the compound or salt in an aqueous carrier. Particularly useful emulsifying agents include phosphatidyl cholines and lecithin.

Additional embodiments provided herein include liposomal formulations of the active compounds disclosed herein. The technology for forming liposomal suspensions is well known in the art. When the compound is an aqueous-soluble salt, using conventional liposome technology, the same can be incorporated into lipid vesicles. In such an instance, due to the water solubility of the active compound, the active compound can be substantially entrained within the hydrophilic center or core of the liposomes. The lipid layer employed can be of any conventional composition and can either contain cholesterol or can be cholesterol-free. When the active compound of interest is water-insoluble, again employing conventional liposome formation technology, the salt can be substantially entrained within the hydrophobic lipid bilayer that forms the structure of the liposome. In either instance, the liposomes that are produced can be reduced in size, as through the use of standard sonication and homogenization techniques. The liposomal formulations comprising the active compounds disclosed herein can be lyophilized to produce a lyophilizate, which can be reconstituted with a pharmaceutically acceptable carrier, such as water, to regenerate a liposomal suspension.

Pharmaceutical formulations also are provided which are suitable for administration as an aerosol by inhalation. These formulations comprise a solution or suspension of a desired compound described herein or a salt thereof, or a plurality of solid particles of the compound or salt. The desired formulation can be placed in a small chamber and nebulized. Nebulization can be accomplished by compressed air or by ultrasonic energy to form a plurality of liquid droplets or solid particles comprising the compounds or salts. The liquid droplets or solid particles should have a particle size in the range of about 0.5 to about 10 microns, and optionally from about 0.5 to about 5 microns. The solid particles can be obtained by processing the solid compound or a salt thereof, in any appropriate manner known in the art, such as by micronization. Optionally, the size of the solid particles or droplets can be from about 1 to about 2 microns. In this respect, commercial nebulizers are available to achieve this purpose. The compounds can be administered via an aerosol suspension of respirable particles in a manner set forth in U.S. Pat. No. 5,628,984, the disclosure of which is incorporated herein by reference in its entirety.

When the pharmaceutical formulation suitable for administration as an aerosol is in the form of a liquid, the formulation can comprise a water-soluble active compound in a carrier that comprises water. A surfactant can be present, which lowers the surface tension of the formulation sufficiently to result in the formation of droplets within the desired size range when subjected to nebulization.

As indicated, both water-soluble and water-insoluble active compounds are provided. As used herein, the term "water-soluble" is meant to define any composition that is soluble in water in an amount of about 50 mg/mL, or greater. Also, as used herein, the term "water-insoluble" is meant to define any composition that has a solubility in water of less than about 20 mg/mL. In some embodiments, water-soluble compounds or salts can be desirable whereas in other embodiments water-insoluble compounds or salts likewise can be desirable.

The term "pharmaceutically acceptable salts" as used herein refers to those salts which are, within the scope of sound medical judgment, suitable for use in contact with subjects (e.g., human subjects) without undue toxicity, irritation, allergic response, and the like, commensurate with a reasonable benefit/risk ratio, and effective for their intended use, as well as the zwitterionic forms, where possible, of the compounds of the presently disclosed subject matter.

Thus, the term "salts" refers to the relatively non-toxic, inorganic and organic acid addition salts of compounds of the presently disclosed subject matter. These salts can be prepared in situ during the final isolation and purification of the compounds or by separately reacting the purified compound in its free base form with a suitable organic or inorganic acid and isolating the salt thus formed. In so far as the compounds of the presently disclosed subject matter are basic compounds, they are all capable of forming a wide variety of different salts with various inorganic and organic acids. Although such salts must be pharmaceutically acceptable for administration to animals, it is often desirable in practice to initially isolate the base compound from the reaction mixture as a pharmaceutically unacceptable salt and then simply convert to the free base compound by treatment with an alkaline reagent and thereafter convert the free base to a pharmaceutically acceptable acid addition salt. The acid addition salts of the basic compounds are prepared by contacting the free base form with a sufficient amount of the desired acid to produce the salt in the conventional manner. The free base form can be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the presently disclosed subject matter.

Pharmaceutically acceptable base addition salts are formed with metals or amines, such as alkali and alkaline earth metal hydroxides, or of organic amines. Examples of metals used as cations, include, but are not limited to, sodium, potassium, magnesium, calcium, and the like. Examples of suitable amines include, but are not limited to, N,N'-dibenzylethylenediamine, chloroprocaine, choline, diethanolamine, ethylenediamine, N-methylglucamine, and procaine.

The base addition salts of acidic compounds are prepared by contacting the free acid form with a sufficient amount of the desired base to produce the salt in the conventional manner. The free acid form can be regenerated by contacting the salt form with an acid and isolating the free acid in a conventional manner. The free acid forms differ from their respective salt forms somewhat in certain physical properties such as solubility in polar solvents, but otherwise the salts are equivalent to their respective free acid for purposes of the presently disclosed subject matter.

Salts can be prepared from inorganic acids sulfate, pyrosulfate, bisulfate, sulfite, bisulfite, nitrate, phosphate, monohydrogenphosphate, dihydrogenphosphate, metaphosphate, pyrophosphate, chloride, bromide, iodide such as hydrochloric, nitric, phosphoric, sulfuric, hydrobromic, hydriodic, phosphorus, and the like. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, laurylsulphonate and isethionate salts, and the like. Salts can also be prepared from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. and the like. Representative salts include acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Pharmaceutically acceptable salts can include cations based on the alkali and alkaline earth metals, such as sodium, lithium, potassium, calcium, magnesium and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. Also contemplated are the salts of amino acids such as arginate, gluconate, galacturonate, and the like. See, for example, Berge et al., *J. Pharm. Sci.*, 1977, 66, 1-19, which is incorporated herein by reference.

EXAMPLES

The following Examples provide illustrative embodiments and are not intended to limit the scope of the presently disclosed subject matter in any way. In light of the present disclosure and the general level of skill in the art, those of skill can appreciate that the following Examples are intended to be exemplary only and that numerous changes, modifications, and alterations can be employed without departing from the scope of the presently disclosed subject matter.

The practice of the presently disclosed subject matter can employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current edition); Sambrook et al., *Molecular Cloning: A Laboratory Manual* (2$^{nd}$ Edition, 1989); *Methods in Enzymology* (S. Colowick and N. Kaplan eds., Academic Press, Inc.); *Remington's Pharmaceutical Sciences*, 18$^{th}$ Edition (Easton, Pa.: Mack Publishing Company, 1990); Carey and Sundberg, *Advanced Organic Chemistry* 3$^{rd}$ Ed. (Plenum Press) Vols A and B (1992).

Example 1

Synthesis of PD

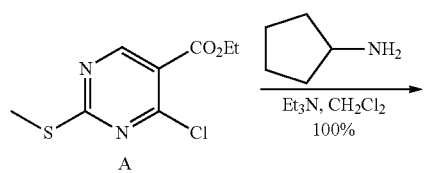

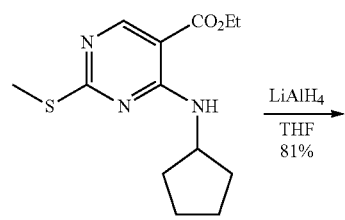

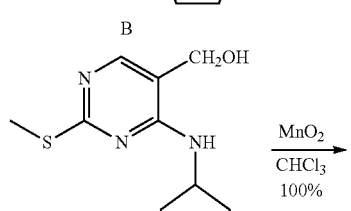

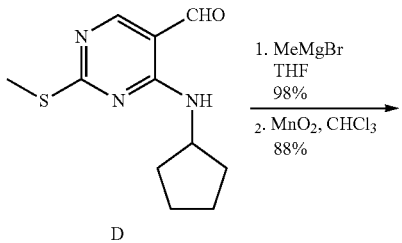

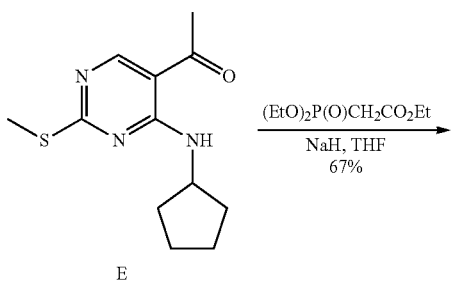

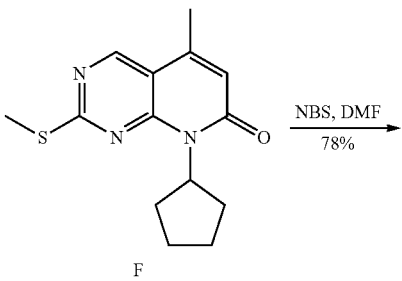

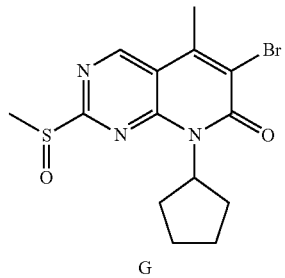

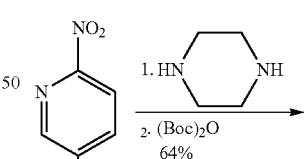

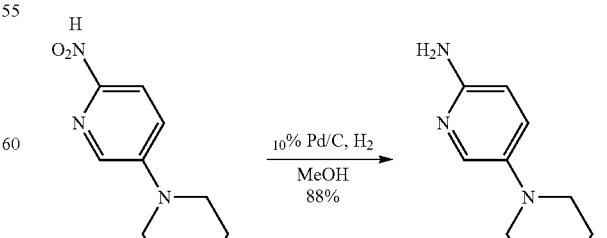

-continued

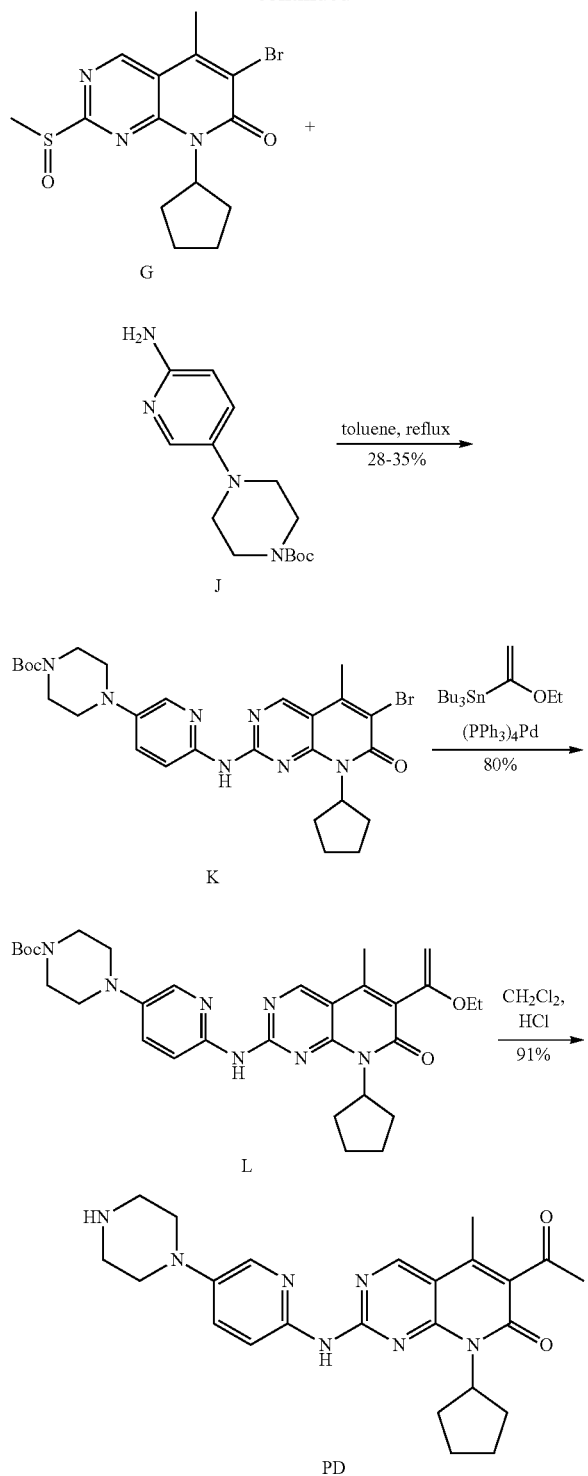

Conversion of Compound D to Compound E:

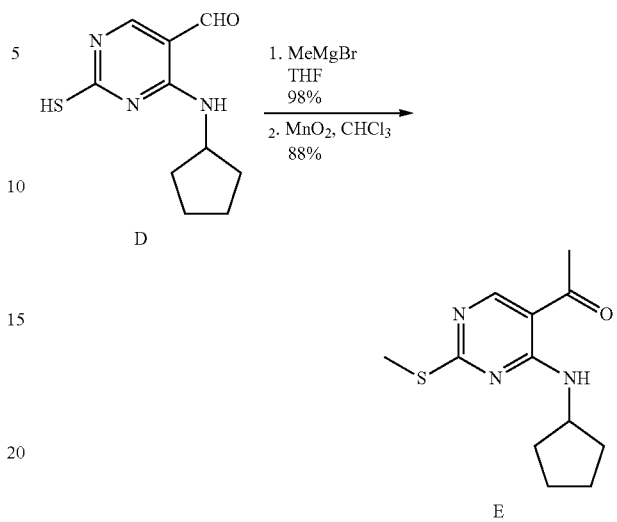

Compound D (40 g, 169 mmol) was dissolved in anhydrous THF (800 mL) under nitrogen and the solution was cooled in ice bath, to which MeMgBr was added slowly (160 mL, 480 mmol, 3 M in ether) and stirred for 1 h. The reaction was quenched with saturated aqueous NH₄Cl the partitioned between water and EtOAc. The organic layer was separated and the aqueous layer was extracted with EtOAc. The combined organic were washed with brine and dried over MgSO₄. Concentration gave an intermediate product as an oil (41.9 g, 98%).

The above intermediate (40 g, 158 mmol) was dissolved in dry CHCl₃ (700 mL). MnO₂ (96 g, 1.11 mol) was added and the mixture was heated to reflux with stirring for 18 h and another MnO₂ (34 g, 395 mmol) was added and continue to reflux for 4 h. The solid was filtrated through a Celite pad and washed with CHCl₃. The filtrate was concentrated to give a yellow solid compound E (35 g, 88%), Mp: 75.8-76.6° C.

Conversion of Compound F to Compound G:

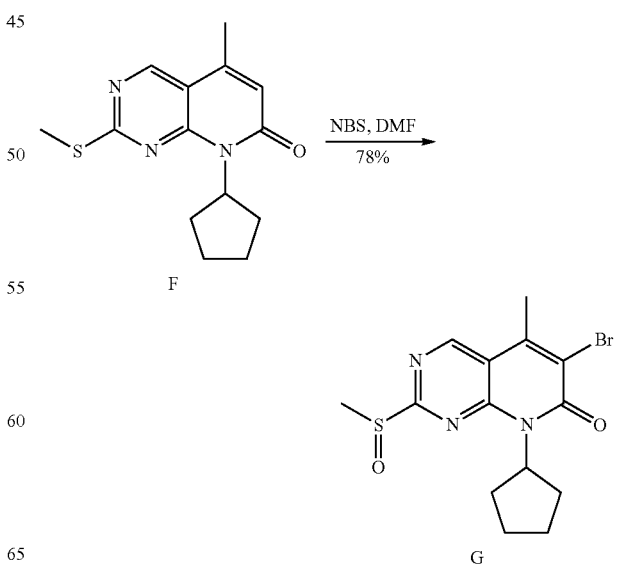

Scheme 1: Synthesis of PD.

PD was synthesized as shown above in Scheme 1. Reactions shown in Scheme 1 generally followed previously reported procedures (see VandelWel et al., *J. Med Chem.*, 48, 2371-2387 (2005); and Toogood et al., *J. Med. Chem.*, 48, 2388-2406 (2005)), with the exceptions of the reaction converting compound D to compound E and the reaction converting compound F to compound G.

Compound F (5 g, 18.2 mmol) was dissolved in anhydrous DMF (150 mL) and NBS (11.3 g, 63.6 mmol) was added. The reaction mixture was stirred at r.t. for 3.5 h and then poured into H$_2$O (500 mL), the precipitate was filtered and washed with H$_2$O. The solid recrystallized from EtOH to give compound G as a white solid (5.42 g, 80.7%), mp: 210.6-211.3° C.

Characterization Data for PD:
LC-MS: 448.5 (ESI, M+H). Purity: ~99%
$^1$H NMR (300 MHz, D$_2$O): 9.00 (s, 1H), 8.12 (dd, J=9.3 Hz, 2.1 Hz, 1H), 7.81 (d, J=2.4 Hz, 1H), 7.46 (d, J=9.6 Hz, 1H), 5.80-5.74 (m, 1H), 3.57-3.48 (m, 8H), 2.48 (s, 3H), 2.37 (s, 3H), 2.13-1.94 (m, 6H), 1.73-1.71 (m, 2H).
$^{13}$C NMR (75 MHz, D$_2$O): 203.6, 159.0, 153.5, 153.3, 152.2, 139.9, 139.4, 139.2, 133.1, 129.0, 118.7, 113.8, 107.4, 51.8, 42.2, 40.0, 28.0, 25.2, 22.6, 10.8.

Example 2

General Methods for In Vitro and In Vivo Studies

Compounds:
PD0332991 was synthesized as described in Example 1.
Cells, Cell Cycle Analysis, γH2AX by Flow Cytometry, Cell Proliferation Assays and Cellular Toxicity:
Primary normal human renal proximal epithelial cells (American Type Culture Collection (ATCC), Manassas, Va., United States of America) were cultured in renal epithelial cell basal media supplemented with renal epithelial cell growth kit according to the manufacturer's recommendations. Cell cycle analysis was performed using BrdU (BD Biosciences Pharmingen, San Diego, Calif.) or EdU (Invitrogen Corporation, Carlsbad, Calif., United States of America) and propidium iodide following the manufacturer's protocols. For the γH2AX assay, cells were fixed, permeabilized, and stained with anti-γH2AX as per γH2AX Flow Kit (Millipore, Billerica, Mass., United States of America). γH2AX levels were assessed by flow cytometry. Cell proliferation was assessed by seeding 1×10$^3$ cells per well in a 96-well tissue culture plate in 100 μL of growth medium. Cells were treated as indicated with Cdk4/6 inhibitors and etoposide. Following treatment, cells were allowed to recover for 7 days in normal growth medium. At the end of the recovery period, cell number was quantified using CellTiter-Glo® (Promega, Fitchburg, Wis., United States of America) or WST-1 reagent (TaKaRa Bio USA, Madison, Wis., United States of America). Cellular cytotoxicity was assessed using the TOXILIGHT™ Bioassay kit (Lonza, Basel, Switzerland) which measures cytolysis by quantifying the release of Adenylate Kinase into the culture media. Briefly, 20 μL was aspirated from each well of 96 well plates of cells treated with varying concentrations of PD0332991. 100 μL of TOXILIGHT™ reagent is added and incubated for 5 minutes and read in a luminometer at 1 second/well.

Animals:
All animal experiments were performed in accord with the UNC Institutional Animal Care and Use Committee. Young adult C57Bl/6 and FVB mice were irradiated using a 137Cs AECL GammaCell 40 Irradiator (Atomic Energy of Canada Ltd., Mississauga, Ontario, Canada). Mice analyzed were young adult (8-12 weeks of age) virgin female C57Bl/6 or FVB purchased from Jackson Labs (Bar Harbor, Me., United States of America), unless otherwise specified.

The C3-TAg mice are a model of basal-like breast cancer. The C3-TAg mice contain a recombinant gene expressing the simian virus 40 early-region transforming sequence (SV40 large T antigen), which has been shown to inactivate both p53 and Rb. The MMTV-c-neu model expresses c-neu (the mouse ortholog of human HER2) driven by the mouse mammary tumor virus (MMTV) promoter and is a model of HER2+ breast cancer. When tumors were noted to be ~0.2 cm$^2$ in size, animals were treated as described and tumor response assessed by daily caliper measurements.

Drug Preparation and Dosing:
PD0332991 was dissolved in sodium lactate buffer (pH 4.0) to a final concentration of 15 mg/ml. Mice were treated with a 150 mg/kg dose of PD0332991. 2BrIC (also referred to herein as L4D) was solubilized in DMSO and added to cells where final concentration of DMSO<0.1%.

Analysis of BrdU Incorporation:
For kidney proliferation experiments, mice were treated with a single dose of PD0332991 (150 mg/kg oral gavage) or vehicle control followed by cisplatin (10 mg/kg IP). Proliferation was assessed by using BrdU (1 mg IP injection) every 6 hours for 24 hours prior to sacrifice or 100 mg of EdU (0.1 mg IP) every 24 hours for 3 days prior to sacrifice.

Analysis of EdU Incorporation by Flow Cytometry:
Kidneys were harvested from mice and single cells were isolated using a gentleMACS™ tissue dissociator (Miltinyi Biotec, Bergisch Gladbach, Germany). Briefly, kidneys were cut into small pieces and placed in 10 ml collagenase (1 mg/ml) in a gentleMACS™ C tube (Miltinyi Biotec, Bergisch Gladbach, Germany). Tissue was dissociated following the manufacturer's recommendations (Miltinyi Biotec, Bergisch Gladbach, Germany). Cells were then incubated for 5 minutes in ACK buffer to lyse red blood cells, filtered and pelleted. Cells were resuspended in 4% paraformaldehyde and stored overnight at 4° C. For quantification of EdU incorporation, the cells were fixed, permeabilized, and stained with an APC EdU Flow Kit according to the manufacturer's instruction (Invitrogen Corporation, Carlsbad, Calif., United States of America). Flow cytometric analysis was performed using a CyAn ADP (Dako, Glostrup, Denmark). For each sample, a minimum of 500,000 cells was analyzed and the data were analyzed using FlowJo software (Tree Star, Inc., Ashland, Oreg., United States of America).

Myelosuppression Assay: Weekly Complete Blood Counts:
In the radioprotection experiments, mice were treated with a PD0332991 150 mg/kg by oral gavage or vehicle control one hour before exposure to radiation (6.5 Gy). Erythropoietin (4000 units/day) was given beginning on day 3 following exposure to radiation and continued for three consecutive days.

Baseline complete blood cell (CBC) anaylsis was performed on a subset of mice prior to drug administration. Following drug administration (chemotherapy/radiation +/−CDK4/6 inhibitor/erythropoietin or control), CBC analysis was performed on day 10 and 17 following treatment. 40 μl of blood was collected by tail vein nick in BD Microtainer tubes with K2E (K$_2$EDTA). Blood was analyzed using a Hemavet CBC-Diff Veterinary Hematology System (Drew Scientific Inc., Dallas, Tex., United States of America). CBC analysis included measurement of white blood cells, lymphocytes, granulocytes, monocytes, hematocrit, red blood cells, hemoglobin, platelets, and other common hematological parameters.

Statistical Analysis:
Unless otherwise noted, comparisons are made with one-way ANOVA with Bonferroni correction for multiple comparisons where appropriate. Error bars are +/−standard error of the mean (SEM) or standard deviation as indicated.

Example 3

Augmentation of Growth Factor Efficacy by CDK4/6 Inhibition

Cohorts of FVB wild type mice were given placebo or CDK4/6 inhibitor (PD0332991, 150 mg/kg oral gavage) just prior to receiving a sub-lethal dose of irradiation (6.5 Gcy). Three doses of normal saline (control) or erythropoietin (EPO) 100 units were administered by subcutaneous injection at times 72, 96, and 120 hours post-irradiation. In total, there were four treatment cohorts (PD0332991+Saline, PD0332991+EPO, Saline+EPO, Saline+Saline). The sample size for each cohort was: Control=7; EPO=8; PD0332991=8, PD/EPO=6. Serial blood draws were performed at baseline, 10 days post irradiation, and 17 days post irradiation. Complete blood counts (CBCs) were assessed to determine the number of red blood cells, various leukocytes subpopulations and platelets.

EPO alone or in combination with PD0332991 had no effect on platelets (FIG. 1) or other non-erythroid cell lineages, whereas both treatment cohorts that received PD0332991 showed improved platelet counts (FIG. 1) as well as other non-erythroid cell lineages. EPO alone was not able to improve erythroid cell lineage. Without being bound to any one theory, this is believed to be because EPO treatment stimulated erythroid progenitors harboring DNA damage to enter the cell cycle resulting in subsequent apoptosis. However, treatment of mice with PD0332991 in combination with EPO showed marked improvement in erythroid function as shown by improved RBC, Hb, and HCT measurements. Again without being bound to any one theory, it is believed that PD0332991 allows erythroid progenitors to repair DNA damage from radiation and then subsequent EPO treatment is believed to stimulate the progenitors to expedite erythroid replacement. In conclusion, CDK4/6 inhibitors appear to enhance the efficacy of growth factors to rescue and support the various hematopoietic populations following exposure to DNA damaging agents such as radiation or chemotherapy. Thus, for example, as part of chemotherapy-based cancer treatment regimes, CDK4/6 inhibition around the time of DNA damage can be used to enhance growth factor support of bone marrow suppression by allowing bone marrow stem and progenitors to repair DNA damage before growth factor administration has begun. Further, CDK4/6 inhibition will mitigate long term (e.g., 3 or more years post chemotherapy) bone marrow toxicities (for example, myelodysplasia) related to the use of growth factors in cancer patients who survive the disease.

CDK4/6 inhibition around the time of DNA damaging exposure can augment the efficacy of growth factors such as (but not limited to) G-CSF and derivatives (e.g. pegylated G-CSF), GM-CSF and derivatives, thrombopoietin and derivatives, erythropoietin and derivatives (e.g. pegylated erythropoietin), IL12, steel factor, Keratinocyte growth factors. These agents, especially G-CSF, GM-CSF and erythropoietin and derivatives, are clinically used to reduce the toxicity of chemotherapy and radiation in the care of cancer patients. Pharmacologic quiescence induction through CDK4/6 inhibition around the time of DNA damaging exposure can augment the efficacy of these agents at a later time point (e.g., growth factors administration is usually begun 24-72 after the DNA damaging therapeutic).

Example 4

Protection of Non-Hematologic Tissues and Cells by CDK4/6 Inhibition

Figure 2A:
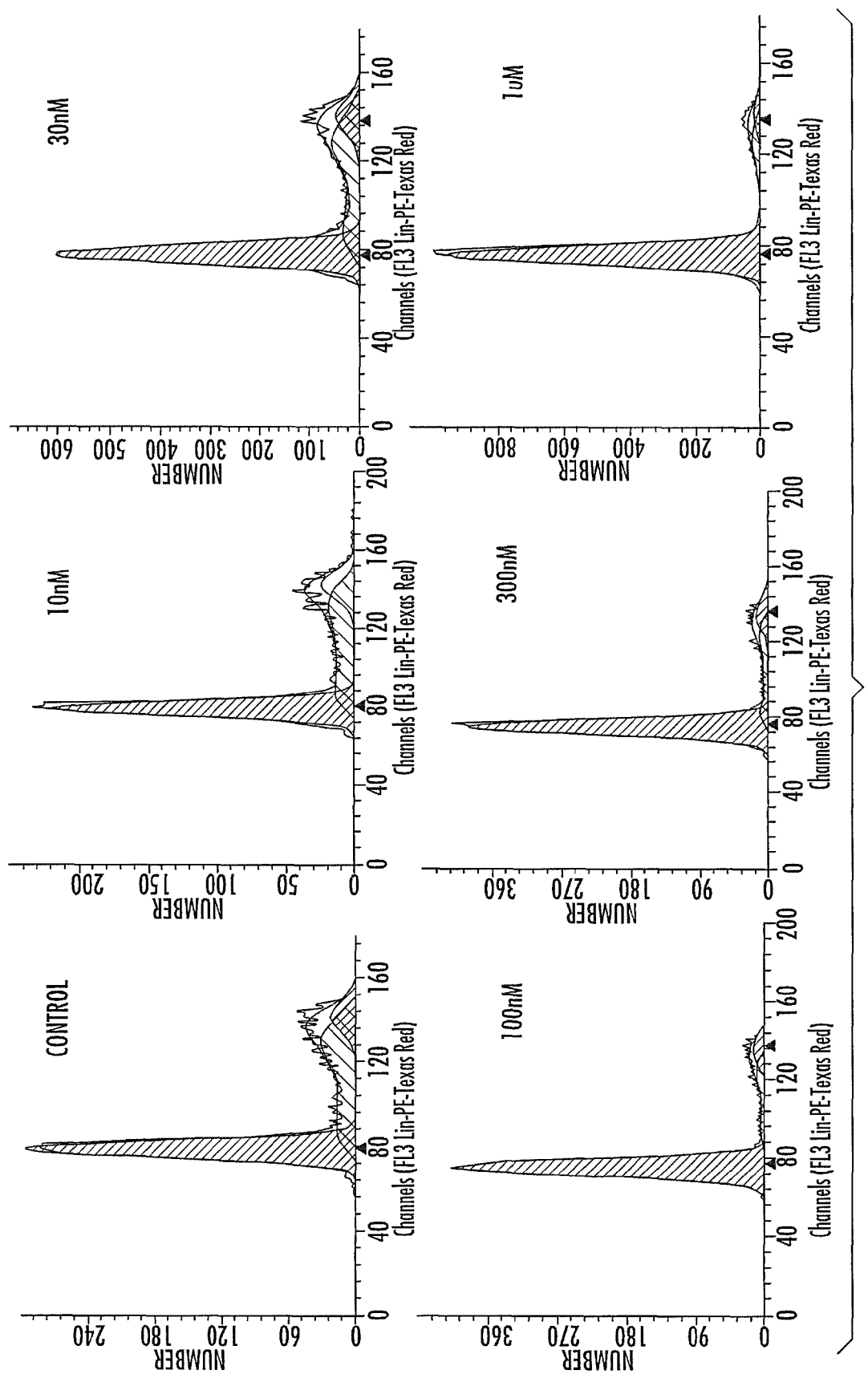
FIG. 2A: CDK4/6 inhibition induces a $G_1$ arrest in primary human renal proximal tubule epithelial cells. Representative histograms of cell cycle analysis of Primary human renal proximal tubule epithelial cells treated with varying concentrations of PD0332991 for 16 hours. Cells were harvested, fixed, stained, and analyzed by flow cytometry. Data was fitted using Mod-Fit™ software from Verity (Verity Software House, Topsham, Me., United States of America). Increasing concentrations of CDK4/6 inhibitor produce a "clean" G1-arrest without evidence of cytotoxicity.
Figure 2B:
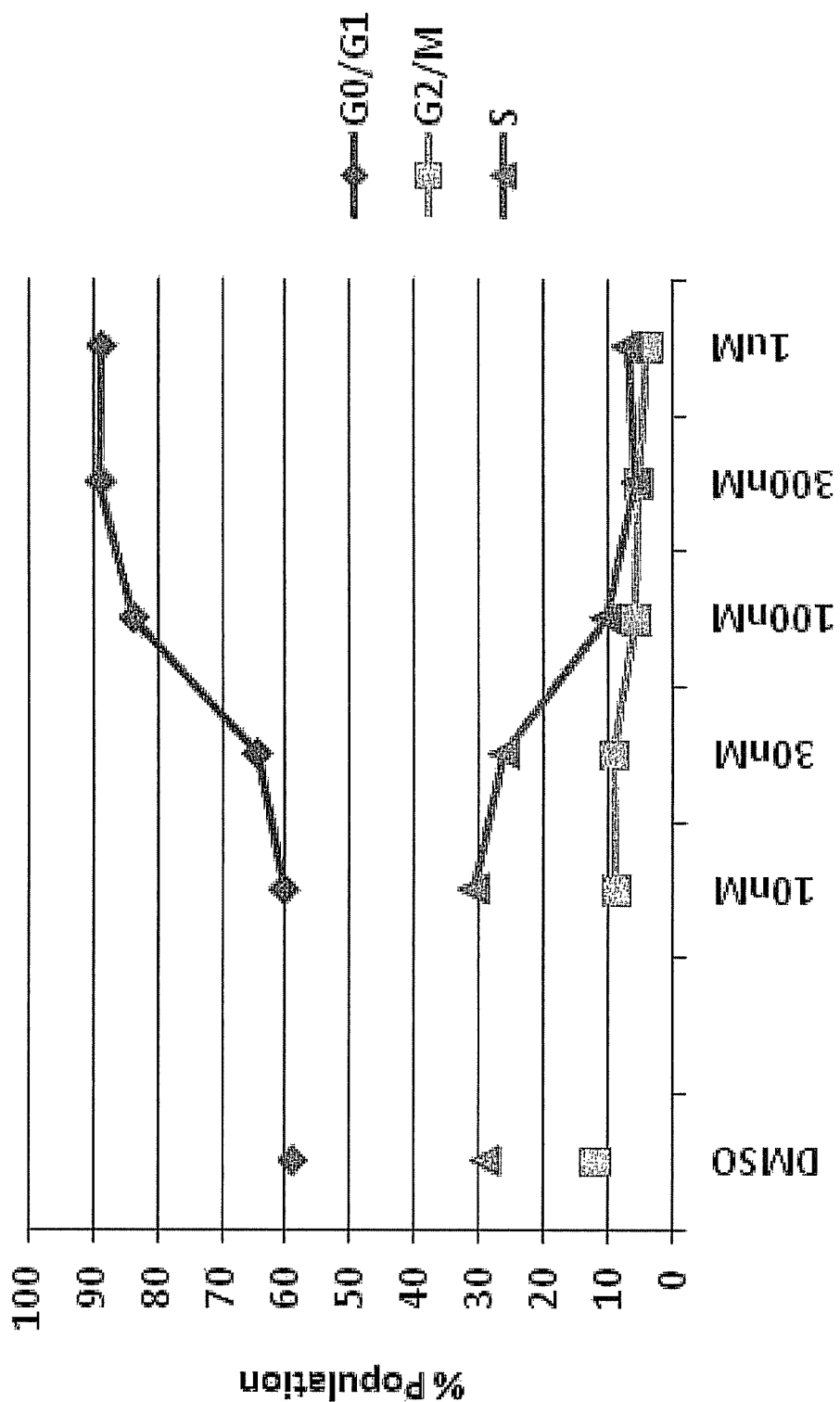
FIG. 2B: CDK4/6 inhibition induces a $G_1$ arrest in primary human renal proximal tubule epithelial cells. Cell cycle analysis of Primary human renal proximal tubule epithelial cells treated with varying concentrations of PD0332991 for 16 hours. Cells were harvested, fixed, stained, and analyzed by flow cytometry. Data was fitted using Mod-Fit™ software from Verity (Verity Software House, Topsham, Me., United States of America). Corresponding % of cells in G1 (diamonds), G2/M (squares) and S (triangles) are shown on the graph.

Use of a potent and selective CDK4/6 inhibitor, such as PD0332991, induces a G1 arrest in normal human primary renal proximal tubule epithelial cells. See FIGS. 2A and 2B. A dose dependent increase in the G0/G1 fraction of the cell cycle was observed with a consummate decrease in both G2/M and S-phase fractions. In doing so, the cells enter pharmacologic quiescence and are held in this state until they are released from this arrest.

Normal human primary renal proximal tubule epithelial cells were plated and exposed 24 hours later to PD0332991 at concentrations of 0, 10 nM, 30 nM, 100 nM, 300 nM or 1 uM. Sixteen hours post treatment; cells were harvested by standard methods, fixed in ice-cold methanol until time for DNA staining. Samples were processed and the DNA was stained with propidium iodide (PI) solution and analyzed by flow cytometry. FCS files from flow cytometer were further analyzed using cell cycle analysis software Mod-Fit™ from Verity (Verity Software House, Topsham, Me., United States of America), where cell cycle fractions were calculated as a percentage of the whole population.

Figure 3:
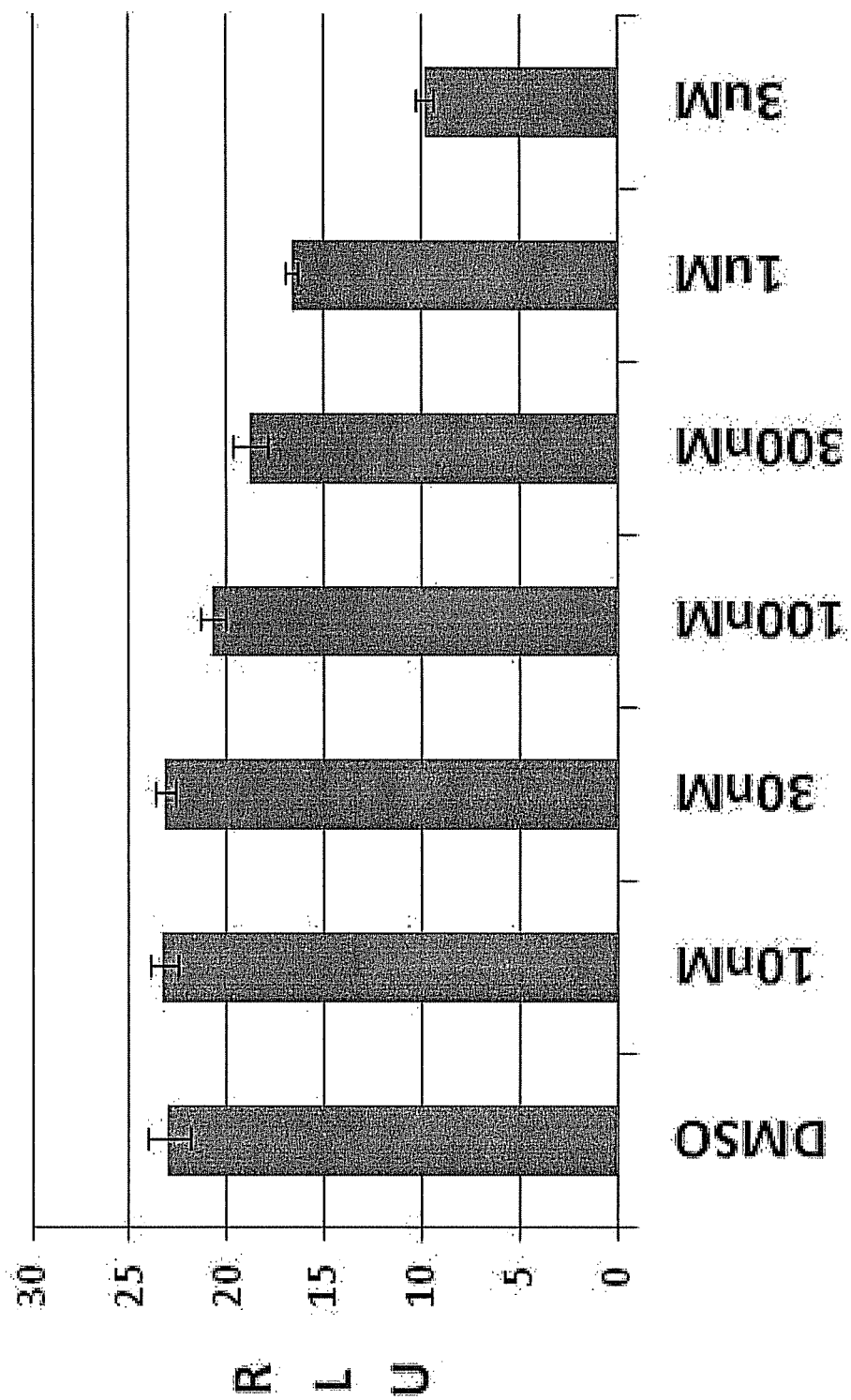
FIG. 3: CDK4/6 inhibition blocks proliferation of primary human renal proximal tubule epithelial cells. Cells were treated with varying concentrations of PD0332991 for 72 hours. Following incubation, cell proliferation was quantified using CellTiter-Glo® (Promega, Madison, Wis., United States of America). Data represent the mean of four replicates (relative light units, RLU) +/−standard deviation.

Inhibition of CDK4/6 blocks the proliferation of normal human primary renal proximal tubule epithelial cells. These cells were seeded at an appropriate density in 96 well plates and incubated for 24 hours at 37° C. in a humidified incubator at 5% $CO_2$. Cells were then exposed to a potent and selective Cdk4/6 inhibitor, in this case PD0332991, across a broad dose range 24 hours later. The dose range explored is 0, 10 nM, 30 nM, 100 nM, 300 nM, 1 µM or 3 µM PD0332991. Seventy-two hours post exposure, the CDK4/6 inhibited cells were treated with CellTiter-Glo® (Promega, Madison, Wis., United States of America) using manufacturer's specifications. The plate was read in luminometer at 1 second/well. Results were placed in Microsoft Excel and analyzed. In FIG. 3, a clear dose dependent inhibition of cell proliferation is obtained in the presence of this inhibitor when compared to DMSO control by 72 hours post treatment. This result, in conjunction with FIGS. 2A and 2B demonstrates that Cdk4/6 dependent non-hematologic cells can enter pharmacologic quiescence and are thusly inhibited from proliferating.

Figure 4:
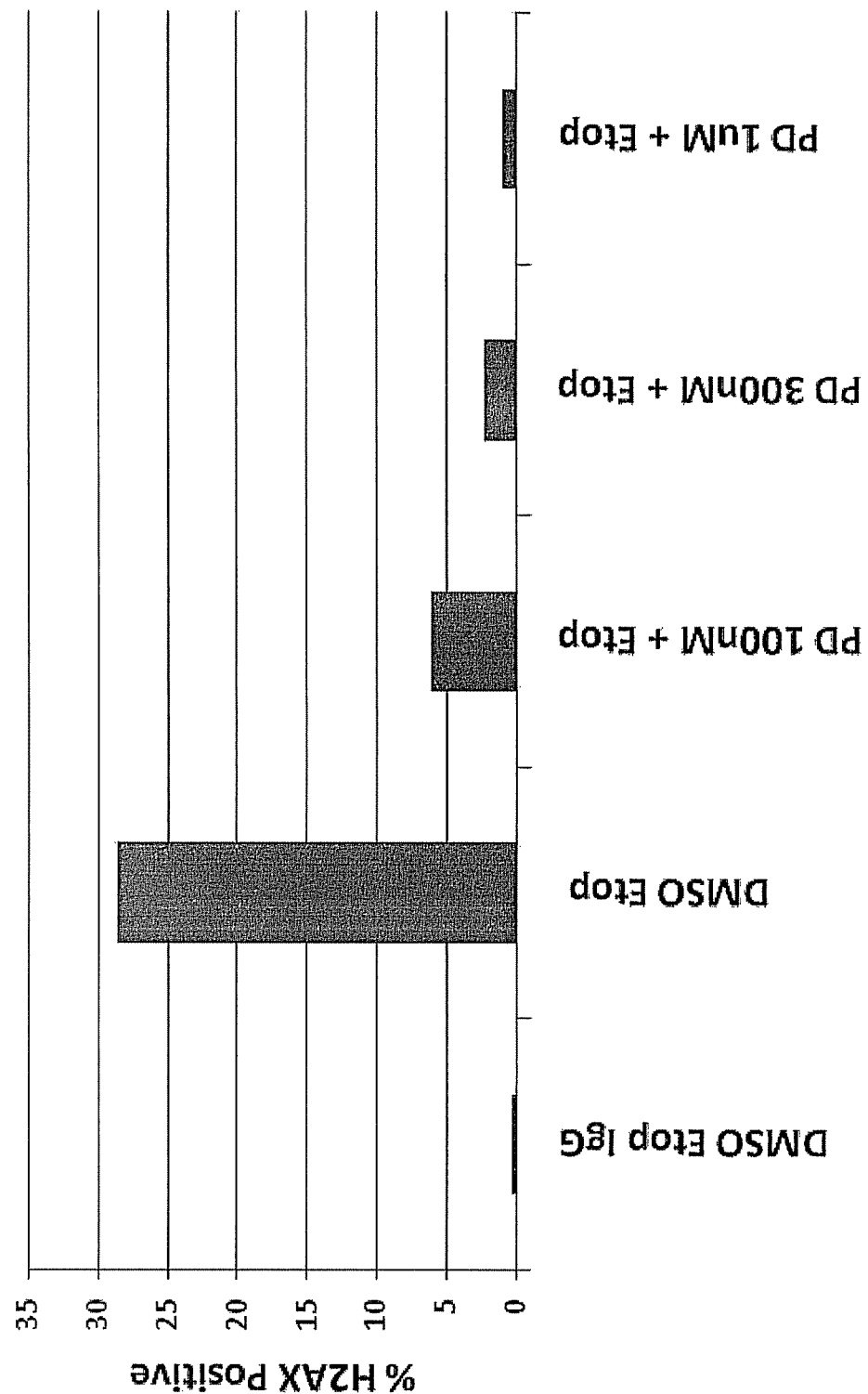
FIG. 4: CDK4/6 inhibition abrogates etoposide-induced DNA damage in primary human renal proximal tubule epithelial cells. Cells were pretreated for 16 hours with PD0332991 followed by 8 hours with etoposide (Etop). Cells were collected, fixed and stained with anti-γH2AX FITC and analyzed by flow cytometry. Data was analyzed using FlowJo (Treestar, Inc., Ashland, Oreg., United States of America). The % γH2AX positive cells are shown in the accompanying graph.

CDK4/6 inhibition abrogates etoposide-induced DNA damage in normal human primary renal proximal tubule epithelial cells. In cell cultures exposed to DNA damaging small molecules or ionizing radiation, double-stranded DNA breaks are generated rapidly which will lead to the phosphorylation of H2AX. Phosphorylation of H2AX corresponds with double stranded DNA breaks. In FIG. 4, normal human primary renal proximal tubule epithelial cells were plated and treated them 24 hours later with 0, 100 nM, 300 nM or 1 µM PD0332991. Sixteen hours later, these samples were exposed to 2.5 µM etoposide for eight hours. Samples were then harvested, fixed and stained for γH2AX using Millipore Corporation H2AXx Phosphorylation Assay Kit for Flow Cytometry (Millipore, Billerica, Mass., United States of America). Samples were run on our flow cytometer and results processed through FlowJo Flow Cytometry Analytical Software (Treestar, Inc., Ashland, Oreg., United States of America). These results demonstrate that pharmacologic quiescence provides protection of chemotherapeutically induced DNA damage through pharmacoquiesence in a dose dependent manner.

Figure 5:
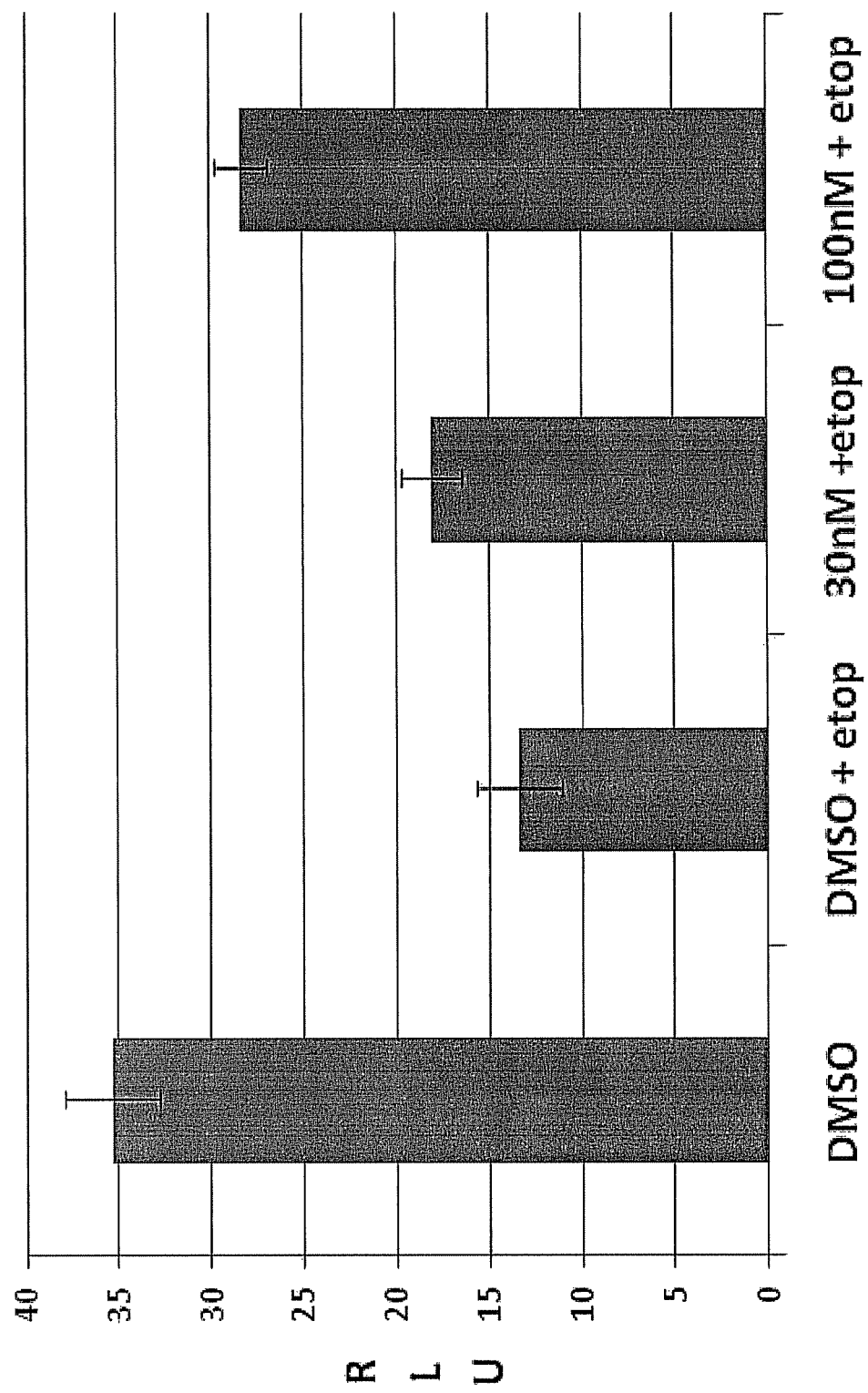
FIG. 5: CDK4/6 inhibition protects primary human renal proximal tubule epithelial cells from etoposide-induced cell death. PD0332991 inhibits chemotherapy-induced cytotoxicity in a cdk4/6 dependent manner. Primary human renal proximal tubule epithelial cells were incubated with 30 nM or 100 nM PD0332991 for 16 hours. Etoposide (Etop, 2.5 μM) was added for 8 hours. Following incubation, the media was replaced with fresh media and the cells were incubated for an additional 7 days. On day 7, cell proliferation was assessed using CellTiter-Glo® (Promega, Madison, Wis., United States of America). Error bars show +/−standard deviation.

CDK4/6 inhibition protects normal human primary renal proximal tubule epithelial cells from etoposide-induced cell death. In FIG. 5, it is demonstrated that the use of a selective and potent CDK4/6 inhibitor in non-hematologic cells dependent of CDK4/6 can provide protection from DNA damaging agents, such as, but not limited to, etoposide. Normal human primary renal proximal tubule epithelial cells were plated and treated with increasing doses of the CDK4/6 inhibitor PD0332991 24 hours after seeding. Sixteen hours after treatment, these cells were dosed with 2.5 µM etoposide for 8 hours. Media was removed and replace with fresh media. Cells were maintained in culture for 7 days at which they were evaluated with CellTiter-Glo® (Promega, Madison, Wis., United States of America) using manufacturer's specifications for effects on cell proliferation. The plate was read in luminometer at 1 second/well. Results were placed in Microsoft Excel and analyzed. Cells treated with increasing doses on PD0332991 exhibit in a dose dependent manner protection from etoposide induced cell death.

Figure 6:
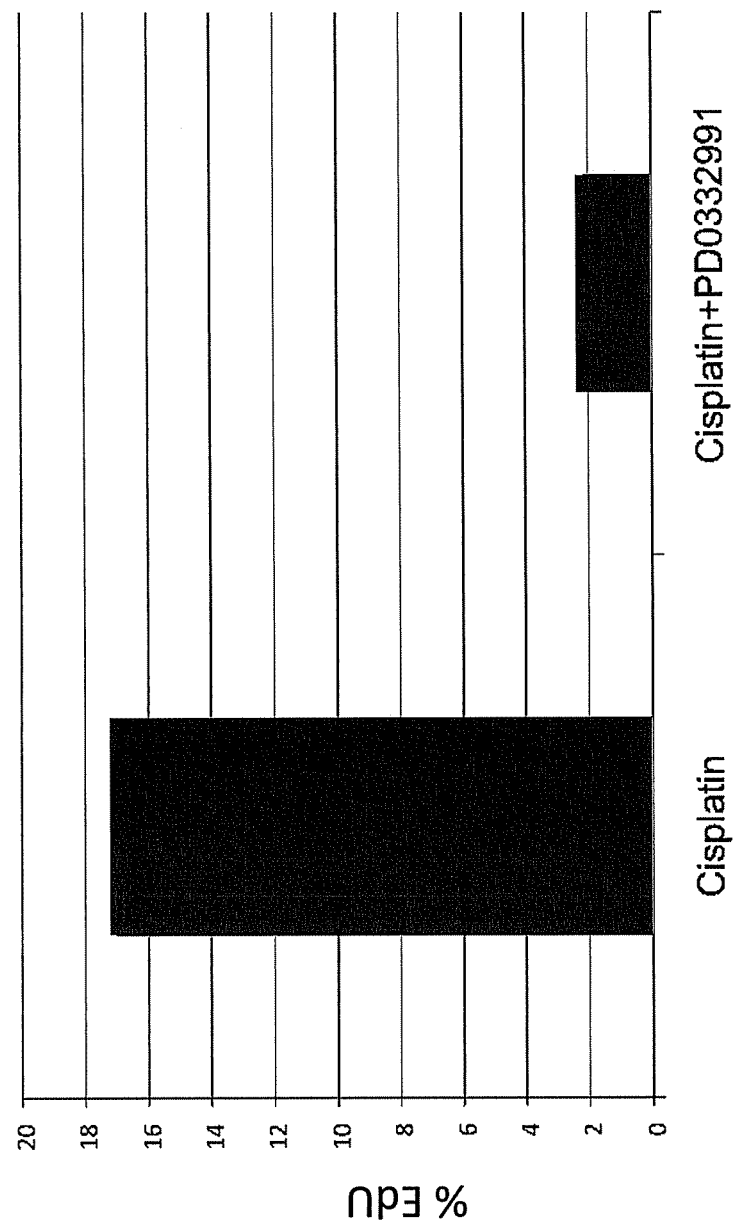
FIG. 6: CDK4/6 inhibition blocks EdU incorporation into whole kidney in mice treated with cisplatin. Mice were treated with PD0332991 (150 mg/kg) by oral gavage one hour prior to intraperitoneal (IP) injection of cisplatin (10 mg/kg). EdU (100 mg/mouse) was given IP every 24 hours prior to sacrifice. Kidneys were collected and single cell isolates were prepared and stained for EdU incorporation. Proliferation was assessed by flow cytometry. Data represents % of EdU staining in untreated, cisplatin-treated and cisplatin/PD0332991 treated cells.

The kidney is relatively quiescent until challenged by a renal insult. Therefore, to determine whether renal cell proliferation was dependent on CDK4/6 activity in vivo, renal cell proliferation was stimulated by treating female FVB wt mice with cisplatin, a known nephrotoxic chemotherapeutic agent. At time 0 hr, mice were started on chow delivering PD0332991 100 mg/kg per day or standard chow with no drug. At 24 hours mice received a single dose of cisplatin 15 mg/kg by IP injection and an IP injection of 100 mcg of EdU. At 48 hours all mice received a second dose of 100 mcg EdU by IP injection. After 72 hours mice were euthanized and kidneys were harvested. Single cell suspensions of renal cells were made by gently grinding the kidneys using the gentleMACS™ tissue dissociator (Miltinyi Biotec, Bergisch Gladbach, Germany). Single cell suspensions were then used to measure EdU incorporation flow cytometric analysis. Mice treated with cisplatin and vehicle control showed approximately 17% of cells labeled with EdU, whereas mice treated with cisplatin and PD0332991 only had approximately 2% of cells stained positive for EdU incorporation. See FIG. 6. Thus, CDK4/6 inhibition resulted in an 88% reduction in cell proliferation, further confirming the in vitro analysis that renal cell proliferation is dependent on CDK4/6 activity.

Figure 7:
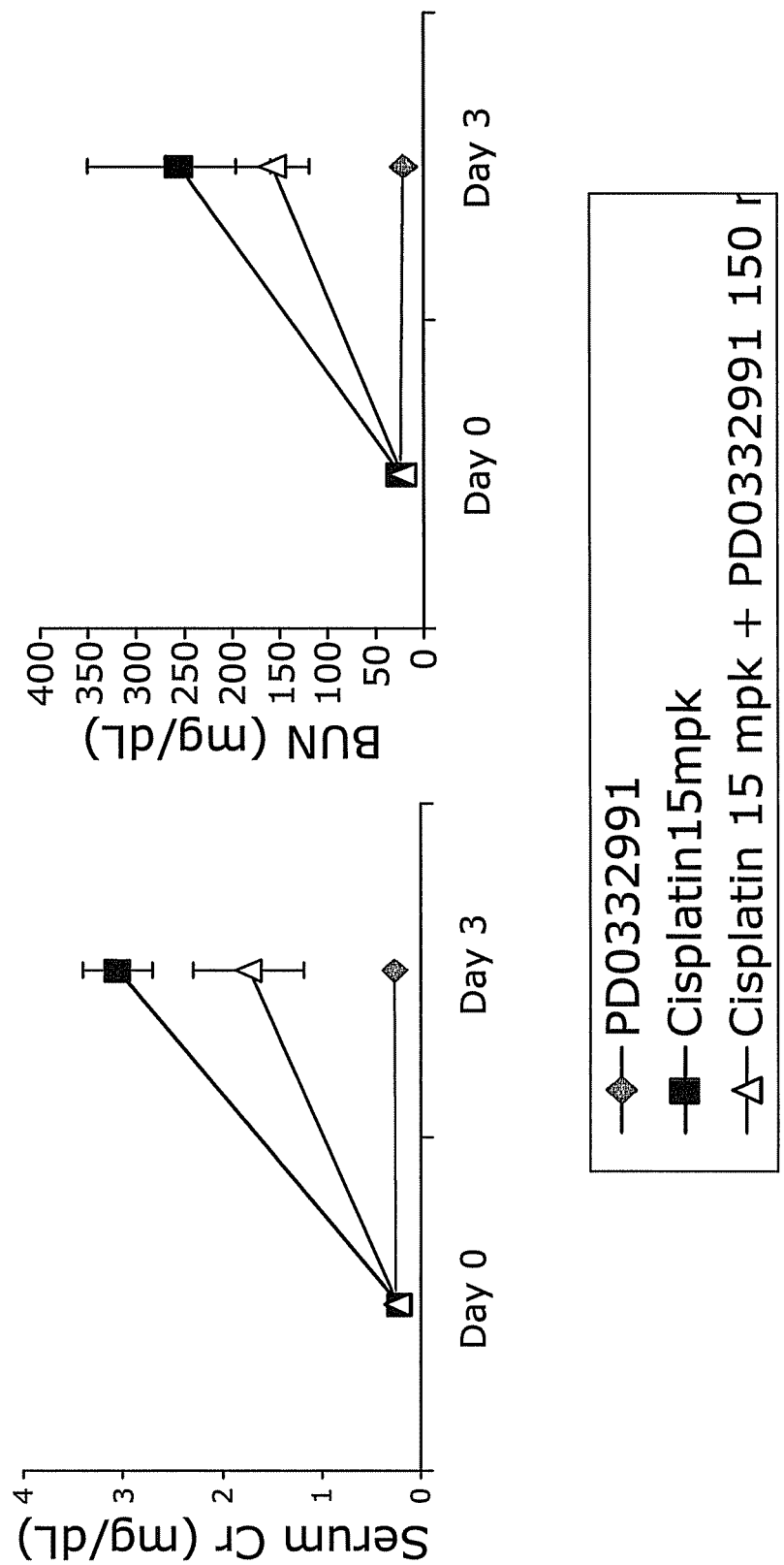
FIG. 7: CDK4/6 inhibition protects kidney function in mice treated with cisplatin. Cohorts of mice were treated with cisplatin (10 mg/kg IP) alone (squares), PD0332991 (150 mg/kg PO) alone (diamonds) or immediately prior to cisplatin (10 mg/kg) (triangles). Kidney function was measured at day 7 by quantification of blood urea nitrogen (BUN) in mg/dL and serum creatinine (Serum Cr) in mg/dL. Data represents the mean of 6 animals per cohort +/−standard error of the mean.

To determine if CDK4/6 inhibition around the time of DNA damage would protect renal function, mice were treated with cisplatin, a known causative agent of renal tubular damage in humans. Mice were treated with PD0332991 150 mg/kg or vehicle control by oral gavage and then received a single dose of cisplatin 15 mg/kg by IP injection. 72 hours post treatment mice were euthanized and blood was collected by cardiac puncture for BUN (blood urea nitrogen) and serum creatinine (SrCr) analysis. Serum BUN and SrCr are common markers of renal function and serum levels quickly elevated when kidney function has been acutely compromised. FIG. 7 shown a dramatic increase in BUN and SrCr following cisplatin administration and a single dose of PD0332991 co-administered with the cisplatin was able to abrogate the cisplatin-induced nephrotoxicity.

CDK4/6 appears to play a role in cell proliferation of certain non-hematological tissues, such as the kidney. Thus, CDK4/6 inhibitors can be used to protect non-hematological tissues, such as, but not limited to, kidney, gut, heart, liver, brain, thyroid, skin, intestinal mucosa, auditory system, lung, bladder, ovaries, uterus, testicles, adrenals, gallbladder, pancreas and pancreatic islets, stomach, blood vessels, and bone, from DNA damaging agents such as radiation and chemotherapy.

Example 5

Augmentation of DNA Damaging Agent Efficacy by CDK4/6 Inhibition

Figure 8:
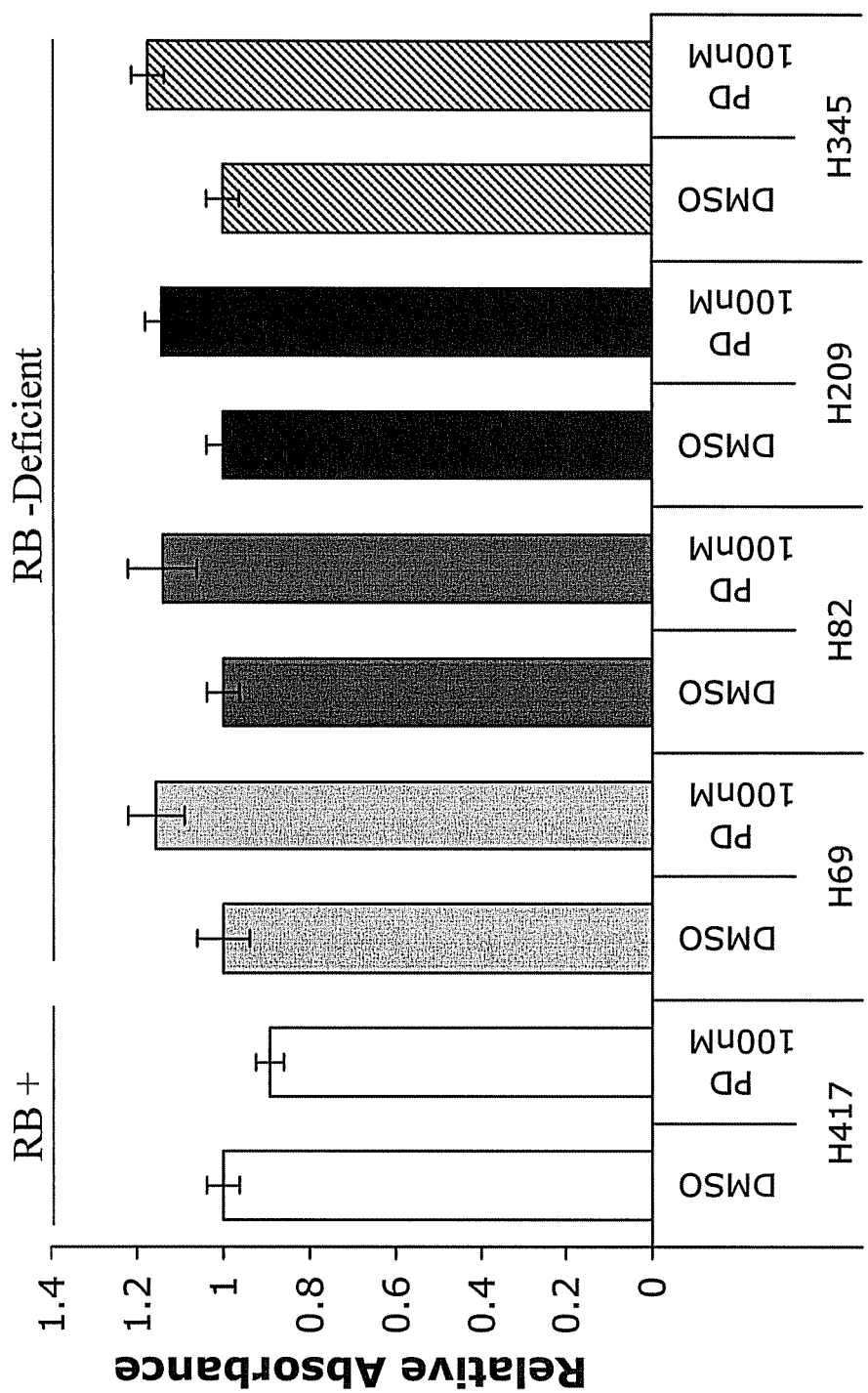
FIG. 8: CDK4/6 inhibition potentiates proliferation of Rb deficient cells. Small cell lung cancer cell lines which are RB null (H69, H82, H209, H345) or with intact RB (H417) were incubated with PD0332991 for 24 hours. Following incubation, media was replaced and the cells grown for 7 days. Cell proliferation was assessed using WST-1 reagent. Each data point represents the mean of four replicates +/−SEM. CDK4/6 inhibition increases cell proliferation of RB-deficient cell lines.

The proliferative effects of CDK4/6 inhibition on a panel of small cell lung cancer (SCLC) cell lines with intact RB (H417) or that were RB-deficient (H69, H82, H209, H345) was evaluated. Cells were treated with DMSO or PD0332991 100 nM for 48 hours and then cell number was estimated using the WST-1 assay, a measure of cellular respiration. See FIG. 8. In the RB-intact SCLC cell line (H417), cell proliferation was decreased, whereas in all four of the RB-deficient cell lines, cell proliferation was actually increased by CDK4/6 inhibition.

The effects of CDK4/6 inhibition in the C3-Tag transgenic mouse model of basal-like breast cancer were also evaluated. The C3-TAg model contains a recombinant gene expressing the simian virus 40 early-region transforming sequence (SV40 large T antigen), which has been shown to inactivate both p53 and RB. Mice were housed up to five per cage with ad libitum access to standard chow and water. Tumor volume was measured by caliper weekly. Tumor volume was calculated using the following formula: Volume=$[(\text{width})^2 \times \text{length}]/2$. After establishing sufficient tumor volume (50-60 mm$^3$), mice were stratified by tumor size and randomly assigned to each of the study cohorts (Untreated, PD0332991 100 mg/kg daily in standard chow, chemotherapy plus vehicle control once a week for 3 weeks, or chemotherapy and PD0332991 once a week for three weeks). In the once a week for 3 week treatment cohorts, chemotherapy was administered by IP injection and PD0332991 150 mg/kg or vehicle control was administered by oral gavage. The chemotherapy regimen consisted of carboplatin 75 mg/kg once a week for three weeks. Treatments were administered on days 0, 7 and 14 and tumor volumes were measured weekly, until the mice died or were euthanized due to toxicity or tumor burden.

Figure 9:
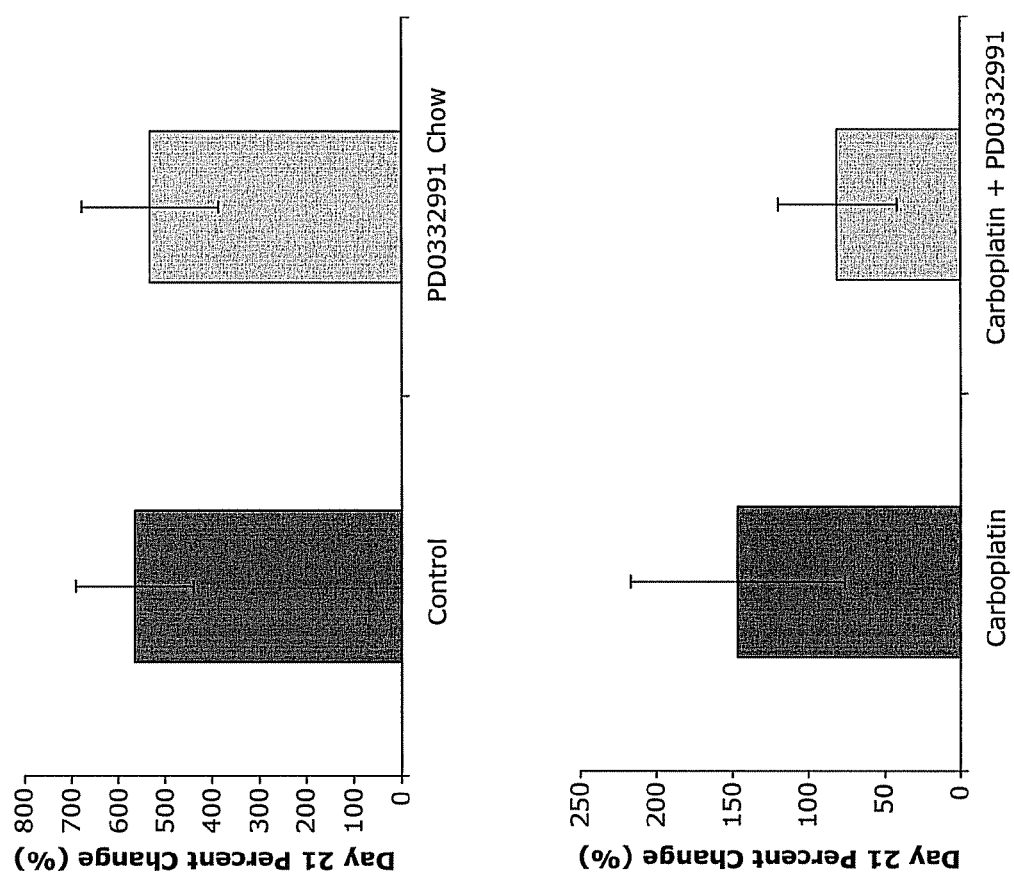
FIG. 9: CDK4/6 inhibition potentiates the efficacy of chemotherapy in mouse model of RB-deficient breast cancer. Mice were treated every 7 days for three weeks with PD0332991 (150 mg/kg PO) alone, carboplatin (90 mg/kg IP) alone or in combination with the PD0332991 (carboplatin+PD0332991). Data are % change in tumor volume and represents the mean of at least 15 animals per cohort +/−SEM
Figure 10:
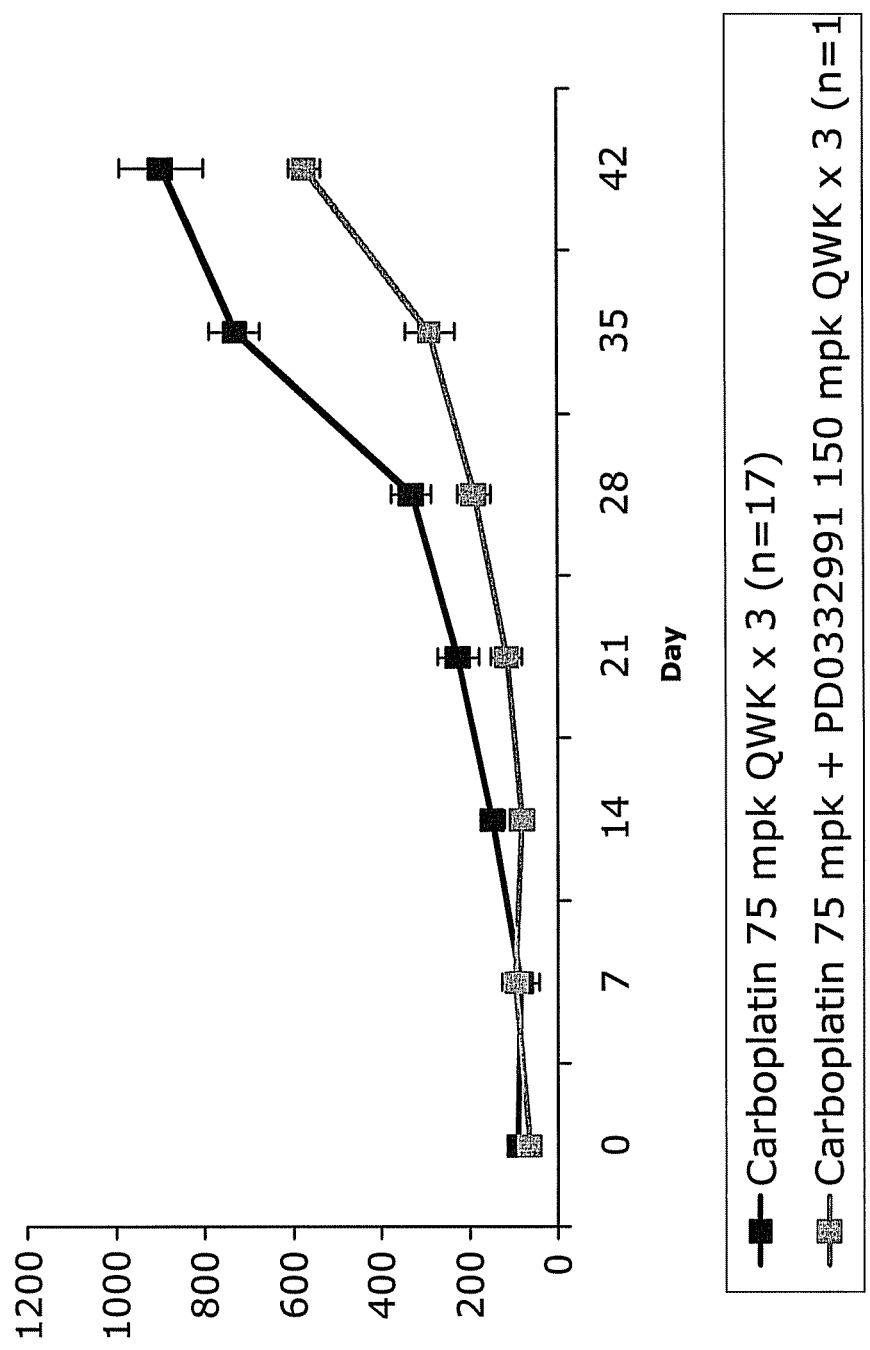
FIG. 10: CDK4/6 inhibition potentiates the efficacy of chemotherapy in mouse model of RB-deficient breast cancer. Mice were treated every 7 days for three weeks with carboplatin (90 mg/kg IP) alone (darkly shaded squares) or in combination with PD0332991 (150 mg/kg PO; lightly shaded squares). Data are % change in tumor volume and represents the mean of at least 15 animals per cohort +/−SEM.

Daily administration of the CDK4/6 inhibitor, PD0332991, had no effect on tumor growth in the C3-Tag model at day 21 (see FIG. 9), whereas co-administration of PD0332991 150 mg/kg with carboplatin 75 mg/kg once a week for 3 weeks resulted in enhanced tumor response in the C3-Tag mice (FIG. 9). In addition, long-term follow-up of the C3-Tag mice showed that tumor progression was delayed in the PD0332991/Carboplatin cohort compared to the Mock Gavage/Carboplatin cohort (FIG. 10). Together these data suggest that, in the treatment of tumors with severe derangements of the cell cycle, CDK4/6 inhibition can enhance the efficacy of chemotherapy.

Accordingly, it appears that CDK4/6 inhibition can augment the efficacy of DNA damaging agents in the treatment of certain cancers with severe derangements of the cell cycle, for example, cancers characterized by very high levels of CDK2 activity (e.g. as a result of amplification of the MYC protooncogene) or loss of the RB tumor suppressor protein. In such tumors, CDK4/6 inhibitors do not induce pharmacological quiescence in the tumor cells, but rather increase the sensitivity of the cancer to DNA damaging agents, thereby increasing tumor kill. CDK4/6 inhibitor treatment simultaneously prevents the host hematologic toxicity of DNA damaging agents (through the induction of quiescence in certain other cells). This increase in tumor kill of RB-null or MYC amplified cancers combined with decreased host toxicity means an increase in the therapeutic window of such tumors, allowing for such tumors to be more easily cured with less toxicity to the patient.

A subset of tumor types such as Her2 amplified breast cancers are expected to be sensitive to CDK4/6 inhibition and thus co-administration of CDK4/6 inhibitor with chemotherapy is likely to result in tumor protection. However, most cancers appear to use the proliferative kinases promiscuously (e.g., can use CDK 1/2/4/or 6). Therefore, isolated inhibition of CDK4/6 should not affect tumor growth in the majority of cancers and CDK4/6 inhibition should not negatively impact the efficacy chemotherapy in these tumor types. In fact, as noted above, CDK4/6 inhibition, with selective small molecule inhibitors, is expected to increase the efficacy of chemotherapeutic agents in certain tumors that are not CDK4/6 dependent. As would be understood by one of skill in the art, such tumors can be deduced based on tumor type and molecular genetics, and, for example, can be cancers characterized by one or more of the group including, but not limited to, increased activity of CDK1 or CDK2, loss or absence of retinoblastoma tumor suppressor protein (RB), high levels of MYC expression, increased cyclin E and increased cyclin A. Such cancers can include, but are not limited to, small cell lung cancer, retinoblastoma, HPV positive malignancies like cervical cancer and certain head and neck cancers, MYC amplified tumors such as Burkitts Lymphoma, and triple negative breast cancer; certain classes of sarcoma, certain classes of non-small cell lung carcinoma, certain classes of melanoma, certain classes of pancreatic cancer, certain classes of leukemia, certain classes of lymphoma, certain classes of brain cancer, certain classes of colon cancer, certain classes of prostate cancer, certain classes of ovarian cancer, certain classes of uterine cancer, certain classes of thyroid and other endocrine tissue cancers, certain classes of salivary cancers, certain classes of thymic carcinomas, certain classes of kidney cancers, certain classes of bladder cancer and certain classes of testicular cancers.

In non-limiting examples, the cancer is selected from a small cell lung cancer, retinoblastoma and triple negative (ER/PR/Her2 negative) or "basal-like" breast cancer. Small cell lung cancer and retinoblastoma almost always inactivate the retinoblastoma tumor suppressor protein (RB), and therefore does not require CDK4/6 activity to proliferate. Thus, CDK4/6 inhibitor treatment will effect pharmacologic quiescence in the bone marrow and other normal host cells, but not in the tumor. Triple negative (basal-like) breast cancer is also almost always RB-null. Also, certain virally induced cancers (e.g. cervical cancer and subsets of Head and Neck cancer) express a viral protein (E7), which inactivates RB making these tumors functionally RB-null. Some lung cancers are also believed to be caused by HPV. As would be understood by one of skill in the art, cancers that are not expected to be affected by CDK4/6 inhibitors (e.g., those that are RB-null, that express viral protein E7, or that overexpress MYC) can be determined through methods including, but not limited to, DNA analysis, immunostaining, Western blot analysis, and gene expression profiling.

Example 6

Blockade of T Cell Proliferation by CDK4/6 Inhibition

Figure 11A:
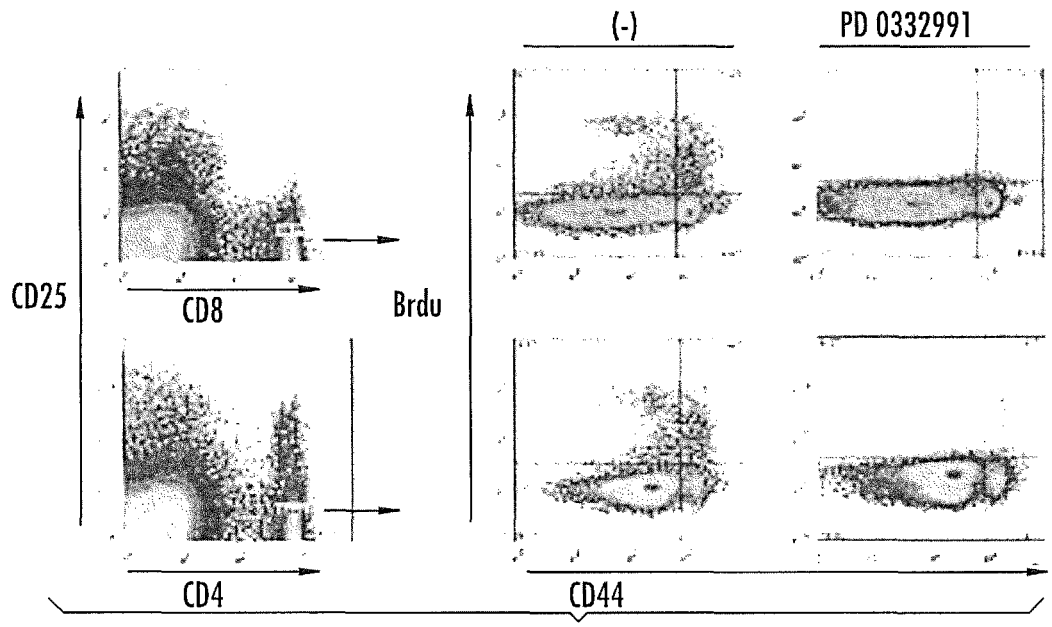
FIG. 11A: Acute inhibition of CDK4/6 selectively suppresses memory T cell homeostatic proliferation in mice. Mice were treated with PD0332991 (150 mg/kg by oral gavage). Proliferation of T-cells were assessed using BrdU and flow cytometry.
Figure 11B:
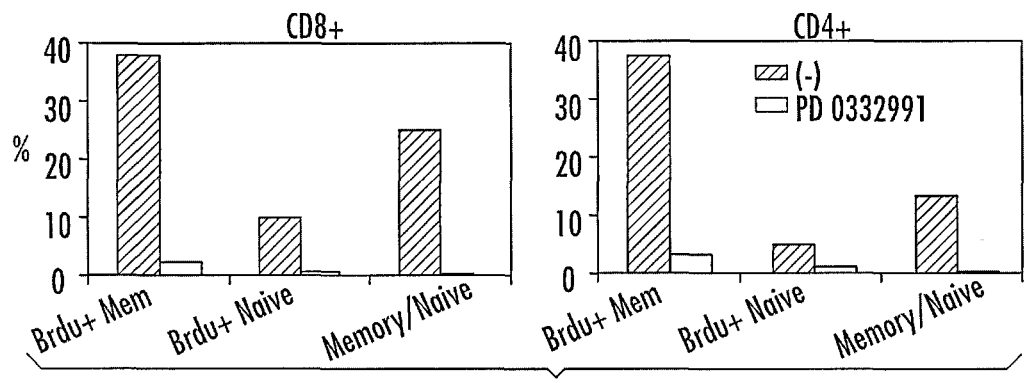
FIG. 11B: Show graphs of the data shown in T-cell proliferation data shown in FIG. 11A.
Figure 11C:
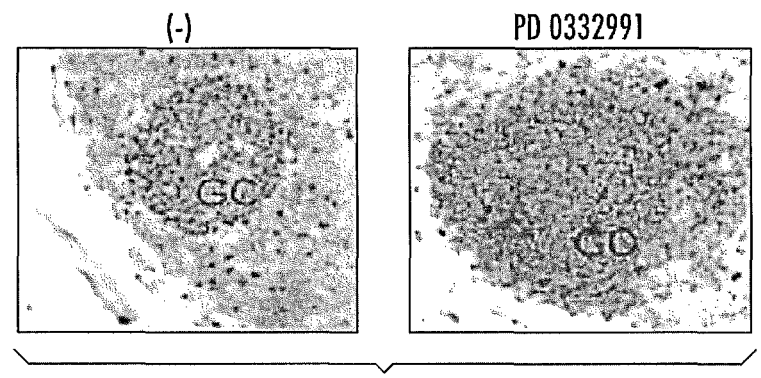
FIG. 11C: Acute inhibition of CDK4/6 selectively suppresses germinal center formation in mice. Mice were treated with PD0332991 (150 mg/kg by oral gavage). Germinal center formation was assessed by Ki67 immunohistochemistry.
Figure 21:
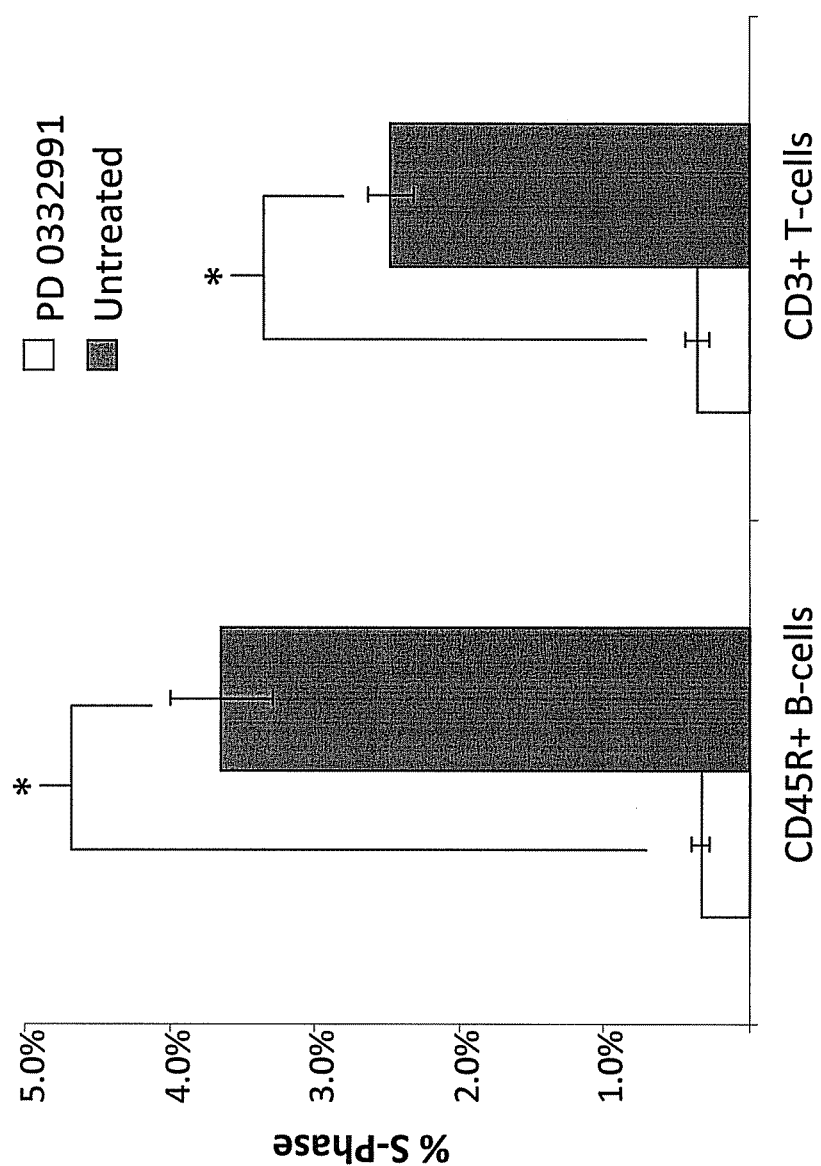
FIG. 21: CDK4/6 inhibition blocks T and B cell proliferation. Animals were treated with CDK4/6 inhibitor (PD0332991, open bars) or vehicle (shaded bars) for 24 hours and euthanized. Splenocytes were isolated and stained for B and T cell markers. After gating on appropriate populations, Ki67 staining was performed as an indicator of proliferation and S-phase. Error bars show +/−SEM.

Acute, pharmacologic inhibition of CDK4/6 suppresses lymphocyte proliferation with the most pronounced effect on memory T cell homeostatic proliferation and germinal center formation in mice. To determine whether inhibiting CDK4/6 affects memory cell generation and maintenance, mice were treated with selective CDK4/6 inhibitors, PD 0332991 or an unrelated selective CDK4/6 inhibitor, 2BrIC. 2BrIC was synthesized by OTAVA Chemicals (Kiev, Ukraine) and can be prepared according to methods described in Zhu et al., *J. Med. Chem.* 46, 2027-2030 (2003). Acute inhibition of CDK4/6 by PD 0332991 or 2BrIC resulted in more significant decrease in homeostatic proliferation of memory T cells than naive T cells, as measured by BrdU incorporation and Ki67 expression in both human and murine cells. See FIGS. 11, 17, 18 and 21. In FIG. 11A, an effect of PD0332991 on in vivo BrdU incorporation of CD4+ and CD8+ murine Tcells, with greatest effects seen in the CD44+CD25+ memory cells (quantified in FIG. 11B). A similar effect on in vivo homeostatic proliferation was noted in unstimulated splenic T cells using Ki67 staining (FIG. 21). Decreased CKD4/6 activity also suppressed germinal center formation, which is relevant to memory B cell generation. See FIG. 11C. These data reveal a role for CDK4/6 in memory cell homeostasis.

Figure 12:
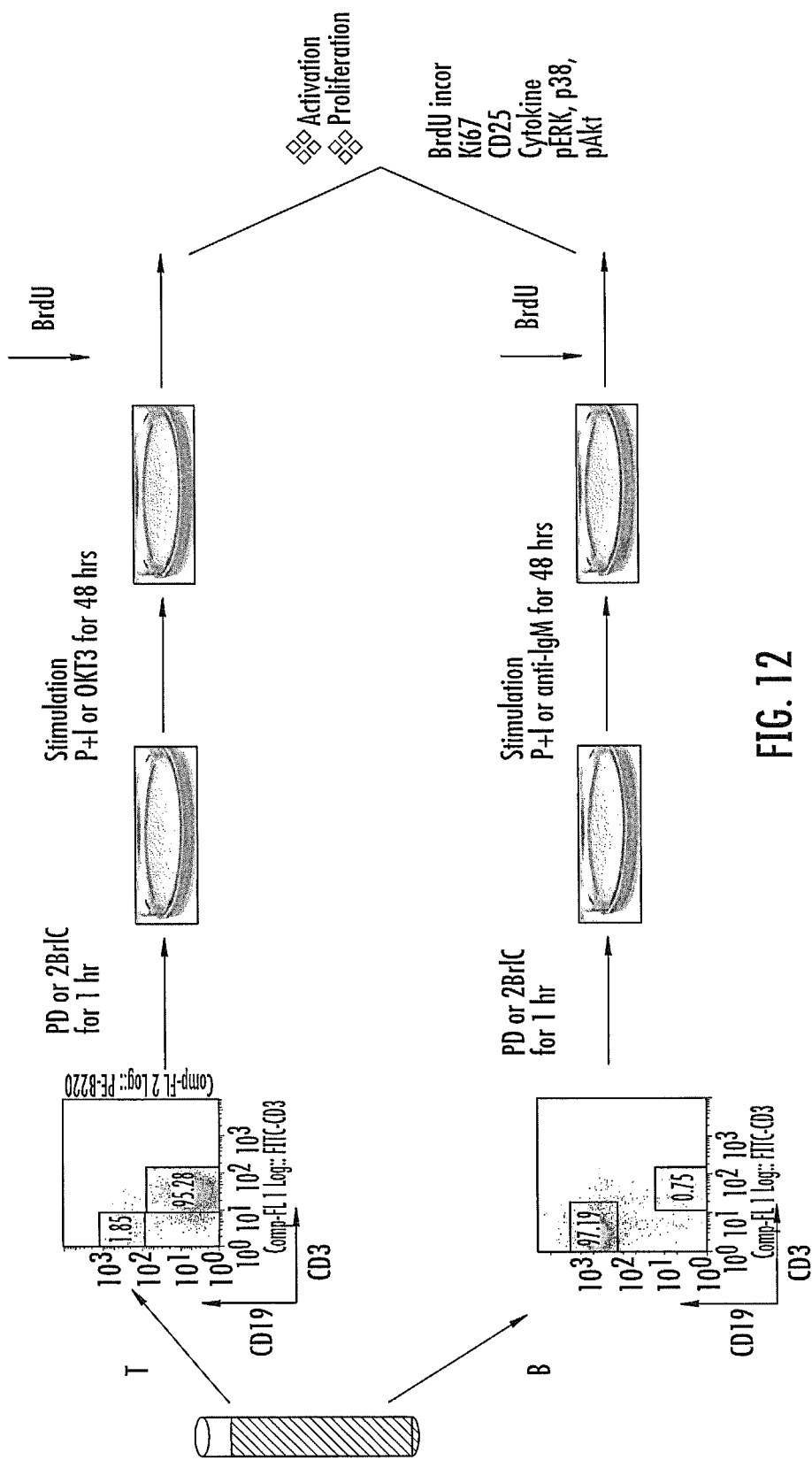
FIG. 12: CDK4/6 inhibitors as human immunosuppressants. Experimental design to test CDK4/6 inhibitors as human immunosuppressants.
Figure 13:
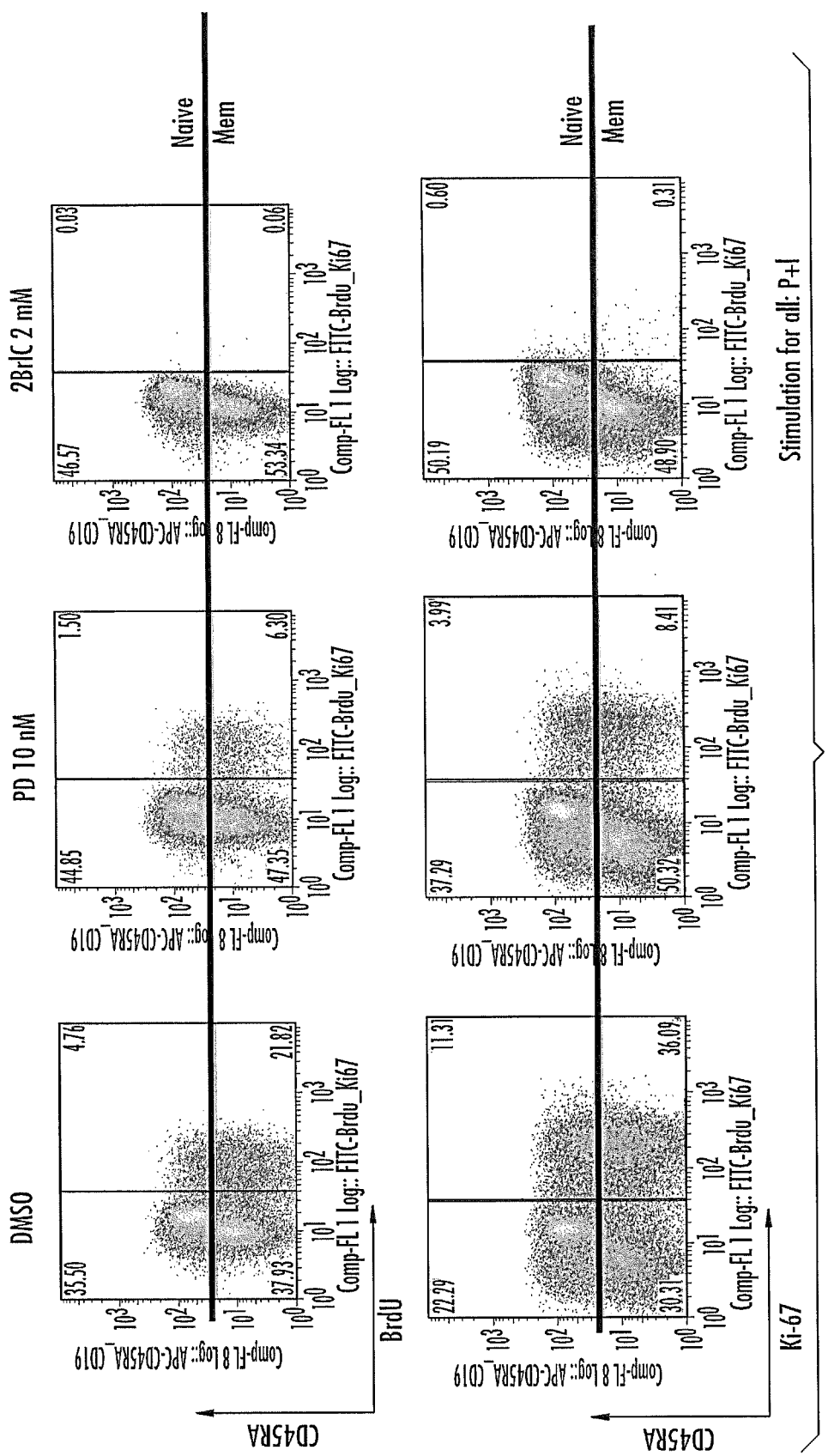
FIG. 13: CDK4/6 inhibitors suppress T cell proliferation upon stimulation through TCR pathway in both memory and naïve compartments. Human peripheral blood T cells were purified using Automacs by CD3 positive selection before being treated with CDK4/6 inhibitors and stimulated with PMA and Inomycin for 48 hrs. The proliferation of memory (CD45RA+) or naïve (CD45RA−) T cells after stimulation by PMA and Inomycin was measured by FACS staining of BrdU+ or Ki-67+ cells. The percentages of inhibition are shown, which indicates more inhibition of memory compartment than naïve compartment.
Figure 14:
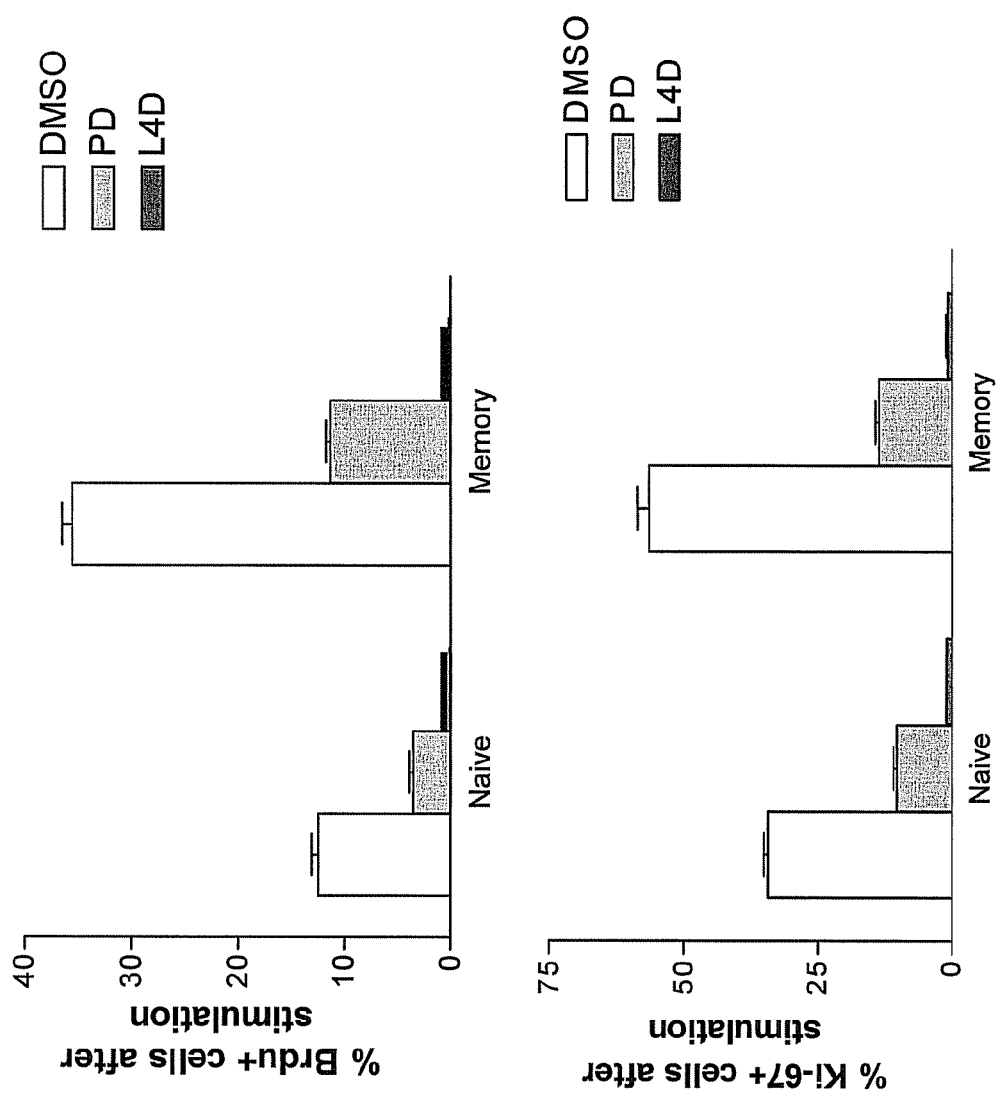
FIG. 14: CDK4/6 inhibitors suppress T cell proliferation upon stimulation through TCR pathway. T cells have more active proliferation upon stimulation through TCR pathway, which was abolished by CDK4/6 inhibition. Similar inhibition was also observed in CD8+ compartment. Proliferation determined by BrdU or Ki67 incorporation. L4D=2BrIC, error bars show +/−SEM.
Figure 15:
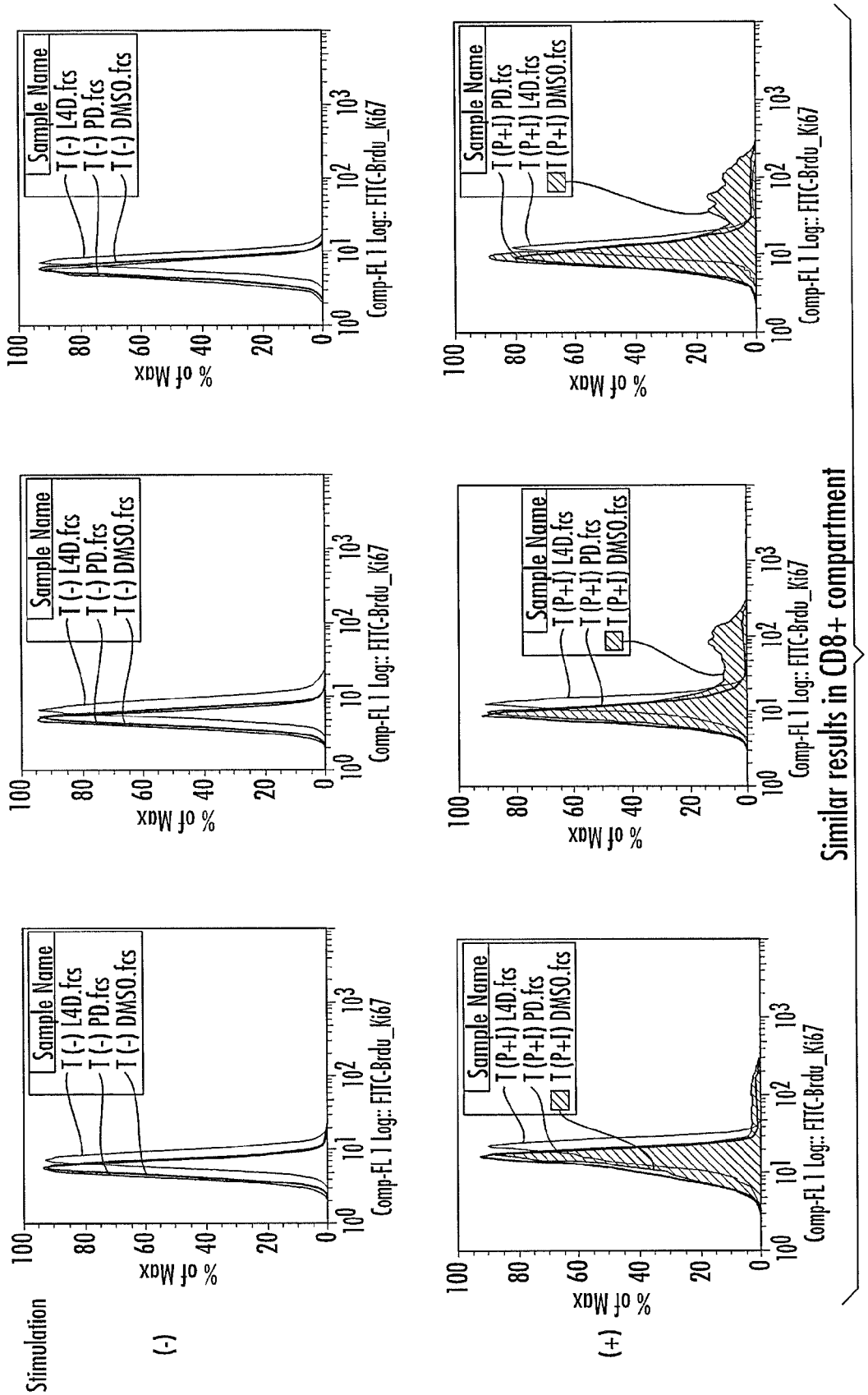
FIG. 15: Changes of CD4 T cell composition after CDK4/6 inhibition. CDK4/6 inhibitors suppress T cell proliferation upon stimulation through TCR pathway. Central memory (CCR7−CD45RA−), effector memory (CCR7+CD45RA+), Naïve (CCR7+CD45RA+) and terminal differentiated T cells (CCR7−CD45RA+) were shown. The memory and terminal differentiated T cell fractions as assessed by BrdU incorporation are reduced after CDK4/6 inhibition. L4D=2BrIC. Similar results in CD8+ compartment.
Figure 16:
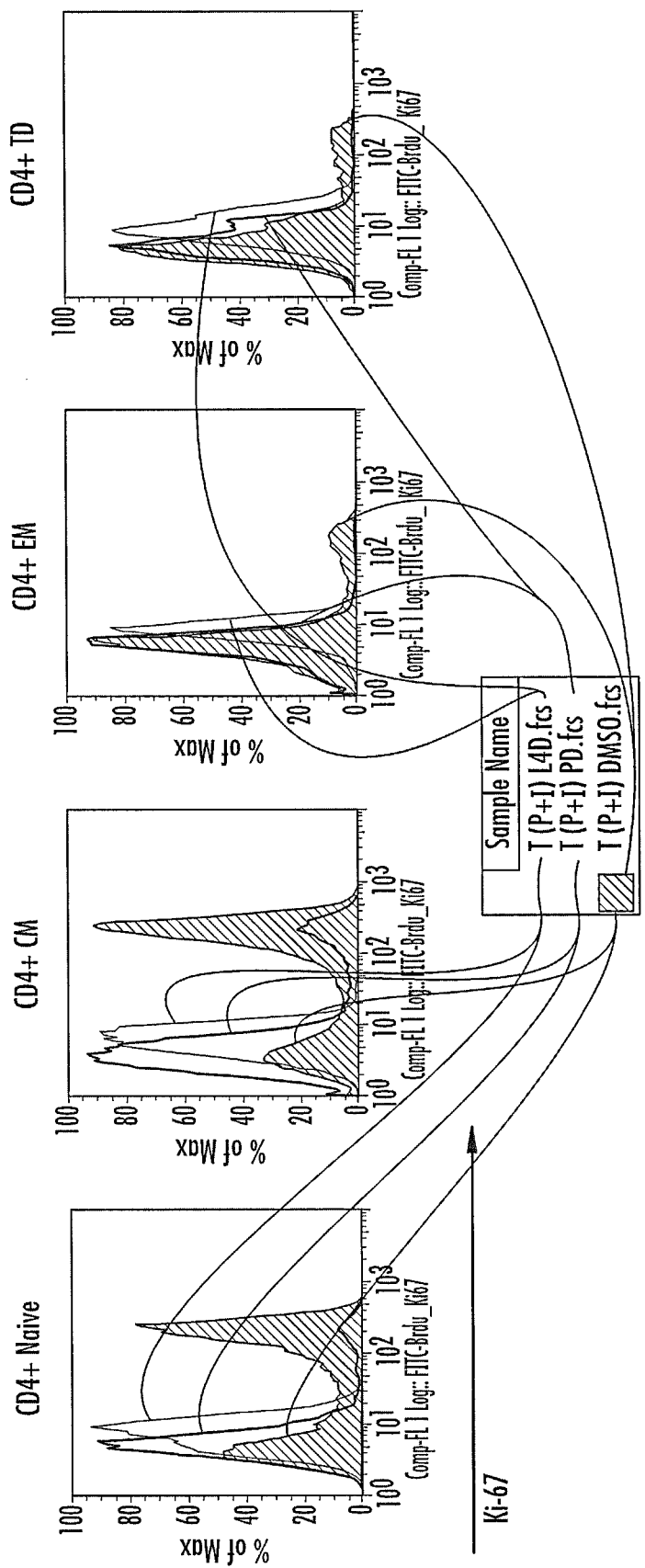
FIG. 16: Changes of CD4 T cell composition after CDK4/6 inhibition. CDK4/6 inhibitors suppress T cell proliferation upon stimulation through TCR pathway. Central memory (CCR7−CD45RA−), effector memory (CCR7+CD45RA+), Naïve (CCR7+CD45RA+) and terminal differentiated T cells (CCR7−CD45RA+) were shown. The memory and terminal differentiated T cell fractions as assessed by Ki67 staining are reduced after CDK4/6 inhibition. L4D=2BrIC.
Figure 18:
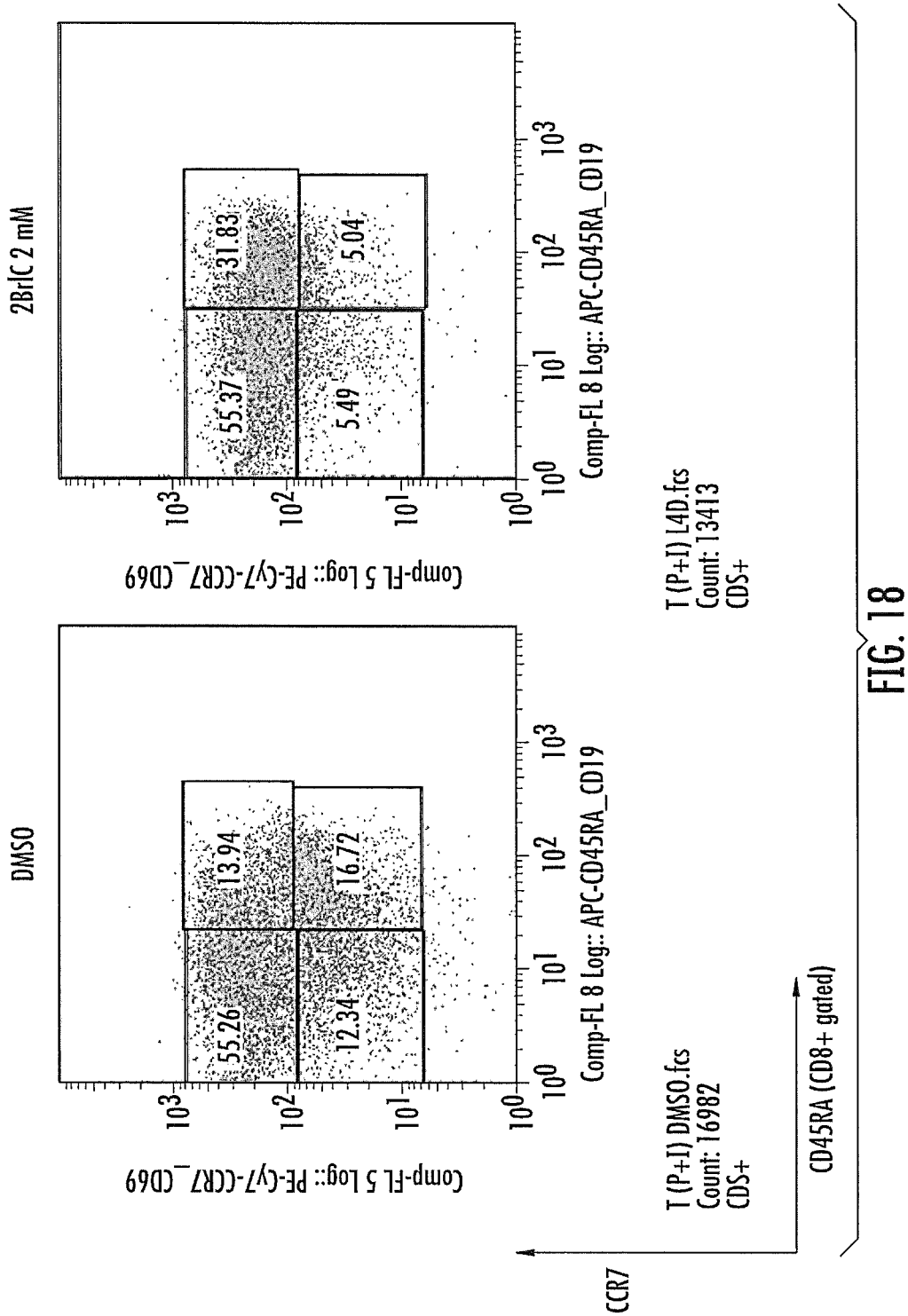
FIG. 18: Preferential inhibition of memory T cell and TD cell proliferation in CD8+ T cells. Central memory (CCR7−CD45RA−), effector memory (CCR7+CD45RA+), Naïve (CCR7+CD45RA+) and terminal differentiated T cells (CCR7−CD45RA+) were shown. The memory and terminal differentiated T cell fractions are reduced after CDK4/6 inhibition. L4D=2BrIC.
Figure 19:
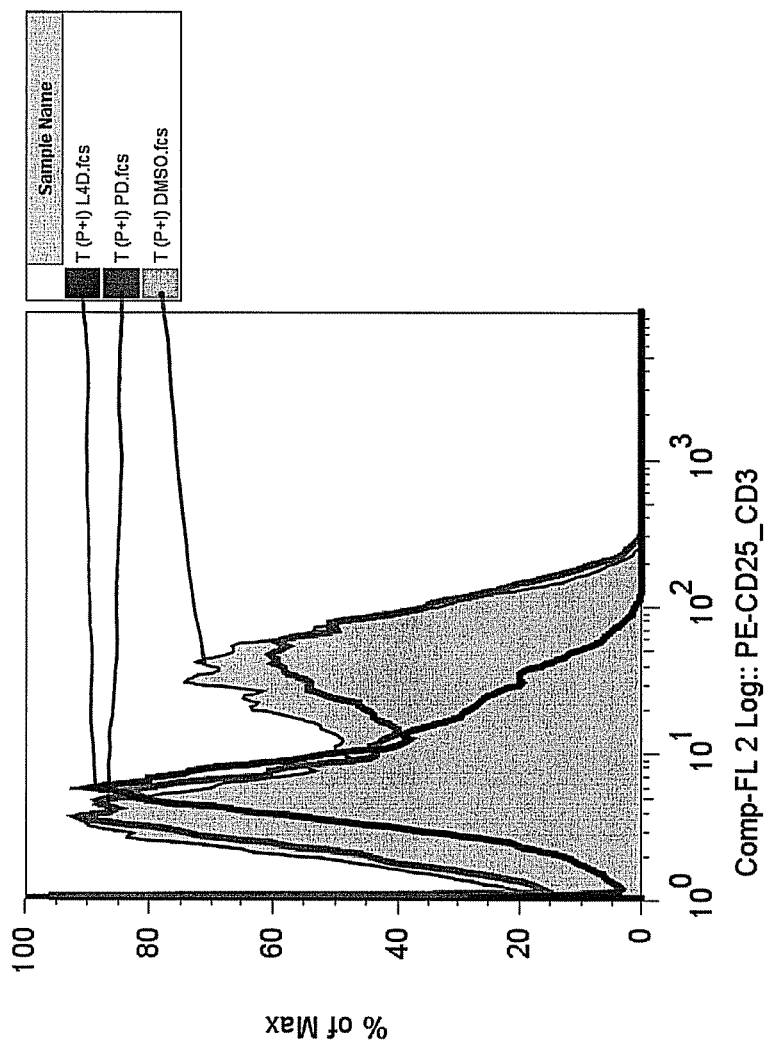
FIG. 19: Preferential inhibition of memory T cell and TD cell proliferation. CDK4/6 inhibitors inhibit T cell activation through PMA and ionomycin. Purified human peripheral T cells were stimulated with PMA and ionomycin with or without CDK4/6 inhibitor treatment. The fraction of activated T cells (CD25+) upon stimulation was measured by FACS. T cell activation was found to be decreased after CDK4/6 inhibitor treatment. L4D=2BrIC.

Similar results were seen using human lymphocytes. FIG. 12 shows an experimental scheme to address similar issues in human cells. Human lymphocytes are sorted to T(CD3+) and B(CD19+) cells and treated in vitro with CDK4/6 inhibitor prior to stimulation with PMA and Inomycin (P+I)+OKT3 (Tcells) or IgM (Bcells), with proliferation assessed by BrdU uptake and Ki67y expression, and activation assessed by CD25 expression. FIG. 13 shows that as in murine cells, CDK4/6 inhibitors block proliferation in response to Tcell receptor (TCR) stimulation (P+I), with a greater effect in CD45 RA low memory cells. These data are graphed in FIG. 14. In FIG. 15, the effects of CDK4/6 inhibition on specific Tcell fractions is assessed, with and without TCR, showing CDK4/6 inhibition has a greater effect on proliferation of memory cells relative to naïve cells. A similar effect was seen in CD8+ cells. FIG. 16 shows similar data as in FIG. 15, but using Ki67 as a marker of proliferation instead of BrdU. These effects on proliferation change the relative frequencies of CD4+ (see FIGS. 17A, 17B, and 17C) and CD8+ (see FIG. 18) cells. CDK4/6 inhibitors decrease the CD4+ effector memory (EM) cell frequency to a greater extent than naïve cells. See FIGS. 17A and 17C. A similar result is seen in CD8+ cells. As a result of these effects on proliferation, memory/naive ratio decreased by half in both CD4+ and CD8+ compartments. See FIGS. 17B and 20. These alterations in proliferation are associated with decreased T cell activation as measured by CD25 expression. See FIG. 19.

This ability to inhibit T cell proliferation can be of use in the therapy of autoimmune and allergic diseases. These conditions are presently treated with a variety of cytotoxic and steroidal agents that have significant toxicity. The memory T cell compartment has been difficult to target in order to attenuate anemnestic immune responses, and the use of CDK4/6 inhibitors to reduce proliferation of this fraction will be particularly useful for therapy of autoimmune and allergic diseases.

Figure 23:
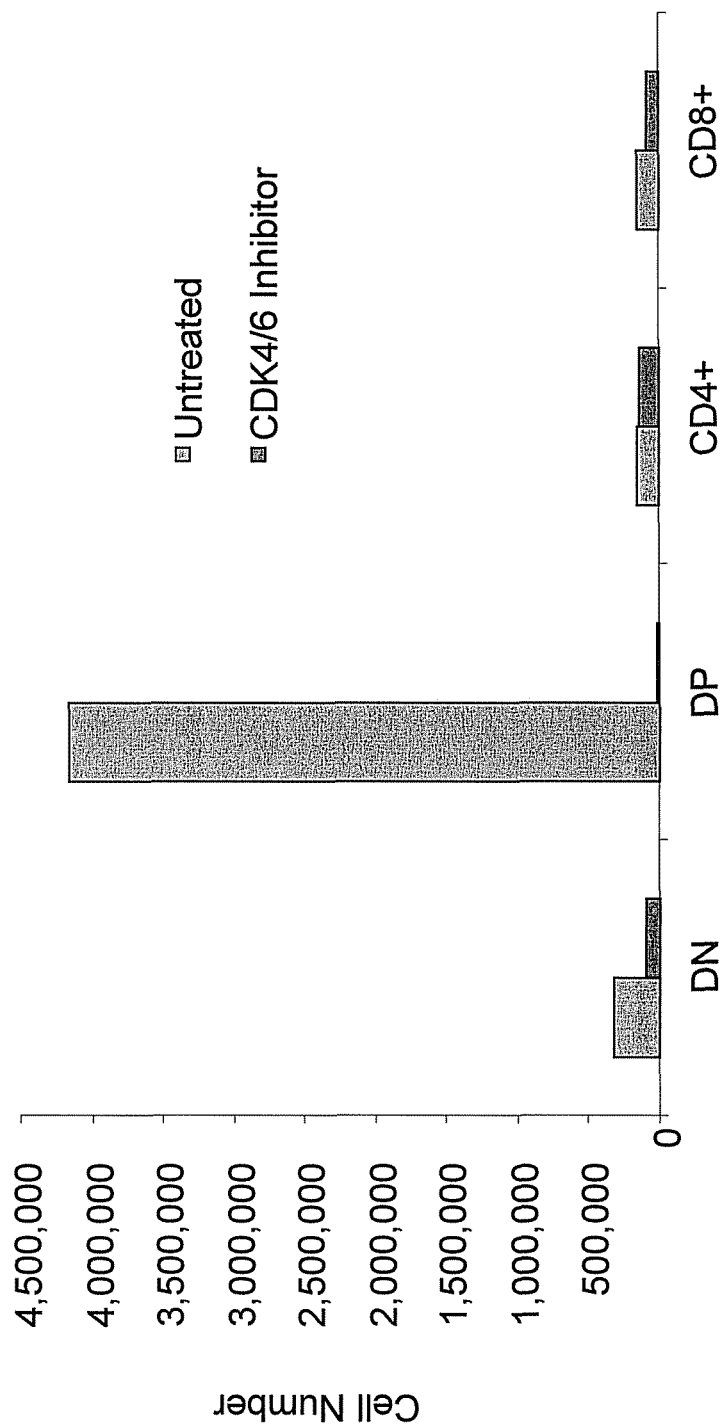
FIG. 23: CDK4/6 inhibitors block Thymopoiesis. Animals were treated with CDK4/6 inhibitor (150 mg/kg by daily oral gavage) or vehicle for 4 days, and then thymocyte number assessed by flow cytometry for Double negative (DN:CD4−CD8−), Double Positive (DP:CD4+CD8+) or CD4 or CD8 singly positive cells. CDK4/6 inhibition produced a pronounced decrease in the production of new DP cells, with modest effects on the DN and SP fractions.

Thymocyte Differentiation:

The effect of CDK4/6 inhibition on thymocyte development was assessed by determining the percentages and absolute numbers of thymocytes at different stages (Double Negative (DN): CD4−CD8−; Double Positive (DP): CD4+ CD8+; Single Positive (SP): CD4+ or CD8+) by FACS. DN cells are converted to DP cells which are then converted to cells singly positive for CD4 or CD8. Transient CDK4/6 inhibition produced a pronounced reduction in DP and SP cells, with relative sparing of DN cells. This result suggests that CDK4/6 activation is required during thymopoiesis for the production of new naïve Tcells. See FIG. 23.

Example 7

Blockade of B Cell Proliferation by CDK4/6 Inhibition

Figure 20:
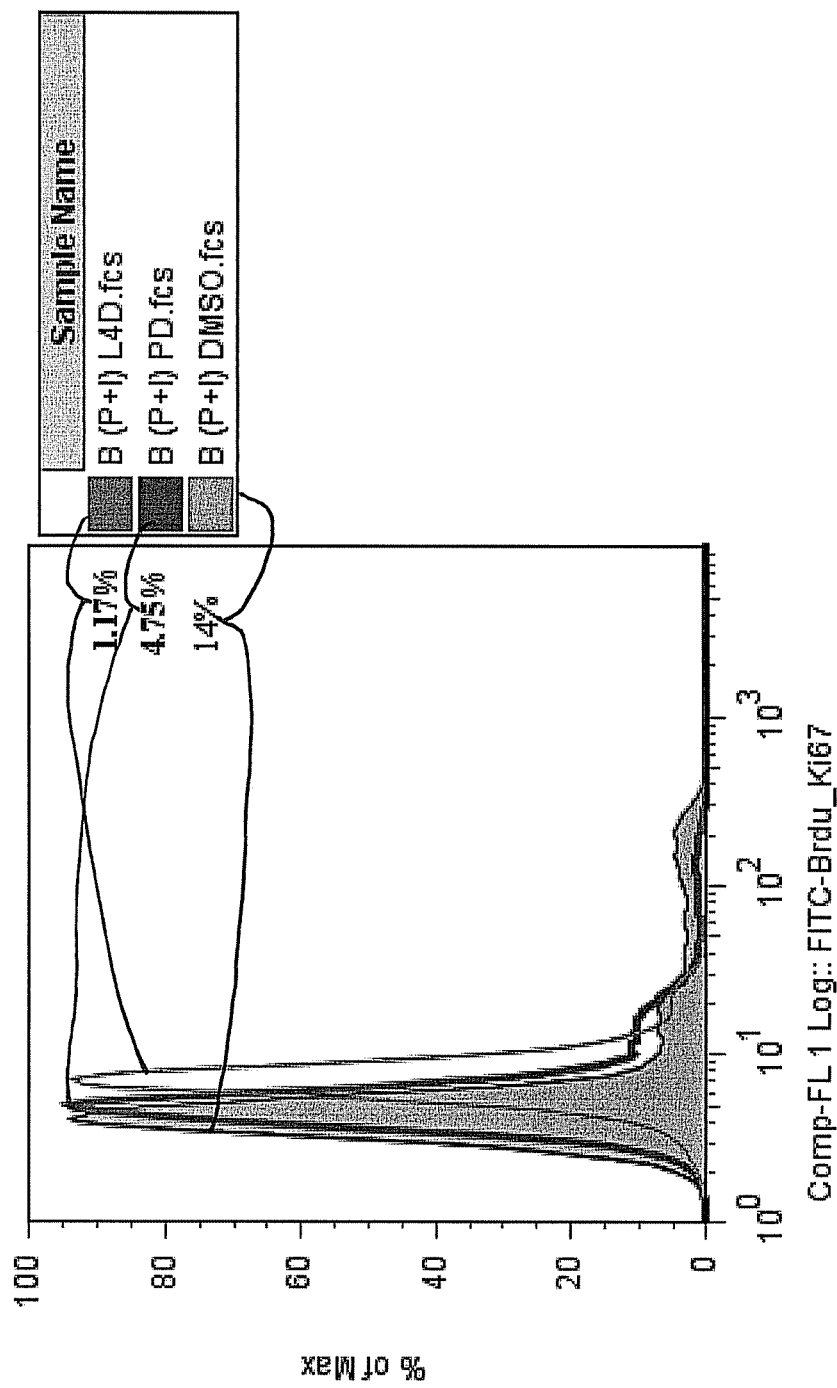
FIG. 20: CDK4/6 inhibitors suppress B cell proliferation after stimulation through BCR. B cells were purified by Automacs selection of CD19+ cells. The BrdU incorporation of purified human peripheral B cells was determined after anti-IgM stimulation with or without CDK4/6 inhibitor treatment. The fraction of proliferating B cells reduced ~10 fold after L4D inhibition. L4D=2BrIC
Figure 22:
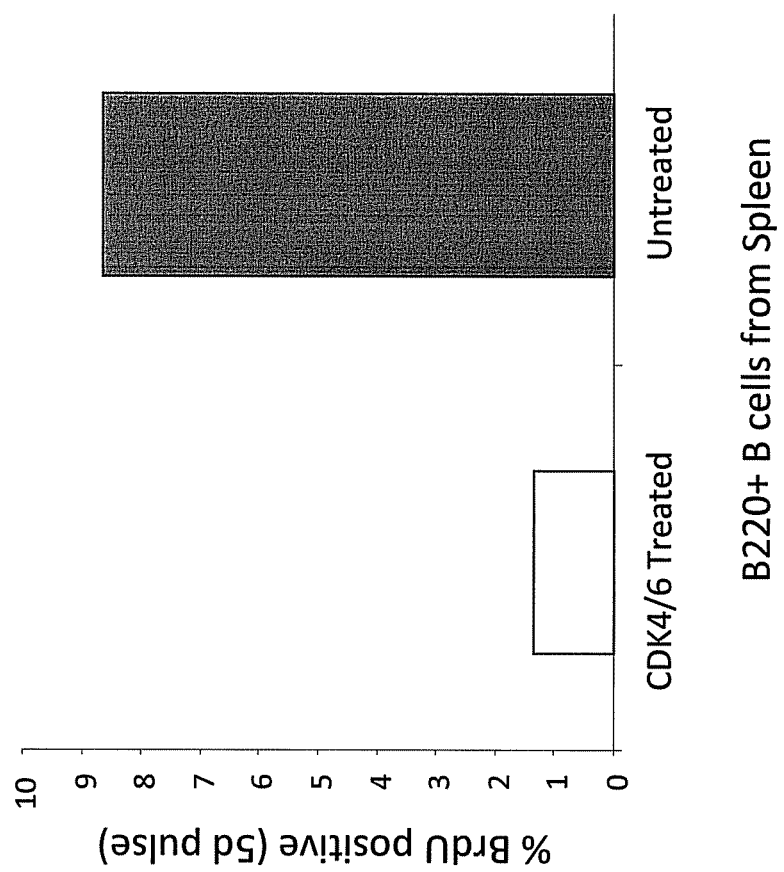
FIG. 22: CDK4/6 inhibitors block B-cell proliferation. Animals were treated with CDK4/6 inhibitor (150 mg/kg by daily oral gavage) or vehicle for 4 days, and BrdU in the drinking water for 3 days. After BrdU treatment, animals were euthanized. Splenocytes were isolated and stained for B cell markers. After gating on appropriate populations, BrdU staining was performed as an indicator of proliferation.

Cohorts of wild type mice were treated with vehicle or a CDK4/6 inhibitor as in FIG. 11. Ki67 staining of a germinal center in a lymph node shows a marked decreased in proliferation with CDK4/6 inhibition. A similar result was seen in splenic CD45R+ B-cells. See FIG. 21. Unstimulated mice were treated for 24 hours with PD0332991 and homeostatic B cell proliferation measured by Ki67 staining after appropriate sorting. Similar results were obtained using BrdU incorporation to measure splenic B cell proliferation. See FIG. 22. Similar experiments were undertaken in human cells with B cell receptor stimulation as described in FIG. 12. FIG. 20 shows that CDK4/6 inhibition blocks Bcell stimulation by P+I. These results show that homeostatic, germinal center and BCR-induced Bcell proliferation requires CDK4/6 activity in mice and humans.

Example 8

Suppression of Autoimmune Disease Development by CDK4/CDK6 Inhibition

Several lines of autoimmune mouse models have been developed, including NOD mice (spontaneous autoimmune diabetes) and Lyn–/– (lupus like autoimmune disease). See, e.g., Anderson and Bluestone, *Annual Review of Immunology* 23, 447-485 (2005); and Hibbs et al., *Cell* 83, 301-311 (1995). Cohorts of both young (about 4-6 weeks) and old (>30 weeks) mice are treated with placebo or a CDK4/6 inhibitor for defined periods of time before being analyzed for autoimmune phenotypes.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method for promoting the recovery of a hematopoietic cell population in a subject undergoing treatment for a cyclin dependent kinase 4 and/or cyclin dependent kinase 6 (CDK4/6)-replication independent cancer, the method comprising: (a) administering to the subject a pharmaceutically effective amount of a selective CDK4/6 inhibitor compound having a 50% inhibitory concentration ($IC_{50}$) for cyclin dependent kinase 4 (CDK4) that is at least 6 times lower than the compound's $IC_{50}$ for cyclin dependent kinase 2 (CDK2); (b) administering to the subject a DNA damaging agent to treat the CDK4/6-replication independent cancer, wherein the administering of the DNA damaging agent is performed after the administering of (a); and (c) administering to the subject a growth factor.

2. The method of claim 1, wherein the growth factor comprises one or more agents selected from the group consisting of a granulocyte colony-stimulating factor (G-CSF), a pegylated G-CSF, granulocyte-macrophage colony stimulating factor (GM-CSF), thrombopoietin, erythropoietin, pegylated erythropoietin, interleukin (IL)-12, steel factor, and a keratinocyte growth factor.

3. The method of claim 2, wherein the growth factor is selected from the group consisting of erythropoietin and pegylated erythropoietin.

4. The method of claim 2, wherein the growth factor is selected from the group consisting of colony-stimulating factor and pegylated colony-stimulating factor.

5. The method of claim 2, wherein the growth factor is granulocyte-macrophage colony-stimulating factor.

6. The method of claim 1, wherein the DNA damaging agent is a chemotherapeutic agent.

7. The method of claim 6, wherein the chemotherapeutic agent is selected from the group consisting of adrimycin, 5-fluorouracil, etoposide, camptothecin, actinomycin-D, mitomycin, cisplatin, hydrogen peroxide, carboplatin, procarbazine, mechlorethamine, cyclophosphamide, ifosfamide, melphalan, chlorambucil, busulfan, nitrosurea, dactinomycin, daunorubicin, doxorubicin, bleomycin, plicomycin, tamoxifen, taxol, transplatinum, vinblastin, and methotrexate.

8. The method of claim 1, wherein the DNA damaging agent is ionizing radiation.

9. The method of claim 1, wherein the growth factor is administered at least about 24 hours after the administration of the DNA damaging agent.

10. The method of claim 9, wherein the growth factor is administered at least about 72 hours after the administration of the DNA damaging agent.

11. The method of claim 1, wherein the subject is undergoing treatment for a CDK4/6-replication independent cancer selected from the group consisting of small cell lung cancer, retinoblastoma, and triple negative breast cancer.

12. The method of claim 1, wherein the CDK4/6-replication independent cancer has an increased activity of cyclin dependent kinase 1 (CDK1) or CDK2, loss or absence of the retinoblastoma tumor suppressor protein (RB), a high level of MYC expression, increased cyclin E1, increased cyclin E2, increased cyclin A, or an overexpression of RB-activating protein.

13. The method of claim 1, wherein the hematopoietic cell population is red blood cells.

14. The method of claim 1, wherein the hematopoietic cell population is white blood cells.

15. The method of claim 14, wherein the white blood cells are lymphocytes.

16. The method of claim 1, wherein the hematopoietic cell population is platelets.

17. The method of claim 1, wherein the selective CDK4/6 inhibitor compound has an $IC_{50}$ for CDK4 that is at least 8 times lower than the compound's $IC_{50}$ for CDK2.

* * * * *